United States Patent
Watnick et al.

(10) Patent No.: US 12,377,079 B2
(45) Date of Patent: Aug. 5, 2025

(54) ANTIBACTERIAL COMPOUNDS AND USES THEREOF

(71) Applicant: The Children's Medical Center Corporation, Boston, MA (US)

(72) Inventors: Paula I. Watnick, Boston, MA (US); Julie Szu Yu, Boston, MA (US)

(73) Assignee: The Children's Medical Center Corporation

( * ) Notice: Subject to any disclaimer, the term of this patent is extended or adjusted under 35 U.S.C. 154(b) by 926 days.

(21) Appl. No.: 17/311,433

(22) PCT Filed: Dec. 5, 2019

(86) PCT No.: PCT/US2019/064652
§ 371 (c)(1),
(2) Date: Jun. 7, 2021

(87) PCT Pub. No.: WO2020/118036
PCT Pub. Date: Jun. 11, 2020

(65) Prior Publication Data
US 2022/0023270 A1    Jan. 27, 2022

Related U.S. Application Data

(60) Provisional application No. 62/776,134, filed on Dec. 6, 2018.

(51) Int. Cl.
| | | |
|---|---|---|
| *A61K 31/433* | (2006.01) | |
| *A61K 31/165* | (2006.01) | |
| *A61K 31/341* | (2006.01) | |
| *A61K 31/357* | (2006.01) | |
| *A61K 31/4525* | (2006.01) | |
| *A61K 31/519* | (2006.01) | |
| *A61P 31/04* | (2006.01) | |

(52) U.S. Cl.
CPC .......... *A61K 31/433* (2013.01); *A61K 31/165* (2013.01); *A61K 31/341* (2013.01); *A61K 31/357* (2013.01); *A61K 31/4525* (2013.01); *A61K 31/519* (2013.01); *A61P 31/04* (2018.01)

(58) Field of Classification Search
CPC .. A61K 31/433; A61K 31/165; A61K 31/341; A61K 31/357; A61K 31/4525; A61K 31/519; A61P 31/04
USPC ....................................... 514/259.3
See application file for complete search history.

(56) References Cited

U.S. PATENT DOCUMENTS

| | | |
|---|---|---|
| 9,221,765 B2 | 12/2015 | Melander et al. |
| 2005/0124638 A1 | 6/2005 | Swayze et al. |
| 2013/0136782 A1 | 5/2013 | Blackwell et al. |

FOREIGN PATENT DOCUMENTS

WO    2017/106134 A1    6/2017

OTHER PUBLICATIONS

Vallone et al., 2018, European Journal of Medicinal Chemistry, 150, 698-718 (Year: 2018).*

* cited by examiner

*Primary Examiner* — Kristin A Vajda
(74) *Attorney, Agent, or Firm* — NIXON PEABODY LLP; David S. Resnick; Jeanne N. Jodoin

(57) ABSTRACT

Provided herein are compositions and methods for the treatment of infections resulting from antibiotic-resistant strains of bacteria.

4 Claims, 19 Drawing Sheets

A06

I17

O06

F02

G13
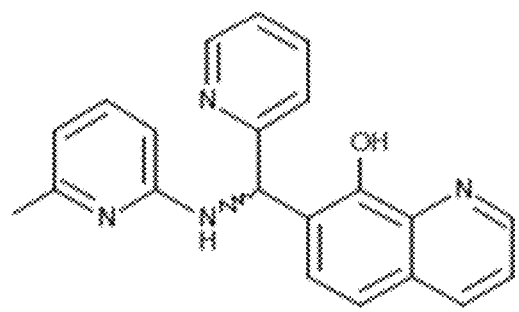
L17
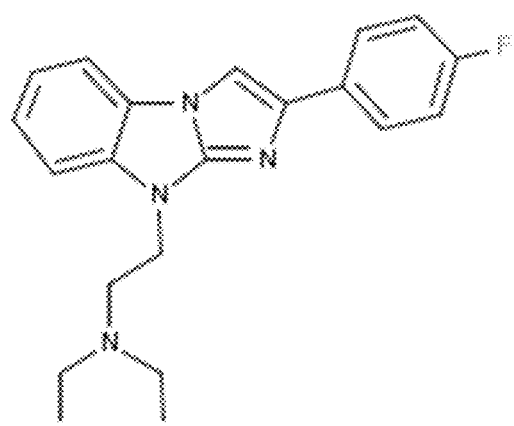
C17
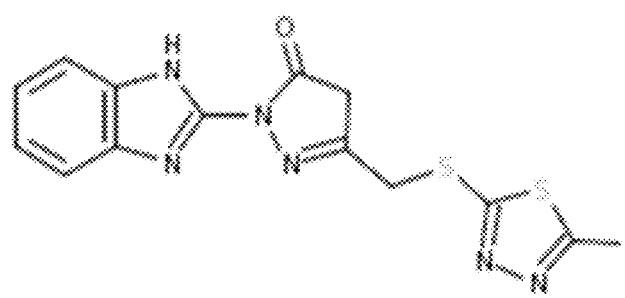
N08
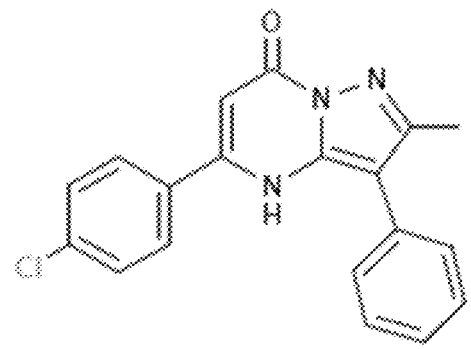
*FIG. 2C, continued*

ANTIBACTERIAL COMPOUNDS AND USES THEREOF

CROSS REFERENCE TO RELATED APPLICATIONS

This application is a 35 U.S.C. § 371 National Phase Entry Application of International Patent Application No. PCT/US2019/064652 filed on Dec. 5, 2019, which designates the US and which claims benefit under 35 U.S.C. § 119(e) of U.S. Provisional Application 62/776,134 filed on Dec. 6, 2018, the contents of each of which are incorporated herein by reference in their entirety.

FIELD OF THE INVENTION

The field of the invention relates to novel antibacterial compounds and methods for using such compounds in the treatment of bacterial infections that are resistant to conventional antibiotics.

BACKGROUND

There is a need for new antimicrobials to combat the inexorable rise of multi-drug resistant bacteria for the treatment of infections that are resistant to at least one antibiotic. One example of an antibiotic resistant infection relates to carbapenem-resistant Gram-negative bacteria and, in particular, the carbapenem-resistant Enterobacteriaceae, where treatment options are limited [1]. For this reason, the Centers for Disease Control and Prevention as well as the World Health Organization have designated carbapenem-resistant Enterobacteriaceae a threat that merits the highest priority for research and development of new antibiotics [2]. The increasing incidence of infections caused by carbapenem-resistant (CR) *Klebsiella pneumoniae*, which belong to the Enterobacteriaceae family, is particularly concerning because a recent meta-analysis of reports published between 1999 and 2015 found that the worldwide mortality of patients infected by CR *K. pneumoniae* could be as high as 50% [3].

Gram-negative bacteria are intrinsically more resistant to antimicrobial compounds than Gram-positive organisms due to (i) the requirement for penetration of both the negatively charged outer and lipophilic inner membranes, (ii) stringent transcriptional and post-transcriptional control of porin expression in the outer membrane, and (iii) expression of multi-drug efflux pumps [4-6].

SUMMARY

Provided herein, in part, are antibacterial agents that are effective against antibiotic-resistant strains of bacteria. These antibacterial agents were discovered by screening libraries of natural and synthetic compounds in a whole cell bacterial assay using an antibiotic-resistant strain of bacteria (e.g., carbapenem-resistant *Klebsiella pneumoniae*). The agents identified can be used in the treatment of infections comprising antibiotic-resistant bacteria including, but not limited to, carbapenem-resistant *K. pneumoniae*, methicillin-resistant *Staphylococcus aureus* (MRSA), carbapenem-resistant *Escherichia coli*, and antibiotic-resistant *Pseudomonas aeruginosa* (e.g., strain PA01). The compounds identified are contemplated for use in place of conventional antibiotics in the treatment of antibiotic-resistant Enterobacteriaceae, such as carbapenem-resistant Enterobacteriaceae.

In addition, provided herein are methods for enhancing effectiveness of the antibacterial agents identified in the whole cell bacterial screen described herein by administering the antibacterial agent in combination with an efflux pump inhibitor, such as phenylalanyl arginyl β-naphthylamide (PAβN).

In one aspect, provided herein is a pharmaceutical composition for the treatment of an antibiotic-resistant bacterial infection, the composition comprising a therapeutically effective amount of a compound of Formula I or stereoisomers, tautomers, or pharmaceutically acceptable salts thereof and a pharmaceutically acceptable carrier;

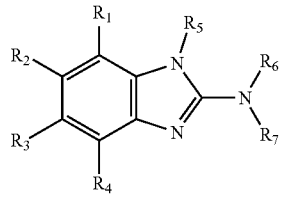

I wherein:

$R_1$, $R_2$, $R_3$, and $R_4$ independently are H, alkyl, aryl, heteroaryl, heteroalkyl, cycloalkyl, heterocyclyl, acyl, allyl, OH, alkoxy, cyano, carboxy, $CF_3$, halide, NH(alkyl), NH(aryl) or $NH_2$;

$R_5$ is H, alkyl, aryl, heteroaryl, heteroalkyl, cycloalkyl, heterocyclyl, acyl, or allyl;

$R_6$ and $R_7$ are independently H, alkyl, aryl, heteroaryl, heteroalkyl, cycloalkyl, heterocyclyl, acyl, or allyl; or $R_6$ and $R_7$ together with the nitrogen they are bonded to form a heterocyclyl or a heteroaryl;

wherein any alkyl, alkenyl, cycloalkyl, heterocyclyl, heteroaryl or aryl is optionally substituted with 1, 2, or 3 groups selected from OH, CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)$alkyl$]_2$, $C(O)NH_2$, COOH, COOMe, acetyl, $(C_1$-$C_8)$alkyl, $O(C_1$-$C_8)$alkyl, $O(C_1$-$C_8)$haloalkyl, $(C_2$-$C_8)$alkenyl, $(C_2$-$C_8)$alkynyl, haloalkyl, thioalkyl, cyanomethylene, alkylaminyl, aryl, heteroaryl, substituted aryl, $NH_2$—C(O)-alkylene, NH(Me)-C(O)-alkylene, $CH_2$—C(O)-lower alkyl, C(O)-lower alkyl, alkylcarbonylaminyl, $CH_2$—[CH(OH)$]_m$—(CH$_2$)$_p$—OH, $CH_2$—[CH(OH)$]_m$—(CH$_2$)$_p$—$NH_2$ or $CH_2$-aryl-alkoxy; or wherein any alkyl, cycloalkyl or heterocyclyl is optionally substituted with oxo; "m" and "p" are independently 1, 2, 3, 4, 5 or 6.

In one embodiment of this aspect and all other aspects provided herein, at least one of $R_1$, $R_2$, $R_3$, and $R_4$ is H and at least one of $R_1$, $R_2$, $R_3$, and $R_4$ is $NH_2$.

In another embodiment of this aspect and all other aspects provided herein, $R_5$ is a linear $C_1$-$C_6$ substituted alkyl where the terminal carbon is substituted with $N[(C_1$-$C_4)$alkyl$]_2$.

In another embodiment of this aspect and all other aspects provided herein, $R_6$ is H and $R_7$ is a methyl substituted with an aryl group.

In another embodiment of this aspect and all other aspects provided herein, $R_7$ is the para-(diethyl amino) benzyl substituted methyl group fragment A;

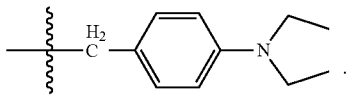

A

In another embodiment of this aspect and all other aspects provided herein, the compound is

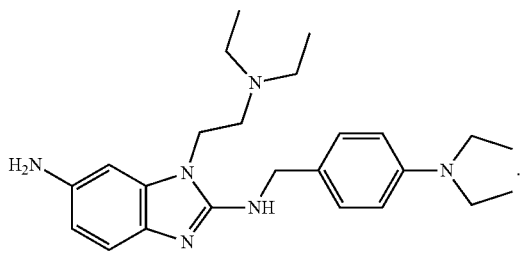

N09

In another embodiment of this aspect and all other aspects provided herein, $R_6$ and $R_7$ together with the nitrogen they are bonded to form a substituted oxo-pyrazole, wherein $R_6$ is N and $R_7$ is an oxo group bonded to a carbon.

In another embodiment of this aspect and all other aspects provided herein, the compound is:

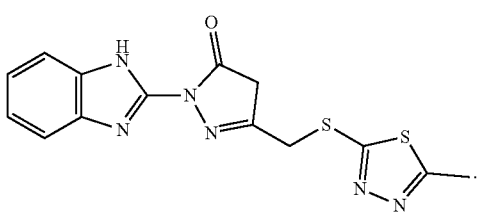

C17

In another embodiment of this aspect and all other aspects provided herein, the composition further comprises an effective amount or a therapeutically effective amount of an efflux pump inhibitor.

In another embodiment of this aspect and all other aspects provided herein, the efflux pump inhibitor is phenylalanyl arginyl b-naphthylamide (PAβN).

In another embodiment of this aspect and all other aspects provided herein, the composition is formulated for topical, inhalation or oral delivery.

Another aspect provided herein relates to a pharmaceutical composition for the treatment of an antibiotic-resistant bacterial infection, the composition comprising a therapeutically effective amount of a compound of Formula II or stereoisomers, tautomers, or pharmaceutically acceptable salts thereof and a pharmaceutically acceptable carrier;

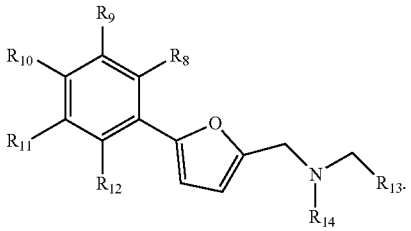

II

Wherein:
$R_8$, $R_9$, $R_{10}$, $R_{11}$, and Ru independently are H, alkyl, aryl, heteroaryl, heteroalkyl, cycloalkyl, heterocyclyl, acyl, allyl, OH, alkoxy, cyano, carboxy, $CF_3$, halide, NH(alkyl), NH(aryl) or $NH_2$; $R_{14}$ and $R_{15}$ are independently H, alkyl, aryl, heteroaryl, heteroalkyl, cycloalkyl, heterocyclyl, acyl, or allyl;

wherein any alkyl, alkenyl, cycloalkyl, heterocyclyl, heteroaryl or aryl is optionally substituted with 1, 2, or 3 groups selected from OH, CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)$alkyl$]_2$, $C(O)NH_2$, COOH, COOMe, acetyl, $(C_1$-$C_8)$alkyl, $O(C_1$-$C_8)$alkyl, $O(C_1$-$C_8)$haloalkyl, $(C_2$-$C_8)$alkenyl, $(C_2$-$C_8)$alkynyl, haloalkyl, thioalkyl, cyanomethylene, alkylaminyl, aryl, heteroaryl, substituted aryl, $NH_2$—C(O)-alkylene, NH(Me)-C(O)-alkylene, $CH_2$—C(O)-lower alkyl, C(O)-lower alkyl, alkylcarbonylaminyl, $CH_2$—[CH(OH)$]_m$—(CH$_2$)$_p$—OH, $CH_2$—[CH(OH)$]_m$—(CH$_2$)$_p$—$NH_2$ or $CH_2$-aryl-alkoxy; or wherein any alkyl, cycloalkyl or heterocyclyl is optionally substituted with oxo; "m" and "p" are independently 1, 2, 3, 4, 5 or 6.

In one embodiment of this aspect and all other aspects provided herein, at least one of $R_8$, $R_9$, $R_{10}$, $R_{11}$, and $R_{12}$ is a chloride or a bromide.

In another embodiment of this aspect and all other aspects provided herein, at least one of $R_8$, $R_9$, $R_{10}$, $R_{11}$, and $R_{12}$ is a methoxy.

In another embodiment of this aspect and all other aspects provided herein, $R_{13}$ is a 5 or 6 member cycloalkyl, heterocyclyl, aryl, or heteroaryl.

In another embodiment of this aspect and all other aspects provided herein, the compound is selected from the following compounds;

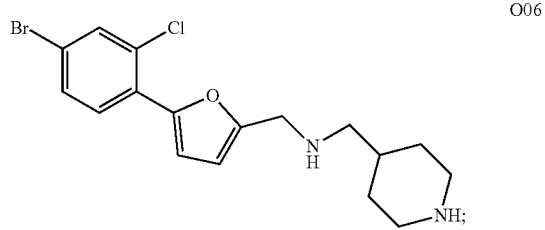

O06

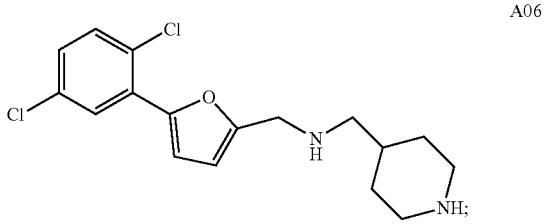

A06

-continued

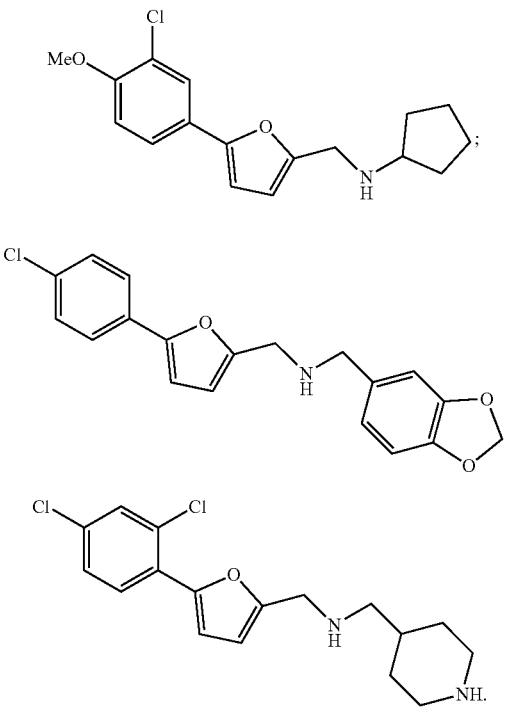

In another embodiment of this aspect and all other aspects provided herein, the compound is compound O06.

In another embodiment of this aspect and all other aspects provided herein, the composition further comprises an effective (or a therapeutically effective) amount of an efflux pump inhibitor.

In another embodiment of this aspect and all other aspects provided herein, the efflux pump inhibitor is phenylalanyl arginyl b-naphthylamide (PAβN).

In another embodiment of this aspect and all other aspects provided herein, the composition is formulated for topical, inhalation, or oral delivery.

Also provided herein, in another aspect, is a pharmaceutical composition for the treatment of an antibiotic-resistant bacterial infection, the composition comprising a therapeutically effective amount of a compound of Formula III or stereoisomers, tautomers, or pharmaceutically acceptable salts thereof and a pharmaceutically acceptable carrier;

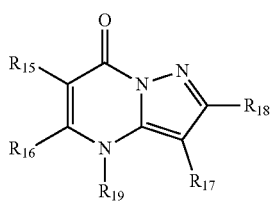

wherein:
$R_{15}$, $R_{16}$, $R_{17}$, and $R_{18}$ independently are H, alkyl, aryl, heteroaryl, heteroalkyl, cycloalkyl, heterocyclyl, acyl, allyl, OH, alkoxy, cyano, carboxy, $CF_3$, halide, NH(alkyl), NH(aryl) or $NH_2$;
$R_{19}$ is H, alkyl, aryl, heteroaryl, heteroalkyl, cycloalkyl, heterocyclyl, acyl, or allyl;

wherein any alkyl, alkenyl, cycloalkyl, heterocyclyl, heteroaryl or aryl is optionally substituted with 1, 2, or 3 groups selected from OH, CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)$alkyl$]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, aryl, heteroaryl, substituted aryl, $NH_2$—C(O)-alkylene, NH(Me)-C(O)-alkylene, $CH_2$—C(O)-lower alkyl, C(O)-lower alkyl, alkylcarbonylaminyl, $CH_2$—[CH(OH)]$_m$—$(CH_2)_p$—OH, $CH_2$—[CH(OH)]$_m$—$(CH_2)_p$—$NH_2$ or $CH_2$-aryl-alkoxy; or wherein any alkyl, cycloalkyl or heterocyclyl is optionally substituted with oxo; "m" and "p" are independently 1, 2, 3, 4, 5 or 6.

In one embodiment of this aspect and all other aspects provided herein, at least one of $R_{15}$ or $R_{16}$ is an aryl group.

In another embodiment of this aspect and all other aspects provided herein, $R_{16}$ a halogenated aryl group.

In another embodiment of this aspect and all other aspects provided herein, at least one of $R_{17}$ or $R_{18}$ is an alkyl group and the other of $R_{17}$ or $R_{18}$ is an aromatic group.

In another embodiment of this aspect and all other aspects provided herein, the compound is selected from the following compounds;

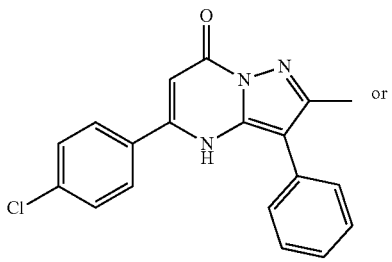

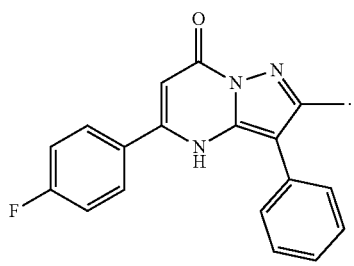

In another embodiment of this aspect and all other aspects provided herein, the compound is compound N08.

Another aspect provided herein relates to a method for treating a bacterial infection in a subject, the method comprising administering a composition comprising a therapeutically effective amount of a compound of Formula I, II or III, in combination with a therapeutically effective amount of a bacterial efflux pump inhibitor to a subject having a bacterial infection, thereby treating the bacterial infection in the subject.

In one embodiment of this aspect and all other aspects provided herein, the bacterial infection comprises an antibiotic-resistant bacterium.

In another embodiment of this aspect and all other aspects provided herein, the compound of: (i) Formula I is C17, (ii) Formula II is O06, or (iii) Formula III is N08.

In another embodiment of this aspect and all other aspects provided herein, the bacterial efflux pump inhibitor is PaβN.

In another embodiment of this aspect and all other aspects provided herein, the antibiotic-resistant bacterium is a Gram negative bacterial strain.

In another embodiment of this aspect and all other aspects provided herein, the Gram negative bacterial strain is a strain from the Enterobacteriaceae family.

In another embodiment of this aspect and all other aspects provided herein, the antibiotic-resistant bacterium comprises a carbapenem-resistant strain of bacteria.

In another embodiment of this aspect and all other aspects provided herein, the antibiotic-resistant bacterium comprises carbapenem-resistant *Klebsiella pneumoniae*, methicillin-resistant *Staphylococcus aureus* (MRSA), carbapenem-resistant *Escherichia coli, Acinetobacter baumanii*, or *Pseudomonas aeruginosa* PA01.

In another embodiment of this aspect and all other aspects provided herein, the subject is a human.

In another embodiment of this aspect and all other aspects provided herein, the compound of Formula I, II or III and/or the bacterial efflux pump inhibitor is administered topically, orally, by inhalation or intravenously.

In another embodiment of this aspect and all other aspects provided herein, the compound of Formula I, II, or III and the bacterial efflux pump inhibitor are administered simultaneously or sequentially.

In another embodiment of this aspect and all other aspects provided herein, the method further comprises a step of diagnosing the subject with the bacterial infection.

Also provided herein, in another aspect, is the use of a composition as described herein in the treatment of a bacterial infection in a subject.

In one embodiment of this aspect and all other aspects provided herein, the composition or treatment further comprises a bacterial efflux pump inhibitor.

In another embodiment of this aspect and all other aspects provided herein, the bacterial infection comprises an antibiotic-resistant bacterium.

BRIEF DESCRIPTION OF THE FIGURES

FIG. 1A, Correlation between bacterial growth measured by optical density ($OD_{655}$) and color change of the medium as a result of bacterial fermentation of mannose ($\Delta A_{615}$). The nadir of the color change occurs at early- to mid-exponential growth and is indicated by the dashed line. FIG. 1B, Representative data from two screen plates with $\Delta A_{615}$ (y-axis) plotted against well location (x-axis). The data provided are from three experimental groups: (i) gentamicin as a positive control, (ii) negative controls (medium with no antimicrobials), and (iii) sample wells that contain unknown compounds. FIG. 1C, Summary of the outcomes from the fungal extract library screened. Patulin was a component of all strong hits. FIG. 1D, The chemical structure of patulin.

FIG. 2A, Summary of the outcomes from the chemical library screen. FIG. 2B, Results numeric of prioritized compounds in the cherry-pick assay. Individual values are shown for primary and cherry pick assays. pH-DM supplemented with 50 µg/mL of gentamicin was used as a positive control, while no compound was added in the negative control. Central dotted lines indicate the average values of the positive and negative controls, while upper and lower dotted lines indicate +/- three standard deviations, respectively. FIG. 2C, Structures of top compounds.

FIG. 6A, Phase-contrast microscopy observation of cell morphology after treatment with compounds. Arrow indicates particulate matter identified in cultures containing compound N08. Ampicillin (Amp, 150 µg/mL) is included as a positive control for altered cell morphology of a peptidoglycan-targeting antibiotic. Untr: untreated cells incubated with medium containing DMSO alone. FIG. 6B, Quantification of the average particle size using images obtained in FIG. 6A. FIG. 6C, Quantification of total area coverage using images obtained in FIG. 6A. Error bars represent the standard deviation. ** p≤0.0001,  p≤0.01, and ns p>0.05 against the untreated (Untr, 0 µg/mL). Ordinary one-way ANOVA followed by Tukey's multiple comparison test was used to calculate significance.

FIG. 7B, compound C17. FIG. 7C, compound N08, and FIG. 7D, gentamicin.

FIG. 9B, Inhibition of fermentation after 22 hours, and FIG. 9C, inhibition of growth after 22 hours. Gentamicin was used as a positive control. The dashed line indicates the average value of the negative control. The gray area indicates three standard deviations above and below the negative control average.

FIG. 12B, Compound C17. FIG. 12C, Compound N08.

DETAILED DESCRIPTION

Figure 1A:
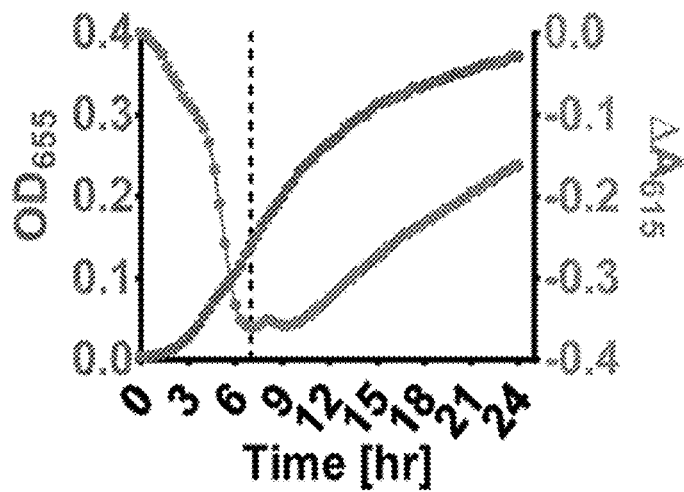
FIGS. 1A-1D. A high-throughput screen based on bacterial fermentation identifies fungal extracts active against multidrug resistant *Klebsiella pneumoniae*. The antibacterial natural product is patulin.

The compositions and methods described herein are related, in part, to the discovery of novel antibiotic agents that are effective in the treatment of bacterial strains that are resistant to one or more conventional antibiotics (e.g., penicillin, carbapenem etc). Thus, provided herein are compositions comprising such novel antibiotic agents for the treatment of a bacterial infection, even a bacterial infection involving an antibiotic resistant bacterium. In certain embodiments, the compositions described herein further comprise a bacterial efflux pump inhibitor that can be used in a method of treating a bacterial infection.

Definitions

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, a "subject" refers to a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. Preferably, the subject is a mammal. The mammal can be a human, non-human primate, mouse, rat, dog, cat, horse, or cow, but is not limited to these examples. Mammals other than humans can be advantageously used as subjects that represent animal models of certain bacterial infections. A human subject can be genetically male or female and of any age (e.g., neonate, infant, baby, toddler, child, pre-teen, adolescent, adult, geriatric etc).

The terms, "individual," "patient" and "subject" are used interchangeably herein.

As used herein, the term "therapeutically effective amount" refers to the amount of an antibiotic agent (in the presence or absence of a bacterial efflux pump inhibitor) that is sufficient to reduce the severity or duration of a bacterial infection, ameliorate one or more symptoms of the infection, prevent the advancement of the infection, or cause regression of bacterial infection. In other embodiments of the compositions and methods described herein, the amount of an antibiotic agent is determined to be "effective" when there is (1) a reduction in mortality associated with a given bacterial infection; (2) a decrease in hospitalization rate, (3) a decrease in number of hospitalizations or lengths of stay, (4) reduced need for supportive medications to address symptoms (e.g., ibuprofen for fever and pain), (5) reduced length of bacterial infection, (6) prevention of secondary diseases/disorders, and (7) improved quality of life.

As used herein, the term "effective amount," when used in reference to an adjunct therapy, such as a bacterial efflux pump inhibitor, refers to the amount of the adjunct therapy that is sufficient to augment the antibiotic efficacy of an antibiotic agent compared to the efficacy of the antibiotic agent when administered alone. An "effective amount" does not require that the adjunct therapy have any antibiotic action on its own. In some embodiments, an "effective amount" of an adjunct therapy will (i) increase the antibacterial efficacy of the antibiotic agent, (ii) permit a lower dose of the antibiotic agent to be used, or (iii) a combination thereof.

As used herein, the term "in combination" in the context of the administration of an antibiotic agent to a subject refers to the use of at least one additional agent (e.g., bacterial efflux pump inhibitor) in a treatment regimen comprising the antibiotic agent. The use of the term "in combination" does not restrict the order in which the agents (e.g., an antibiotic agent or bacterial efflux pump inhibitor) are administered to a subject. An antibiotic agent can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a bacterial efflux pump inhibitor to a subject which had, has, or is at risk of having a bacterial infection comprising one or more antibiotic-resistant strains of bacteria. The agents are administered to a subject in a sequence and within a time interval such that the agents can act together. In a particular embodiment, the agents are administered to a subject in a sequence and within a time interval such that they provide an increased benefit than if they were administered otherwise.

The term "Gram-positive bacteria" as used herein refers to bacteria having peptidoglycan as part of their cell wall structure (as well as polysaccharides and/or teichoic acids) and are characterized by their blue-violet color reaction in a Gram-staining procedure. Representative Gram-positive bacteria include: *Actinomyces* spp., *Bifidobacterium* spp., *Clostridium botulinum*, *Clostridium perfringens*, *Clostridium* spp., *Clostridium tetani*, *Corynebacterium diphtheriae*, *Corynebacterium jeikeium*, *Enterococcus faecalis*, *Enterococcus faecium*, *Erysipelothrix rhusiopathiae*, *Eubacterium* spp., *Gardnerella vaginalis*, *Gemella morbillorum*, *Leuconostoc* spp., *Mycobacterium abscessus*, *Mycobacterium avium* complex, *Mycobacterium chelonae*, *Mycobacterium fortuitum*, *Mycobacterium haemophilium*, *Mycobacterium kansasii*, *Mycobacterium leprae*, *Mycobacterium marinum*, *Mycobacterium scrofulaceum*, *Mycobacterium smegmatis*, *Mycobacterium terse*, *Mycobacterium tuberculosis*, *Mycobacterium ulcerans*, *Nocardia* spp., *Peptococcus niger*, *Peptostreptococcus* spp., *Proprionibacterium* spp., *Sarcina lutea*, *Staphylococcus aureus*, *Staphylococcus auricularis*, *Staphylococcus capitis*, *Staphylococcus cohnii*, *Staphylococcus epidermidis*, *Staphylococcus haemolyticus*, *Staphylococcus hominis*, *Staphylococcus lugdanensis*, *Staphylococcus saccharolyticus*, *Staphylococcus saprophyticus*, *Staphylococcus schleiferi*, *Staphylococcus similans*, *Staphylococcus warneri*, *Staphylococcus xylosus*, *Streptococcus agalactiae* (group B *streptococcus*), *Streptococcus anginosus*, *Streptococcus bovis*, *Streptococcus canis*, *Streptococcus equi*, *Streptococcus milleri*, *Streptococcus mitior*, *Streptococcus mutans*, *Streptococcus pneumoniae*, *Streptococcus pyogenes* (group A *streptococcus*), *Streptococcus salivarius*, or *Streptococcus sanguis*.

The term "Gram-negative bacteria" as used herein refers to bacteria characterized by the presence of a double membrane surrounding each bacterial cell. Representative Gram-negative bacteria include *Acinetobacter calcoaceticus*, *Acinetobacter baumannii*, *Actinobacillus actinomycetemcomitans*, *Aeromonas hydrophile*, *Alcaligenes xylosoxidans*, *Bacteroides*, *Bacteroides fragilis*, *Bartonella bacilliformis*, *Bordetella* spp., *Borrelia burgdorferi*, *Branhamella catarrhalis*, *Brucella* spp., *Campylobacter* spp., *Chlamydia pneumoniae*, *Chlamydia psittaci*, *Chlamydia trachomatis*, *Chromobacterium violaceum*, *Citrobacter* spp., *Eikenella corrodens*, *Enterobacter aerogenes*, *Escherichia coli*, *Flavobacterium meningosepticum*, *Fusobacterium* spp., *Haemophilus influenzae*, *Haemophilus* spp., *Helicobacter pylori*, *Klebsiella pneumoniae*, *Klebsiella* spp., *Legionella* spp., *Leptospira* spp., *Moraxella catarrhalis*, *Morganella morganii*, *Mycoplasma pneumoniae*, *Neisseria gonorrhoeae*, *Neisseria meningitidis*, *Pasteurella multocida*, *Plesiomonas shigelloides*, *Prevotella* spp., *Proteus* spp., *Providencia rettgeri*, *Pseudomonas aeruginosa*, *Pseudomonas* spp., *Rickettsia prowazekii*, *Rickettsia rickettsii*, *Rochalimaea* spp., *Salmonella* spp., *Salmonella typhi*, *Serratia marcescens*, *Shigella* spp., *Shigella sonnei*, *Treponema carateum*, *Treponema pallidum*, *Treponema pallidum endemicum*, *Treponema pertenue*, *Veillonella* spp., *Vibrio cholerae*, *Vibrio vulnificus*, *Yersinia enterocolitica*, and *Yersinia pestis*.

The terms "decrease", "reduced", "reduction", or "inhibit" are all used herein to mean a decrease or lessening of a property, level, or other parameter by a statistically significant amount. In some embodiments, "reduce," "reduction" or "decrease" or "inhibit" typically means a decrease by at least 10% as compared to a reference level and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level.

The terms "increased", "increase" or "enhance" or "activate" are all used herein to generally mean an increase of a property, level, or other parameter by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Bacterial Infections and Antibiotic Resistance in Bacteria

Bacterial strains that are resistant to multiple antibiotics are now widespread and bacteria as a whole have developed at least one mechanism of resistance (and frequently many more) to every single antibiotic class. For example, Methicillin-resistant *Staphylococcus aureus* (MRSA) is one of the principal multi-drug resistant bacterial pathogens causing serious community and hospital-acquired infections, such as skin and soft tissue infections, bone, joint and implant infections, ventilator-associated pneumonia, and sepsis. It is estimated that multi-drug resistant *Staphylococcus aureus* infections leads to 19,000 deaths per year in the United States. Despite this high mortality rate, there are relatively few new antibacterial agents in the pharmaceutical pipeline. Instead, the majority of antibiotics developed in the last decade are molecules re-engineered from existing antibiotic classes for which underlying resistance mechanisms are already present. Therefore, effective new therapeutic options for treatment of infections caused, particularly those caused by multi-drug resistant bacteria are urgently needed.

Provided herein are novel antibiotic agents and compositions that can be used to treat a variety of bacterial infections, including infections comprising antibiotic-resistant strains of bacteria. As used herein, the term "antibiotic-resistant" refers to a bacterium that is insensitive to at least one conventional antibiotic (e.g., penicillins, carbapenems, etc) by one or more mechanisms, such as biofilm formation or presence of an efflux pump.

It should be noted that the antibiotic agents and compositions described herein can be used in the treatment of any bacterial infection, however the compositions described herein have increased utility in bacterial infections that are resistant to one or more conventional antibiotics. That is, the compositions described herein (and methods thereof) provide treatments for bacterial infections that were previously untreatable due to their resistance to conventional antibiotics (i.e., an antibiotic that is approved for, or routinely prescribed to treat a given bacterial infection).

In some embodiments, the bacterium to be treated with a novel antibiotic agent as described herein is a gram positive species. As used herein, the term "antibiotic agent" refers to an agent (e.g., a small molecule or compound) identified as having antibiotic properties in the whole cell bacterial assay described in the Example section. In particular, the term "antibiotic agent" refers to compounds of Formula I, II, or III, as described herein. For the avoidance of doubt, the term "antibiotic agent" used throughout the specification is not intended to encompass conventional antibiotics that are currently approved for, or are routinely prescribed for bacterial infections (e.g., penicillins, tetracyclines, cephalosporins, quinolones, lincomycins, macrolides, sulfonamides, glycopeptides, aminoglycosides, carbapenems, and the like).

In some embodiments, the bacterium is a gram negative species. In certain embodiments, the bacterial infection to be treated as described herein comprises infection with a bacterium comprising one or more bacterial efflux pumps.

In some embodiments, the bacterium to be treated with the antibiotic agents described herein exhibits non-specific resistance to antibiotics, for example, by the formation of biofilms. In some embodiments, the bacterium exhibits specific resistance to particular antibiotics (e.g., carbapenem or methicillin). The specific resistance in the bacteria can be either innate or acquired. In some embodiments, the bacterium exhibits both specific and non-specific resistance to one or more antibiotics.

In some embodiments, the bacterium is *Staphylococcus aureus*. In particular embodiments, the *S. aureus* is a methicillin resistant species (MRSA).

In some embodiments, the bacterium is *Enterococcus faecium*. In some embodiments, the *E. faecium* is a vancomycin-resistant species. In other embodiments, the *E. faecium* is a teicoplanin-resistant species. In some embodiments, the *E. faecium* is a vancomycin- and teicoplanin-resistant species. In some embodiments, the *E. faecium* is resistant to the tetracycline group of antibiotics.

In some embodiments, the bacterium is *Klebsiella pneumoniae*. In some embodiments, the *K pneumonia* is an antibiotic resistant species. In particular embodiments, the *K. pneumoniae* is resistant to the penicillin group of antibiotics. In particular embodiments, the *K. pneumoniae* is resistant to the cephalosporin group of antibiotics. In particular embodiments, the *K. pneumoniae* is resistant to the carbapenem group of antibiotics. In particular embodiments, the *K. pneumoniae* is resistant to the fluoroquinolone group of antibiotics. In particular embodiments, the *K. pneumoniae* is resistant to protein synthesis inhibitor antibiotics. In particular embodiments, the *K. pneumoniae* is resistant to ampicillin, aztreonam, cefoxitin, cefpodoxime, ceftazidime, chloramphenicol, piperacillin, and tetracycline. In particular embodiments, the *K. pneumoniae* is resistant to carbapenem-imipenem and ertapenem, amikacin, aztreonam, levofloxacin, and ciprofloxacin.

In some embodiments, the bacterium to be treated with the methods and compositions described herein is *Pseudomonas aeruginosa*. In other embodiments, the bacterium is *Pseudomonas aeruginosa* PA01.

In some embodiments, the bacterium to be treated with the methods and compositions described herein is *Escherichia coli*. In other embodiments, the bacterium is carbapenem-resistant *Escherichia coli*.

Essentially any bacterial infection can be treated using the compositions and methods described herein. Such bacterial infections are known in the art and are not described in detail herein. Non-limiting examples of bacterial infections include: bacterial meningitis, otitis media, sepsis, pneumonia, tuberculosis, upper respiratory tract infections, gastritis, food poisoning, eye infections, sinusitis, urinary tract infections, skin infections and sexually transmitted diseases.

In some embodiments of the methods described herein, the subject to be treated with the antibiotic agent or composition thereof is first diagnosed as having a given bacterial infection. Methods for detecting and identifying a bacterial infection and/or a bacterium responsible for a given bacterial infection are known to those of skill in the art. For example, bacterial pneumonia can be detected by assessing symptoms such as persistent cough, fever, stomach ache, or difficulty breathing in a physical exam or by chest x-ray. In some embodiments, one or more of the following cultures can be used to detect and identify a bacterial infection: a urine culture, a sputum culture, a blood culture, a stool culture, a wound culture, a throat culture, mucosal swab, fluid/pus aspiration, skin biopsy, or the like.

Antibiotic Agents and Compounds

Provided herein are novel antibiotic agents and compounds that were initially discovered by way of a whole cell bacterial assay using carbapenem-resistant *Klebsiella pneumoniae*. Such agents show antibiotic efficacy in bacteria that are resistant to one or more conventional antibiotics (i.e., antibiotics that are already in use for treatment of bacterial infections, or are used in the raising of animals for food).

In a first aspect the disclosure is a pharmaceutical composition for the treatment of an antibiotic-resistant bacterial infection, the composition comprising a therapeutically effective amount of a compound of Formula I, II or III; or stereoisomers, tautomers, or pharmaceutically acceptable salts thereof; and a pharmaceutically acceptable carrier:

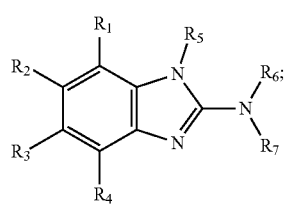

I

-continued

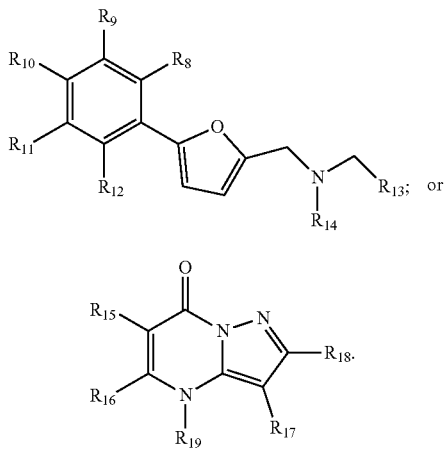

II

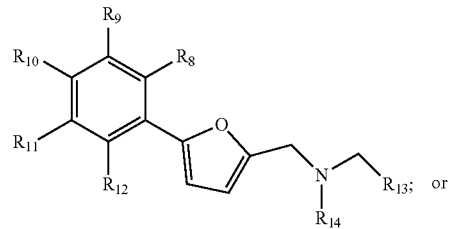

III

Wherein in Formula I: $R_1$, $R_2$, $R_3$, and $R_4$ independently are H, alkyl, aryl, heteroaryl, heteroalkyl, cycloalkyl, heterocyclyl, acyl, allyl, OH, alkoxy, cyano, carboxy, $CF_3$, halide, NH(alkyl), NH(aryl) or $NH_2$; $R_5$ is H, alkyl, aryl, heteroaryl, heteroalkyl, cycloalkyl, heterocyclyl, acyl, or allyl; $R_6$ and $R_7$ are independently H, alkyl, aryl, heteroaryl, heteroalkyl, cycloalkyl, heterocyclyl, acyl, or allyl; or $R_6$ and $R_7$ together with the nitrogen they are bonded to form a heterocyclyl or a heteroaryl. Wherein in Formula II: $R_8$, $R_9$, $R_{10}$, $R_{11}$, and $R_{12}$ independently are H, alkyl, aryl, heteroaryl, heteroalkyl, cycloalkyl, heterocyclyl, acyl, allyl, OH, alkoxy, cyano, carboxy, $CF_3$, halide, NH(alkyl), NH(aryl) or $NH_2$; $R_{14}$ and $R_{15}$ are independently H, alkyl, aryl, heteroaryl, heteroalkyl, cycloalkyl, heterocyclyl, acyl, or allyl. Wherein in Formula III: $R_{15}$, $R_{16}$, $R_{17}$, and $R_{18}$ independently are H, alkyl, aryl, heteroaryl, heteroalkyl, cycloalkyl, heterocyclyl, acyl, allyl, OH, alkoxy, cyano, carboxy, $CF_3$, halide, NH(alkyl), NH(aryl) or $NH_2$; $R_{19}$ is H, alkyl, aryl, heteroaryl, heteroalkyl, cycloalkyl, heterocyclyl, acyl, or allyl. Wherein in Formula I, II and III, any alkyl, alkenyl, cycloalkyl, heterocyclyl, heteroaryl or aryl is optionally substituted with 1, 2, or 3 groups selected from OH, CN, SH, $SO_2NH_2$, $SO_2(C_1-C_4)$alkyl, $SO_2NH(C_1-C_4)$alkyl, halogen, $NH_2$, $NH(C_1-C_4)$alkyl, $N[(C_1-C_4)alkyl]_2$, $C(O)NH_2$, COOH, COOMe, acetyl, $(C_1-C_8)$alkyl, $O(C_1-C_8)$alkyl, $O(C_1-C_8)$haloalkyl, $(C_2-C_8)$alkenyl, $(C_2-C_8)$alkynyl, haloalkyl, thioalkyl, cyanomethylene, alkylaminyl, aryl, heteroaryl, substituted aryl, $NH_2$—C(O)-alkylene, NH(Me)-C(O)-alkylene, $CH_2$—C(O)-lower alkyl, C(O)-lower alkyl, alkylcarbonylaminyl, $CH_2$—[CH(OH)]$_n$—$(CH_2)_p$—OH, $CH_2$—[CH(OH)]$_m$—$(CH_2)_p$—$NH_2$ or $CH_2$-aryl-alkoxy; or wherein any alkyl, cycloalkyl or heterocyclyl is optionally substituted with oxo; "m" and "p" are independently 1, 2, 3, 4, 5 or 6.

The above summary is not intended to represent every embodiment or every aspect of the present disclosure. Rather, the foregoing summary merely provides an example of some of the novel aspects and features set forth herein. The above features and advantages, and other features and advantages of the present disclosure, will be readily apparent from the following detailed description of representative embodiments and modes for carrying out the present invention, when taken in connection with the accompanying drawings and the appended claims.

In some embodiments the disclosure relates to pharmaceutical compositions comprising a therapeutically effective amount of a compound of Formula I, II or III; or stereoisomers, tautomers, or pharmaceutically acceptable salts thereof; and a pharmaceutically acceptable carrier:

I

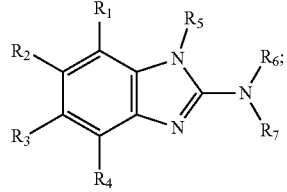

II

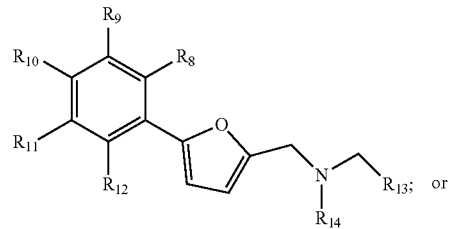

III

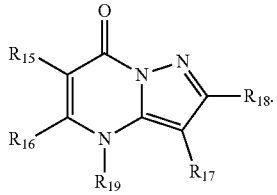

In some embodiments of Formula I, $R_1$, $R_2$, $R_3$, and $R_4$ independently are H, alkyl, aryl, heteroaryl, heteroalkyl, cycloalkyl, heterocyclyl, acyl, allyl, OH, alkoxy, cyano, carboxy, $CF_3$, halide, NH(alkyl), NH(aryl) or $NH_2$, each of which can be optionally substituted; $R_5$ is H, alkyl, aryl, heteroaryl, heteroalkyl, cycloalkyl, heterocyclyl, acyl, or allyl, each of which can be optionally substituted; $R_6$ and $R_7$ are independently H, alkyl, aryl, heteroaryl, heteroalkyl, cycloalkyl, heterocyclyl, acyl, or allyl, each of which can be optionally substituted; or $R_6$ and $R_7$ together with the nitrogen they are bonded to form an optionally substituted heterocyclyl or a heteroaryl.

In some compounds of Formula I, $R_1$ can be H, $C_1-C_6$alkyl, 3-12 membered aryl, 3-12 membered heteroaryl, 3-12 membered cycloalkyl, 3-12 membered heterocyclyl, acyl, OH, $C_1-C_6$alkoxy, CN, $CF_3$, halide, $NH(C_1-C_6$alkyl), NH(3-12 membered aryl) or $NH_2$, each of which can be optionally substituted. For example, $R_1$ can be H, $C_1-C_6$alkyl, acyl, OH, $C_1-C_6$alkoxy, CN, $CF_3$, halide, $NH(C_1-C_6$alkyl), or $NH_2$, each of which can be optionally substituted. In some compounds of Formula I, $R_1$ is H, OH, $CF_3$, CN, $NH_2$, Cl, F, I or Br. Preferably, $R_1$ is H.

In some compounds of Formula I, $R_2$ can be H, $C_1-C_6$alkyl, 3-12 membered aryl, 3-12 membered heteroaryl, 3-12 membered cycloalkyl, 3-12 membered heterocyclyl, acyl, OH, $C_1-C_6$alkoxy, CN, $CF_3$, halide, $NH(C_1-C_6$alkyl), NH(3-12 membered aryl) or $NH_2$, each of which can be optionally substituted. For example, $R_2$ can be H, $C_1-C_6$alkyl, acyl, OH, $C_1-C_6$alkoxy, CN, $CF_3$, halide, $NH(C_1-C_6$alkyl), or $NH_2$, each of which can be optionally substituted. In some compounds of Formula I, $R_2$ is H, OH, $CF_3$, CN, $NH_2$, Cl, F, I or Br. Preferably, $R_2$ is H.

In some compounds of Formula I, $R_3$ can be H, $C_1-C_6$alkyl, 3-12 membered aryl, 3-12 membered heteroaryl, 3-12 membered cycloalkyl, 3-12 membered heterocyclyl, acyl, OH, $C_1$-$C_6$alkoxy, CN, $CF_3$, halide, $NH(C_1$-$C_6$alkyl), NH(3-12 membered aryl) or $NH_2$, each of which can be optionally substituted. For example, $R_3$ can be H, $C_1$-$C_6$alkyl, acyl, OH, $C_1$-$C_6$alkoxy, CN, $CF_3$, halide, $NH(C_1$-$C_6$alkyl), or $NH_2$, each of which can be optionally substituted. In some compounds of Formula I, $R_3$ is H, OH, $CF_3$, CN, $NH_2$, Cl, F, I or Br. Preferably, $R_3$ is H.

In some compounds of Formula I, $R_4$ can be H, $C_1$-$C_6$alkyl, 3-12 membered aryl, 3-12 membered heteroaryl, 3-12 membered cycloalkyl, 3-12 membered heterocyclyl, acyl, OH, $C_1$-$C_6$alkoxy, CN, $CF_3$, halide, $NH(C_1$-$C_6$alkyl), NH(3-12 membered aryl) or $NH_2$, each of which can be optionally substituted. For example, $R_4$ can be H, $C_1$-$C_6$alkyl, acyl, OH, $C_1$-$C_6$alkoxy, CN, $CF_3$, halide, $NH(C_1$-$C_6$alkyl), or $NH_2$, each of which can be optionally substituted. In some compounds of Formula I, $R_4$ is H, OH, $CF_3$, CN, $NH_2$, Cl, F, I or Br. Preferably, $R_4$ is H.

In some compounds of Formula I, $R_1$, $R_2$, $R_3$ and $R_4$ are selected independently from the group consisting of H, $C_1$-$C_6$alkyl, 3-12 membered aryl, 3-12 membered heteroaryl, 3-12 membered cycloalkyl, 3-12 membered heterocyclyl, acyl, OH, $C_1$-$C_6$alkoxy, CN, $CF_3$, halide, $NH(C_1$-$C_6$alkyl), NH(3-12 membered aryl) and $NH_2$, each of which can be optionally substituted. For example, $R_1$, $R_2$, $R_3$ and $R_4$ can be selected independently from the group consisting of H, $C_1$-$C_6$alkyl, acyl, OH, $C_1$-$C_6$alkoxy, CN, $CF_3$, halide, $NH(C_1$-$C_6$alkyl), and $NH_2$, each of which can be optionally substituted. In some compounds of Formula I, $R_1$, $R_2$, $R_3$ and $R_4$ are selected independently from the group consisting of H, OH, $CF_3$, CN, $NH_2$, Cl, F, I and Br. In some embodiments at least one, at least two, at least three, or all of $R_1$, $R_2$, $R_3$, and $R_4$ are H. In some embodiments at least one of $R_1$, $R_2$, $R_3$, and $R_4$ is $NH_2$.

It is noted that $R_1$, $R_2$, $R_3$ and $R_4$ all can be same, all different, or some same and some different. For example, at least two, at least three or all four of $R_1$, $R_2$, $R_3$ and $R_4$ can be same. In another non-limiting example, at least two, at least three or all four of $R_1$, $R_2$, $R_3$ and $R_4$ can be different.

In some compounds of Formula I, $R_5$ can be H, $C_1$-$C_6$alkyl, 3-12 membered aryl, 3-12 membered heteroaryl, 3-12 membered cycloalkyl, 3-12 membered heterocyclyl, or acyl, each of which can be optionally substituted. For example, $R_5$ can be H, $C_1$-$C_6$alkyl or acyl, each of which can be optionally substituted. In some compounds of Formula I, $R_5$ is H or an optionally substituted $C_1$-$C_6$alkyl. In some embodiments, $R_5$ is H.

In some other embodiments, $R_5$ is a $C_1$-$C_6$alkyl substituted with one substituent, e.g. a substituent selected from the group consisting of OH, CN, SH, halogen, $NH_2$, $NH(C_1$-$C_4)$alkyl, $N[(C_1$-$C_4)$alkyl$]_2$, $C(O)NH_2$, COOH, or COOMe. For example, $R_5$ is a $C_1$-$C_6$alkyl substituted with a $N[(C_1$-$C_4)$alkyl$]_2$ group on the terminal carbon, e.g., $R_5$ is a linear $C_1$-$C_6$alkyl where the terminal carbon is substituted with $N[(C_1$-$C_4)$alkyl$]_2$. In some embodiments, $R_5$ is 2-(diethylamino)ethyl.

In some compounds of Formula I, $R_6$ can be H, $C_1$-$C_6$alkyl, 3-12 membered aryl, 3-12 membered heteroaryl, 3-12 membered cycloalkyl, 3-12 membered heterocyclyl, or acyl, each of which can be optionally substituted. For example, $R_6$ can be H, $C_1$-$C_6$alkyl, or acyl, each of which can be optionally substituted. In some compounds of Formula I, $R_6$ is H or a $C_1$-$C_6$alkyl optionally substituted with a 3-12 membered aryl or heteroaryl, where the aryl or heteroaryl can be optionally substituted. For example, $R_6$ is H or a $C_1$-$C_6$alkyl substituted with an optionally substituted 3-12 membered aryl. Exemplary alkyls include, but are not limited to, methyl, ethyl, propyl, isopropyl, 1-methylpropyl, 2-methylpropyl, butyl, and t-butyl, each of which can be optionally substituted. Exemplary aryls include, but are not limited to, phenyl, naphthyl, anthracenyl, indolyl, isoindolyl, benzothienyl, benzofuranyl, dibenzofuranyl, indazolyl, benzimidazolyl, benzthiazolyl, quinolyl, isoquinolyl, quinolinyl, phthalazinyl, quinazolinyl, quinoxalinyl, carbazolyl, acridinyl, phenazinyl, phenothiazinyl, phenoxazinyl, tetrahydroquinolinyl, tetrahydroisoquinolinyl, fluorenyl, indanyl, phenanthridinyl, tetrahydronaphthyl, indolinyl, phenoxazinyl, benzodioxanyl, and benzodioxolyl, each of which can be optionally substituted. In some embodiments, $R_6$ is H. In some other embodiments, $R_6$ is 4-(diethylamino)benzylmethyl.

In some compounds of Formula I, $R_7$ can be H, $C_1$-$C_6$alkyl, 3-12 membered aryl, 3-12 membered heteroaryl, 3-12 membered cycloalkyl, 3-12 membered heterocyclyl, or acyl, each of which can be optionally substituted. For example, $R_7$ can be H, $C_1$-$C_6$alkyl, or acyl, each of which can be optionally substituted. In some compounds of Formula I, $R_7$ is H or a $C_1$-$C_6$alkyl optionally substituted with a 3-12 membered aryl or heteroaryl, where the aryl or heteroaryl can be optionally substituted. For example, $R_7$ is H or a $C_1$-$C_6$alkyl substituted with an optionally substituted 3-12 membered aryl. Exemplary alkyls include, but are not limited to, methyl, ethyl, propyl, isopropyl, 1-methylpropyl, 2-methylpropyl, butyl, and t-butyl, each of which can be optionally substituted. Exemplary aryls include, but are not limited to, phenyl, naphthyl, anthracenyl, indolyl, isoindolyl, benzothienyl, benzofuranyl, dibenzofuranyl, indazolyl, benzimidazolyl, benzthiazolyl, quinolyl, isoquinolyl, quinolinyl, phthalazinyl, quinazolinyl, quinoxalinyl, carbazolyl, acridinyl, phenazinyl, phenothiazinyl, phenoxazinyl, tetrahydroquinolinyl, tetrahydroisoquinolinyl, fluorenyl, indanyl, phenanthridinyl, tetrahydronaphthyl, indolinyl, phenoxazinyl, benzodioxanyl, and benzodioxolyl, each of which can be optionally substituted. In some embodiments, $R_7$ is H. In some other embodiments, $R_7$ is 4-(diethylamino)benzylmethyl.

It is noted that $R_6$ and $R_7$ can be same or different. Preferably, $R_6$ and $R_7$ are different. For example, $R_6$ and $R_7$ can be selected independently from the group consisting of H, $C_1$-$C_6$alkyl, 3-12 membered aryl, 3-12 membered heteroaryl, 3-12 membered cycloalkyl, 3-12 membered heterocyclyl, or acyl, each of which can be optionally substituted. In some embodiments, $R_6$ and $R_7$ can be independently H, $C_1$-$C_6$alkyl, or acyl, each of which can be optionally substituted. In some compounds of Formula I, $R_6$ and $R_7$ are independently H or a $C_1$-$C_6$alkyl optionally substituted with a 3-12 membered aryl or heteroaryl, where the aryl or heteroaryl can be optionally substituted. For example, $R_6$ and $R_7$ are independently H or a $C_1$-$C_6$alkyl substituted with an optionally substituted 3-12 membered aryl.

In some embodiments, one of $R_6$ and $R_7$ is H and the other is a methyl substituted with an aryl group. For example, in some embodiments, $R_6$ is H and $R_7$ is the para-(diethyl amino) benzyl substituted methyl group fragment A:

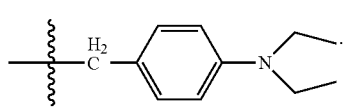

(A)

In some embodiments the compound is compound of Formula I is N09, having the structure:

(NO9)

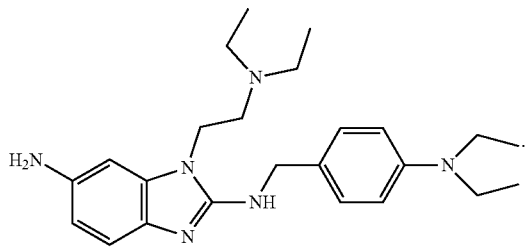

In some compounds of Formula I, $R_6$ and $R_7$ together with the nitrogen they are bonded to can form an optionally substituted 3-12 membered heterocyclyl. Exemplary heterocyclyls include, but are not limited to, aziridine, oxirane, thiiarne, diazridine, oxaziridine, dioxirane, azetidine, oxetane, thietane, diazetidine, dioxetane, dithietane, -pyrrolidine, tetrahydrofuran, tetrahydrothiophene, imidazolidine, pyrazolidine, oxazolidine, isoxazolidine, thiazolidine, isothiazolidine, dioxalane, dithiolane, piperidine, tetrahydropyran, thiane, piperazine, morpholine, thiomorpholine, dioxane, dithiane, hexahydro-1,3,5-triazine, trioxane, trithiane, azepane, oxepane, thiepane, diazepane, azocane, oxocane, thiocane, azonane, oxonane, and thionane, each of which can be optionally substituted.

In some embodiments, $R_6$ and $R_7$ together with the nitrogen they are bonded to form an optionally substituted oxo-pyrazole. For example, $R_6$ and $R_7$ together with the nitrogen they are bonded to form an optionally substituted oxo-pyrazole, wherein $R_6$ is N and $R_7$ is an oxo group bonded to a carbon. In some embodiments, the compound has structure IV:

IV

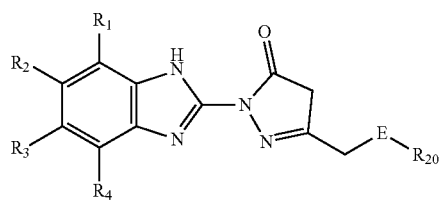

wherein E is oxygen or sulfur and $R_{20}$ is H, alkyl, aryl, heteroaryl heteroalkyl, cycloalkyl, heterocyclyl, acyl, or allyl, each of which can be optionally substituted.

In some compounds of Formula IV, E is S.

In some compounds of Formula IV, $R_{20}$ can be selected from the group consisting of H, $C_1$-$C_6$alkyl, 3-12 membered aryl, 3-12 membered heteroaryl, 3-12 membered cycloalkyl, and 3-12 membered heterocyclyl, each of which can be optionally substituted. In some embodiments, $R_{20}$ is an optionally substituted 3-12 membered aryl or an optionally substituted 3-12 membered heteroaryl. For example, $R_{20}$ is an optionally substituted 3-12 membered heteroaryl. Exemplary heteroaryls include, but are not limited to, azirine, oxirene, phosphoirene, thiirene, diazirine, azete, oxete, thiete, diazete, dioxete, dithiete, pyrrol, furan, thiophene, imidazole, pyrazole, oxazole, isoxazole, thiazole, isothiazole, triazole, furazan, oxadiaxole, thiadiaxole, dioxazole, dithiazole, tetrazole, oxatetrazole, thiatetrazole, pentazole, pyridine, pyran, thiopyran, diazine, oxazine, thiazine, dioxine, dithiin, triazine, tetrazine, pentazine, azepine, oxepine, thiepine, diazepine, thiazepine, azocine, oxocine, thiocine, azonine, oxonine, and thionine, each of which can be optionally substituted. In some embodiments, $R_{20}$ an optionally substituted thiadazole, e.g., 1,2,3-thiazole, 1,2,4-thiazole, 1,2,5-thiazole, or 1,3,4-thiazole, each of which can be optionally substituted. In some embodiments, $R_{20}$ is a 1,3,4-thiazole substituted with a $C_1$-$C_6$alkyl group. For example, $R_{20}$ is a 1,3,4-thiazole substituted with a methyl, ethyl, propyl, isopropyl, 1-methylpropyl, 2-methylpropyl, butyl, t-butyl, pentyl or hexyl. In some embodiments, $R_{20}$ is 2-methyl-1,3,4-thiazol-5-yl.

For example, in some embodiments the compound is compound C17 having the structure:

(C17)

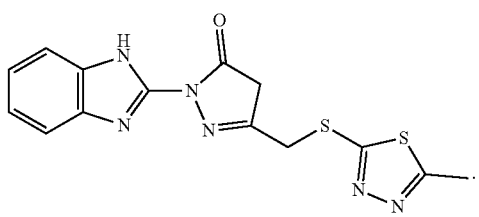

In some embodiments of Formula II, $R_8$, $R_9$, $R_{10}$, $R_{11}$, and Ru independently are H, alkyl, aryl, heteroaryl, heteroalkyl, cycloalkyl, heterocyclyl, acyl, allyl, OH, alkoxy, cyano, carboxy, $CF_3$, halide, NH(alkyl), NH(aryl) or $NH_2$, each of which can be optionally substituted; $R_{13}$ and $R_{14}$ are independently H, alkyl, aryl, heteroaryl, heteroalkyl, cycloalkyl, heterocyclyl, acyl, or allyl, each of which can be optionally substituted; or $R_{13}$ and $R_{14}$ together with the nitrogen they are bonded to form an optionally substituted heterocyclyl or a heteroaryl.

In some embodiments of Formula II, $R_8$, $R_9$, $R_{10}$, $R_{11}$ and $R_{12}$ independently are H, alkyl, aryl, heteroaryl, heteroalkyl, cycloalkyl, heterocyclyl, acyl, allyl, OH, alkoxy, cyano, carboxy, $CF_3$, halide, NH(alkyl), NH(aryl) or $NH_2$, each of which can be optionally substituted; $R_{13}$ and $R_{14}$ are independently H, alkyl, aryl, heteroaryl, heteroalkyl, cycloalkyl, heterocyclyl, acyl, or allyl, each of which can be optionally substituted.

In some compounds of Formula II, $R_8$ can be H, $C_1$-$C_6$alkyl, 3-12 membered aryl, 3-12 membered heteroaryl, 3-12 membered cycloalkyl, 3-12 membered heterocyclyl, acyl, OH, $C_1$-$C_6$alkoxy, CN, $CF_3$, halide, NH($C_1$-$C_6$alkyl), NH(3-12 membered aryl) or $NH_2$, each of which can be optionally substituted. For example, $R_8$ can be H, $C_1$-$C_6$alkyl, acyl, OH, $C_1$-$C_6$alkoxy, CN, $CF_3$, halide, NH($C_1$-$C_6$alkyl), or $NH_2$, each of which can be optionally substituted. In some compounds of Formula II, $R_8$ is H, OH, $CF_3$, CN, $NH_2$, Cl, F, I or Br. Preferably, $R_1$ is H or Cl.

In some compounds of Formula II, $R_9$ can be H, $C_1$-$C_6$alkyl, 3-12 membered aryl, 3-12 membered heteroaryl, 3-12 membered cycloalkyl, 3-12 membered heterocyclyl, acyl, OH, $C_1$-$C_6$alkoxy, CN, $CF_3$, halide, NH($C_1$-$C_6$alkyl), NH(3-12 membered aryl) or $NH_2$, each of which can be optionally substituted. For example, $R_9$ can be H, $C_1$-$C_6$alkyl, acyl, OH, $C_1$-$C_6$alkoxy, CN, $CF_3$, halide, NH($C_1$-$C_6$alkyl), or $NH_2$, each of which can be optionally substituted. In some compounds of Formula II, $R_9$ is H, OH, $CF_3$, CN, $NH_2$, Cl, F, I or Br. Preferably, $R_9$ is H or Cl.

In some compounds of Formula II, $R_{10}$ can be H, $C_1$-$C_6$alkyl, 3-12 membered aryl, 3-12 membered heteroaryl, 3-12 membered cycloalkyl, 3-12 membered heterocyclyl, acyl, OH, $C_1$-$C_6$alkoxy, CN, $CF_3$, halide, NH($C_1$-$C_6$alkyl), NH(3-12 membered aryl) or $NH_2$, each of which can be optionally substituted. For example, $R_{10}$ can be H, $C_1$-$C_6$alkyl, acyl, OH, $C_1$-$C_6$alkoxy, CN, $CF_3$, halide, NH($C_1$-$C_6$alkyl), or $NH_2$, each of which can be optionally substituted. In some compounds of Formula II, $R_{10}$ is H, OH, OMe, $CF_3$, CN, $NH_2$, Cl, F, I or Br. Preferably, $R_2$ is H, Cl or OMe.

In some compounds of Formula II, $R_{11}$ can be H, $C_1$-$C_6$alkyl, 3-12 membered aryl, 3-12 membered heteroaryl, 3-12 membered cycloalkyl, 3-12 membered heterocyclyl, acyl, OH, $C_1$-$C_6$alkoxy, CN, $CF_3$, halide, NH($C_1$-$C_6$alkyl), NH(3-12 membered aryl) or $NH_2$, each of which can be optionally substituted. For example, $R_{11}$ can be H, $C_1$-$C_6$alkyl, acyl, OH, $C_1$-$C_6$alkoxy, CN, $CF_3$, halide, NH($C_1$-$C_6$alkyl), or $NH_2$, each of which can be optionally substituted. In some compounds of Formula II, $R_{11}$ is H, OH, $CF_3$, CN, $NH_2$, Cl, F, I or Br. Preferably, $R_{11}$ is H or Cl.

In some compounds of Formula II, $R_{12}$ can be H, $C_1$-$C_6$alkyl, 3-12 membered aryl, 3-12 membered heteroaryl, 3-12 membered cycloalkyl, 3-12 membered heterocyclyl, acyl, OH, $C_1$-$C_6$alkoxy, CN, $CF_3$, halide, NH($C_1$-$C_6$alkyl), NH(3-12 membered aryl) or $NH_2$, each of which can be optionally substituted. For example, $R_{12}$ can be H, $C_1$-$C_6$alkyl, acyl, OH, $C_1$-$C_6$alkoxy, CN, $CF_3$, halide, NH($C_1$-$C_6$alkyl), or $NH_2$, each of which can be optionally substituted. In some compounds of Formula II, $R_{11}$ is H, OH, $CF_3$, CN, $NH_2$, Cl, F, I or Br. Preferably, $R_{12}$ is H or Cl.

In some compounds of Formula II, $R_8$, $R_9$, $R_{10}$, $R_{11}$ and $R_{12}$ are selected independently from the group consisting of H, $C_1$-$C_6$alkyl, 3-12 membered aryl, 3-12 membered heteroaryl, 3-12 membered cycloalkyl, 3-12 membered heterocyclyl, acyl, OH, $C_1$-$C_6$alkoxy, CN, $CF_3$, halide, NH($C_1$-$C_6$alkyl), NH(3-12 membered aryl) and $NH_2$, each of which can be optionally substituted. For example, $R_8$, $R_9$, $R_{10}$, $R_{11}$ and $R_{12}$ can be selected independently from the group consisting of H, $C_1$-$C_6$alkyl, acyl, OH, $C_1$-$C_6$alkoxy, CN, $CF_3$, halide, NH($C_1$-$C_6$alkyl), and $NH_2$, each of which can be optionally substituted. In some compounds of Formula II, $R_8$, $R_9$, $R_{10}$, $R_{11}$ and $R_{12}$ are selected independently from the group consisting of H, OH, OMe, $CF_3$, CN, $NH_2$, Cl, F, I and Br. In some embodiments at least one of $R_8$, $R_9$, $R_{10}$, $R_{11}$ and $R_{12}$ is a halide, e.g., Cl, F, I or Br. In some embodiments, at least one of $R_8$, $R_9$, $R_{10}$, $R_{11}$ and $R_{12}$ is a $C_1$-$C_6$alkoxy, e.g., methoxy or ethoxy. In some embodiments at least one of $R_8$, $R_9$, $R_{10}$, $R_{11}$ and $R_{12}$ is a halide, e.g., Cl, F, I or Br and at least one of $R_8$, $R_9$, $R_{10}$, $R_{11}$ and $R_{12}$ is a $C_1$-$C_6$alkoxy, e.g., methoxy or ethoxy.

It is noted that $R_8$, $R_9$, $R_{10}$, $R_{11}$ and $R_{12}$ all can be same, all different, or some same and some different. For example, at least two, at least three, at least four, or all five of $R_8$, $R_9$, $R_{10}$, $R_{11}$ and $R_{12}$ can be same. In another non-limiting example, at least two, at least three, at least four, or all five of $R_8$, $R_9$, $R_{10}$, $R_{11}$ and $R_{12}$ can be different.

In some compounds of Formula II, $R_{13}$ can be H, $C_1$-$C_6$alkyl, 3-12 membered aryl, 3-12 membered heteroaryl, 3-12 membered cycloalkyl, 3-12 membered heterocyclyl, or acyl, each of which can be optionally substituted. For example, $R_{13}$ can be H, $C_1$-$C_6$alkyl, 3-12 membered aryl, 3-12 membered heteroaryl, 3-12 membered cycloalkyl, or 3-12 membered heterocyclyl, each of which can be optionally substituted. In some compounds of Formula II, $R_{13}$ is H, an optionally substituted $C_1$-$C_6$alkyl, optionally substituted 3-12 membered cycloalkyl, or optionally substituted 3-12 membered heterocyclyl. For example, $R_{13}$ is H, $C_1$-$C_6$alkyl substituted with an optionally substituted 3-12 membered aryl, an optionally substituted 3-12 membered cycloalkyl, or an optionally substituted 3-12 membered heterocyclyl. Exemplary alkyls include, but are not limited to, methyl, ethyl, propyl, isopropyl, 1-methylpropyl, 2-methylpropyl, butyl, and t-butyl, each of which can be optionally substituted. Exemplary aryls include, but are not limited to, phenyl, naphthyl, anthracenyl, indolyl, isoindolyl, benzothienyl, benzofuranyl, dibenzofuranyl, indazolyl, benzimidazolyl, benzthiazolyl, quinolyl, isoquinolyl, quinolinyl, phthalazinyl, quinazolinyl, quinoxalinyl, carbazolyl, acridinyl, phenazinyl, phenothiazinyl, phenoxazinyl, tetrahydroquinolinyl, tetrahydroisoquinolinyl, fluorenyl, indanyl, phenanthridinyl, tetrahydronaphthyl, indolinyl, phenoxazinyl, benzodioxanyl, and benzodioxolyl, each of which can be optionally substituted. Exemplary heterocyclyls include, but are not limited to, aziridine, oxirane, thiiarne, diazridine, oxaziridine, dioxirane, azetidine, oxetane, thietane, diazetidine, dioxetane, dithietane, -pyrrolidine, tetrahydropyran, tetrahydrothiophene, imidazolidine, pyrazolidine, oxazolidine, isoxazolidine, thiazolidine, isothiazolidine, dioxalane, dithiolane, piperidine, tetrahydropyran, thiane, piperazine, morpholine, thiomorpholine, dioxane, dithiane, hexahydro-1,3,5-triazine trioxane, trithiane, azepane, oxepane, thiepane, diazepane, azocane, oxocane, thiocane, azonane, oxonane, and thionane, each of which can be optionally substituted.

Exemplary cyclyls include, but are not limited to, cyclopropyl, cyclobutyl, cyclopentyl, cyclohexyl, each of which can be optionally substituted. In some embodiments, $R_{13}$ is H, cyclopentyl, piperidinylmethyl, or benzo[d][1,3]dioxolyl, in some embodiments, $R_{13}$ is H, In some compounds of Formula II, $R_{14}$ can be H, $C_1$-$C_6$alkyl, 3-12 membered aryl, 3-12 membered heteroaryl, 3-12 membered cycloalkyl, 3-12 membered heterocyclyl, or acyl, each of which can be optionally substituted. For example, $R_{14}$ can be H, $C_1$-$C_6$alkyl, 3-12 membered aryl, 3-12 membered heteroaryl, 3-12 membered cycloalkyl, or 3-12 membered heterocyclyl, each of which can be optionally substituted. In some compounds of Formula II, $R_{13}$ is H, an optionally substituted $C_1$-$C_6$alkyl, optionally substituted 3-12 membered cycloalkyl, or optionally substituted 3-12 membered heterocyclyl. For example, $R_{14}$ is H, $C_1$-$C_6$alkyl substituted with an optionally substituted 3-12 membered aryl, an optionally substituted 3-12 membered cycloalkyl, or an optionally substituted 3-12 membered heterocyclyl. Exemplary alkyls include, but are not limited to, methyl, ethyl, propyl, isopropyl, 1-methylpropyl, 2-methylpropyl, butyl, and t-butyl, each of which can be optionally substituted. Exemplary aryls include, but are not limited to, phenyl, naphthyl, anthracenyl, indolyl, isoindolyl, benzothienyl, benzofuranyl, dibenzofuranyl, indazolyl, benzimidazolyl, benzthiazolyl, quinolyl, isoquinolyl, quinolinyl, phthalazinyl, quinazolinyl, quinoxalinyl, carbazolyl, acridinyl, phenazinyl, phenothiazinyl, phenoxazinyl, tetrahydroquinolinyl, tetrahydroisoquinolinyl, fluorenyl, indanyl, phenanthridinyl, tetrahydronaphthyl, indolinyl, phenoxazinyl, benzodioxanyl, and benzodioxolyl, each of which can be optionally substituted. Exemplary heterocyclyls include, but are not limited to, aziridine, oxirane, thiiarne, diazridine, oxaziridine, dioxirane, azetidine, oxetane, thietane, diazetidine, dioxetane, dithietane, -pyrrolidine, tetrahydropyran, tetrahydrothiophene, imidazolidine, pyrazolidine, oxazolidine, isoxazolidine, thiazolidine, isothiazolidine, dioxalane, dithiolane, piperidine, tetrahydropyran, thiane, piperazine, morpholine, thiomorpholine, dioxane, dithiane, hexahydro-1,3,5-triazine trioxane, trithiane, azepane, oxepane, thiepane, diazepane, azocane, oxocane, thiocane, azonane, oxonane, and thionane, each of which can be optionally substituted.

Exemplary cyclyls include, but are not limited to, cyclopropyl, cyclobutyl, cyclopentyl, cyclohexyl, each of which can be optionally substituted. In some embodiments, $R_{14}$ is H, cyclopentyl, piperidinylmethyl, or benzo[d][1,3]dioxolyl. In some embodiments, $R_{14}$ is H, cyclopentyl, piperidinylmethyl, or benzo[d][1,3]dioxolyl.

It is noted that $R_{13}$ and $R_{14}$ can be same or different. Preferably, $R_{13}$ and $R_{14}$ are different. For example, $R_{13}$ and $R_{14}$ can be selected independently from the group consisting of H, $C_1$-$C_6$alkyl, 3-12 membered aryl, 3-12 membered heteroaryl, 3-12 membered cycloalkyl, 3-12 membered heterocyclyl, or acyl, each of which can be optionally substituted. In some embodiments, $R_{13}$ and $R_{14}$ can be independently H, an optionally substituted $C_1$-$C_6$alkyl, optionally substituted 3-12 membered cycloalkyl, or optionally substituted 3-12 membered heterocyclyl. For example, $R_{13}$ and $R_{14}$ can be independently H, 3-12 membered cyclyl or $C_1$-$C_6$alkyl substituted with an optionally substituted 3-12 membered aryl, an optionally substituted 3-12 membered cycloalkyl, or an optionally substituted 3-12 membered heterocyclyl. For example, $R_{13}$ and $R_{14}$ are independently H, a 3-12 membered cyclyl, or a $C_1$-$C_6$alkyl substituted with an optionally substituted 3-12 membered aryl or heterocyclyl. In some embodiments, one of $R_{13}$ and $R_{14}$ is H and other is a 3-12 membered cyclyl, or a $C_1$-$C_6$alkyl substituted with an optionally substituted 3-12 membered aryl or heterocyclyl.

In some embodiments at least one of $R_8$, $R_9$, $R_{10}$, $R_{11}$, and $R_{12}$ is a halide. In some $R_8$, $R_9$, $R_{10}$, $R_{11}$ and Ru embodiments at least two of $R_8$, $R_9$, $R_{10}$, $R_{11}$, and Ru are a halide. In some embodiments the halide is an iodide, bromide, chloride or fluoride. In some embodiments the halide is a chloride or a bromide. In some embodiments where there are two halides the halides can be the same or different. In some embodiments $R_8$ is a chloride and $R_{10}$ is a bromide. In some embodiments $R_8$ is a chloride and $R_{11}$ is a chloride. In some embodiments $R_9$ is a chloride. In some embodiments $R_{10}$ is a chloride. In some embodiments $R_8$ is a chloride and $R_{10}$ is a chloride. In some embodiments at least one, at least two, at least three, at least four or all, of $R_8$, $R_9$, $R_{10}$, Ru, and Ru is H. In some embodiments at least one of $R_8$, $R_9$, $R_{10}$, Ru, and Ru is a methoxy. In some embodiments $R_{13}$ is a 5 or 6 member cycloalkyl, heterocyclyl, aryl, or heteroaryl. In some embodiments $R_{13}$ is the following herterocycl having the structure of fragment B:

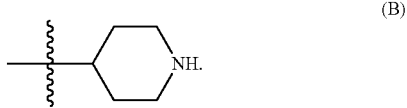 [SMILES: *C1CCNCC1]

(B)

In some embodiments the compound is selected from the following compounds;

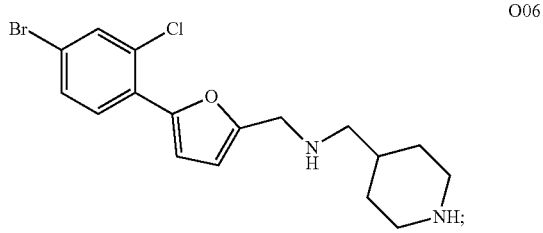

O06

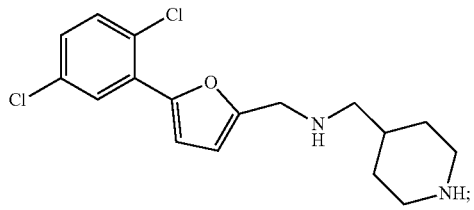

A06

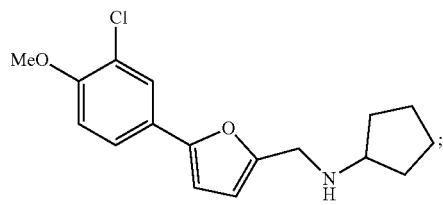

I17

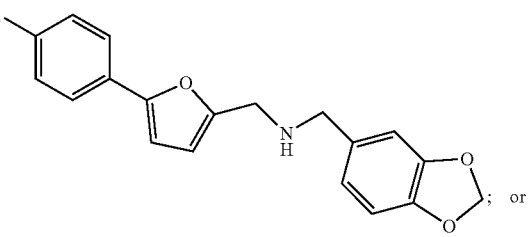

K05

; or

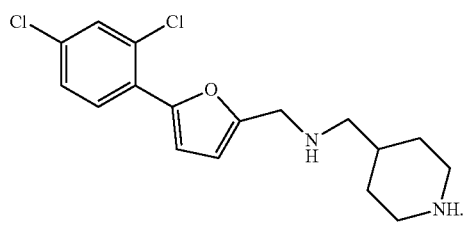

G06

In some embodiments, the compound is compound O06.

In some embodiments of Formula III: $R_{15}$, $R_{16}$, $R_{17}$, and $R_{18}$ independently are H, alkyl, aryl, heteroaryl, heteroalkyl, cycloalkyl, heterocyclyl, acyl, allyl, OH, alkoxy, cyano, carboxy, $CF_3$, halide, NH(alkyl), NH(aryl) or $NH_2$, each of which can be optionally substituted; $R_{19}$ is H, alkyl, aryl, heteroaryl, heteroalkyl, cycloalkyl, heterocyclyl, acyl, or allyl, each of which can be optionally substituted; $R_{19}$ is H, alkyl, aryl, heteroaryl, heteroalkyl, cycloalkyl, heterocyclyl, acyl, or allyl, each of which can be optionally substituted.

In some compounds of Formula III, $R_{15}$ can be H, $C_1$-$C_6$alkyl, 3-12 membered aryl, 3-12 membered heteroaryl, 3-12 membered cycloalkyl, 3-12 membered heterocyclyl, acyl, OH, $C_1$-$C_6$alkoxy, CN, $CF_3$, halide, NH($C_1$-$C_6$alkyl), NH(3-12 membered aryl) or $NH_2$, each of which can be optionally substituted. For example, $R_{15}$ can be H, acyl, OH, $C_1$-$C_6$alkoxy, CN, $CF_3$, halide, NH($C_1$-$C_6$alkyl), or $NH_2$, each of which can be optionally substituted. In some compounds of Formula III, $R_{15}$ is H, OH, $CF_3$, CN, $NH_2$, Cl, F, I or Br. Preferably, $R_{15}$ is H.

In some compounds of Formula III, $R_{16}$ can be H, $C_1$-$C_6$alkyl, 3-12 membered aryl, 3-12 membered heteroaryl, 3-12 membered cycloalkyl, 3-12 membered heterocyclyl, acyl, OH, $C_1$-$C_6$alkoxy, CN, $CF_3$, halide, NH($C_1$-$C_6$alkyl), NH(3-12 membered aryl) or $NH_2$, each of which can be optionally substituted. For example, $R_{16}$ can be 3-12 membered aryl, 3-12 membered heteroaryl, 3-12 membered cycloalkyl, 3-12 membered heterocyclyl, each of which can be optionally substituted. In some compounds of Formula III, $R_{16}$ is an optionally substituted 3-12 membered aryl. Exemplary aryls include, but are not limited to, phenyl, naphthyl, anthracenyl, indolyl, isoindolyl, benzothienyl, benzofuranyl, dibenzofuranyl, indazolyl, benzimidazolyl, benzthiazolyl, quinolyl, isoquinolyl, quinolinyl, phthalazinyl, quinazolinyl, quinoxalinyl, carbazolyl, acridinyl, phenazinyl, phenothiazinyl, phenoxazinyl, tetrahydroquinolinyl, tetrahydroisoquinolinyl, fluorenyl, indanyl, phenanthridinyl, tetrahydronaphthyl, indolinyl, phenoxazinyl, benzodioxanyl, and benzodioxolyl, each of which can be optionally substituted. In some embodiments, $R_{16}$ is an optionally substituted aryl, e.g., an optionally substituted phenyl. Preferably, $R_{16}$ is 4-halophenyl, e.g., 4-chlorophenyl or 4-fluorophenyl.

In some compounds of Formula III, $R_{17}$ can be H, $C_1$-$C_6$alkyl, 3-12 membered aryl, 3-12 membered heteroaryl, 3-12 membered cycloalkyl, 3-12 membered heterocyclyl, acyl, OH, $C_1$-$C_6$alkoxy, CN, $CF_3$, halide, NH($C_1$-$C_6$alkyl), NH(3-12 membered aryl) or $NH_2$, each of which can be optionally substituted. For example, $R_{17}$ can be 3-12 membered aryl, 3-12 membered heteroaryl, 3-12 membered cycloalkyl, 3-12 membered heterocyclyl, each of which can be optionally substituted. In some compounds of Formula III, $R_{17}$ is an optionally substituted 3-12 membered aryl. Exemplary aryls include, but are not limited to, phenyl, naphthyl, anthracenyl, indolyl, isoindolyl, benzothienyl, benzofuranyl, dibenzofuranyl, indazolyl, benzimidazolyl, benzthiazolyl, quinolyl, isoquinolyl, quinolinyl, phthalazinyl, quinazolinyl, quinoxalinyl, carbazolyl, acridinyl, phenazinyl, phenothiazinyl, phenoxazinyl, tetrahydroquinolinyl, tetrahydroisoquinolinyl, fluorenyl, indanyl, phenanthridinyl, tetrahydronaphthyl, indolinyl, phenoxazinyl, benzodioxanyl, and benzodioxolyl, each of which can be optionally substituted. In some embodiments, $R_{17}$ is an optionally substituted aryl, e.g., an optionally substituted phenyl. Preferably, $R_{17}$ is phenyl.

In some compounds of Formula III, $R_{18}$ can be H, $C_1$-$C_6$alkyl, 3-12 membered aryl, 3-12 membered heteroaryl, 3-12 membered cycloalkyl, 3-12 membered heterocyclyl, acyl, OH, $C_1$-$C_6$alkoxy, CN, $CF_3$, halide, NH($C_1$-$C_6$alkyl), NH(3-12 membered aryl) or $NH_2$, each of which can be optionally substituted. For example, $R_{18}$ can be H, $C_1$-$C_6$alkyl, acyl, OH, $C_1$-$C_6$alkoxy, CN, $CF_3$, halide, NH($C_1$-$C_6$alkyl), or $NH_2$, each of which can be optionally substituted. In some compounds of Formula III, $R_{18}$ is H, methyl, ethyl, propyl, isopropyl, 1-methylpropyl, 2-methylpropyl, butyl, t-butyl, pentyl, hexyl, OH, $CF_3$, CN, $NH_2$, Cl, F, I or Br. In some embodiments, $R_{18}$ is a $C_1$-$C_6$alkyl, e.g., methyl, ethyl, propyl, isopropyl, 1-methylpropyl, 2-methylpropyl, butyl, t-butyl, pentyl, and hexyl. Preferably, $R_{18}$ is methyl.

In some compounds of Formula III, $R_{19}$ can be H, $C_1$-$C_6$alkyl, 3-12 membered aryl, 3-12 membered heteroaryl, 3-12 membered cycloalkyl, 3-12 membered heterocyclyl, or acyl, each of which can be optionally substituted. For example, $R_{13}$ can be H, $C_1$-$C_6$alkyl, 3-12 membered aryl, 3-12 membered heteroaryl, 3-12 membered cycloalkyl, or 3-12 membered heterocyclyl, each of which can be optionally substituted. In some compounds of Formula III, $R_{19}$ is H, an optionally substituted $C_1$-$C_6$alkyl, optionally substituted 3-12 membered cycloalkyl, or optionally substituted 3-12 membered heterocyclyl. For example, $R_{19}$ is H or an optionally substituted $C_1$-$C_6$alkyl. Exemplary alkyls include, but are not limited to, methyl, ethyl, propyl, isopropyl, 1-methylpropyl, 2-methylpropyl, butyl, and t-butyl, each of which can be optionally substituted. In some embodiments, $R_{19}$ is H, methyl, ethyl, propyl, isopropyl, 1-methylpropyl, 2-methylpropyl, butyl, t-butyl, pentyl, or hexyl. Preferably $R_{19}$ is H.

In some embodiments at least one of $R_{15}$ or $R_{16}$ is an aryl group. In some embodiments at least one of $R_{15}$ or $R_{16}$ is a halogenated aryl group. In some embodiments herein $R_{16}$ a halogenated aryl group. In some embodiments the halogen is an iodide, bromine, chloride or a fluoride. In some embodiments the halogen is a chloride or a fluoride. For example, in some embodiments the halogenated aryl groups has the structure of the following fragment C:

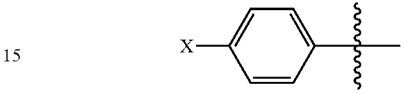

wherein X is a halide, selected from F, Cl, Br or I. In some embodiments at least one of $R_{17}$ or $R_{18}$ is an alkyl group. In some embodiment at least one of $R_{17}$ or $R_{18}$ is an aromatic group. In some embodiment at least one of $R_{17}$ or $R_{18}$ is an alkyl group and the other of $R_{17}$ or $R_{18}$ is an aromatic group. For example, in some embodiments at least one of $R_{17}$ or $R_{18}$ is an methyl, ethyl or propyl group and the other of $R_{17}$ or $R_{18}$ is an phenyl group.

In some embodiments the compound is selected from the following compounds;

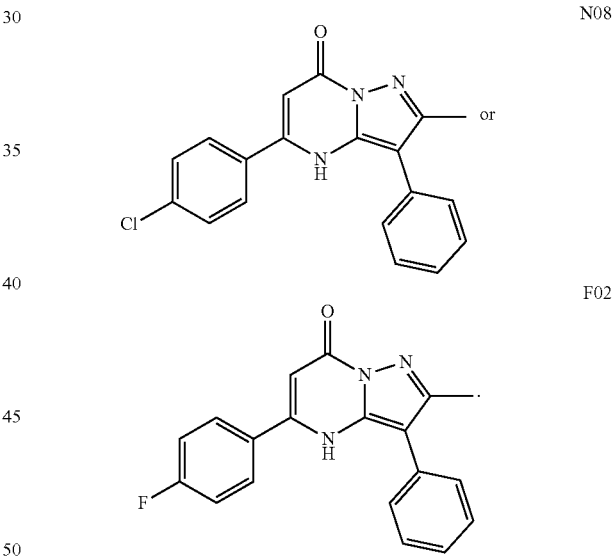

In some embodiments, the compound is N08.

In the embodiments described herein, any alkyl, alkenyl, cycloalkyl, heterocyclyl, heteroaryl or aryl is optionally substituted with 1, 2, or 3 groups selected from OH, CN, SH, $SO_2NH_2$, $SO_2(C_1$-$C_4)$alkyl, $SO_2NH(C_1$-$C_4)$alkyl, halogen, carbonyl, thiol, cyano, $NH_2$, NH($C_1$-$C_4$)alkyl, N[($C_1$-$C_4$)alkyl]$_2$, C(O)$NH_2$, COOH, COOMe, acetyl, ($C_1$-$C_8$)alkyl, O($C_1$-$C_8$)alkyl, O($C_1$-$C_8$)haloalkyl, ($C_2$-$C_8$)alkenyl, ($C_2$-$C_8$)alkynyl, haloalkyl, thioalkyl, cyanomethylene, alkylaminyl, aryl, heteroaryl, substituted aryl, $NH_2$—C(O)-alkylene, NH(Me)-C(O)-alkylene, $CH_2$—C(O)— alkyl, C(O)— alkyl, alkylcarbonylaminyl, $CH_2$—[CH(OH)]$_m$—($CH_2$)$_p$—OH, $CH_2$—[CH(OH)]$_m$—($CH_2$)$_p$—$NH_2$ or $CH_2$-aryl-alkoxy; or wherein any alkyl, cycloalkyl or heterocyclyl is optionally substituted with oxo; "m" and "p" are independently 1, 2, 3, 4, 5 or 6.

As used herein, a "stereoisomer" refers to each of two or more compounds differing only in the spatial arrangement of their atom.

As used herein, "tautomers" refers to two molecules with the same molecular formula but different connectivity, for example, a keto-enol pair.

The compound in some embodiments can exist in various isomeric forms, as well as in one or more tautomeric forms, including both single tautomers and mixtures of tautomers. The term "isomer" is intended to encompass all isomeric forms of a compound of this invention, including tautomeric forms of the compound.

Some compounds described here can have asymmetric (chiral) centers and can therefore exist in different enantiomeric and diastereomeric forms. A compound of the invention can be in the form of an optical isomer or a diastereomer. Accordingly, some embodiments encompass compounds and their uses as described herein in the form of their optical isomers, diastereoisomers and mixtures thereof, including a racemic mixture. Optical isomers of the compounds according to some embodiments can be obtained by known techniques such as asymmetric synthesis, chiral chromatography, or via chemical separation of stereoisomers through the employment of optically active resolving agents.

Unless otherwise indicated "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

As used herein the term "aryl", whether alone or as part of a substituent group, refers to an aromatic ring comprising between 6 to 14 carbon atoms. Suitable examples include, but are not limited to, phenyl, and naphthyl.

As used herein, "cycloalkyl" refers to a stable non-aromatic monocyclic or polycyclic hydrocarbon radical consisting solely of carbon and hydrogen atoms, which may include fused or bridged ring systems, having from three to fifteen carbon atoms, is some embodiments having from three to ten carbon atoms, three to nine carbon atoms, three to eight carbon atoms, three to seven carbon atoms, three to six carbon atoms, three to five carbon atoms, a ring with four carbon atoms, or a ring with three carbon atoms. The cycloalkyl ring may be saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like.

As used herein, "heterocyclyl", "heterocycle", or "heterocyclic ring" refers to a stable 3- to 18-membered saturated or unsaturated radical which consists of two to twelve carbon atoms and from one to six heteroatoms, for example, one to five heteroatoms, one to four heteroatoms, one to three heteroatoms, or one to two heteroatoms selected from the group consisting of nitrogen, oxygen and sulfur. Exemplary heterocycles include without limitation stable 3-15 membered saturated or unsaturated radicals, stable 3-12 membered saturated or unsaturated radicals, stable 3-9 membered saturated or unsaturated radicals, stable 8-membered saturated or unsaturated radicals, stable 7-membered saturated or unsaturated radicals, stable 6-membered saturated or unsaturated radicals, or stable 5-membered saturated or unsaturated radicals.

Unless stated otherwise specifically in the specification, the heterocyclyl radical may be a monocyclic, bicyclic, tricyclic or tetracyclic ring system, which may include fused, spiro or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of non-aromatic heterocyclyl radicals include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, thietanyl, trithianyl, tetrahydropyranyl, thiomorpholinyl, thiamorpholinyl, 1-oxo-thiomorpholinyl, and 1,1-dioxo-thiomorpholinyl. Heterocyclyls include heteroaryls as defined herein, and examples of aromatic heterocyclyls are listed in the definition of heteroaryls below.

As used herein, the term "heteroaryl" or "heteroarylene" refers to a 5- to 14-membered ring system radical comprising hydrogen atoms, one to thirteen carbon atoms, one to six heteroatoms selected from the group consisting of nitrogen, oxygen and sulfur, and at least one aromatic ring. In some embodiments, the heteroaryl radical may be a stable 3-12 membered ring, a stable 5-10 membered ring, a stable 5-9 membered ring, a stable 5-8 membered ring, a stable 5-7 membered ring, or a stable 6-membered ring that comprises at least 1 heteroatom, at least 2 heteroatoms, at least 3 heteroatoms, at least 4 heteroatoms, at least 5 heteroatoms or at least 6 heteroatoms. Heteroaryls may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. The heteroatom may be a member of an aromatic or non-aromatic ring, provided at least one ring in the heteroaryl is aromatic. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzopyranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (e.g. thienyl).

As used herein the term "acyl" refers to a group of the Formula —C(O)$C_n$ wherein $C_n$ represent a straight or branched alkyl chain wherein n can be 1, 2, 3, 4, 5, 6, 7, 8, 9 or 10. Where an "acetyl" refers to the methyl derivative, —C(O)CH$_3$.

As used herein a "ester" refers to a group of the formula —C(O)—O$C_n$ wherein $C_n$ represent a straight or branched alkyl chain wherein n can be 1, 2, 3, 4, 5, 6, 7, 8, 9 or 10. For example a chemical compound derived from an acid in which at least one —OH (hydroxyl) group is replaced by an —O-alkyl (alkoxy) group.

As used herein the term "alkyl", whether alone or as part of a substituent group, refers to a saturated $C_1$-$C_n$ carbon chain, wherein the carbon chain may be straight or branched; wherein n can be 2, 3, 4, 5, 6, 7, 8, 9 or 10. Suitable examples include, but are not limited to methyl, ethyl, propyl, isopropyl, butyl, isobutyl, sec-butyl, t-butyl, n-pentyl and n-hexyl.

As used herein the term "alkenyl", whether alone or as part of a substituent group, refers to a $C_2$-$C_n$ carbon chain, wherein the carbon chain may be straight or branched, wherein the carbon chain contains at least one carbon-carbon double bond, and wherein n can be 3, 4, 5, 6, 7, 8, 9, or 10.

As used herein the term "alkynyl", whether alone or as part of a substituent group, refers to a $C_2$-$C_n$ wherein the carbon chain may be straight or branched, wherein the carbon chain contains at least one carbon-carbon triple bond, and wherein n can be 3, 4, 5, 6, 7, 8, 9, or 10.

The groups of the present disclosure can be unsubstituted or substituted, as herein defined. In addition, the substituted groups can be substituted with one or more groups such as a $C_1$-$C_6$ alkyl, $C_{1-4}$ alkyl, —O—$C_{1-4}$ alkyl, hydroxyl, amino, ($C_{1-4}$ alkyl)amino, di($C_{1-4}$ alkyl)amino, —S—($C_{1-4}$ alkyl), —SO—($C_{1-4}$ alkyl), —SO$_2$—($C_{1-4}$ alkyl), halogen, aryl, heteroaryl, and the like.

With reference to substituents, the term "independently" means that when more than one of such substituents is possible, such substituents may be the same or different from each other.

"Amino" refers to a —NH$_2$ substituent.
"Aminocarbonyl" or "Amido" refers to the —C(O)NH$_2$ substituent.
"Carboxyl" refers to the —CO$_2$H substituent.
"Carbonyl" refers to a —C(O)—, —(CO)— or —C(=O)— group. All notations are used interchangeably within the specification.
"Cyano" refers to the —C≡N substituent.
"Hydroxy" or "hydroxyl" refers to the —OH substituent.
"Oxo" refers to a =O substituent
"Thio" or "thiol" refer to a-SH substituent.
Compound words have the meaning of the individual functional groups or fragments as would be understood in the art. For example, "hydroxyalkyl" refers to the -(alkyl)-OH substituent, "thioalkyl" refers to the -(alkyl)-SH substituent, "cyanoalkylene" refers to the -(alkylene)C≡N substituent; "hydroxyalkylene" refers to the -(alkylene)OH substituent; "arylmethoxy" refers to a methoxy substituted aryl group.

In some embodiments the disclosure relates to pharmaceutical compositions comprising a therapeutically effective amount of a compound, or stereoisomers, tautomers, or pharmaceutically acceptable salts thereof, and a pharmaceutically acceptable carrier, wherein the compound is selected from one or more of:

3448_L17

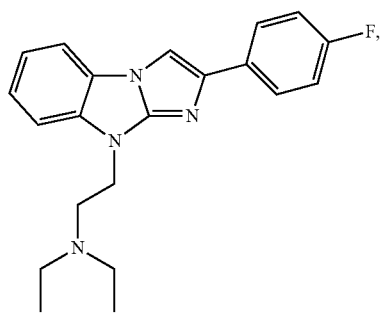

3465_M18

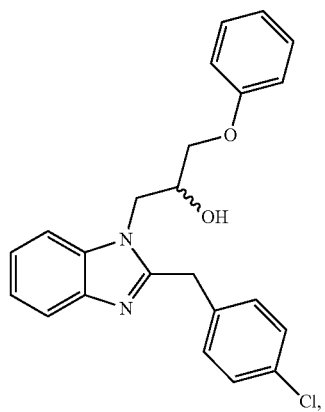

3453_L03

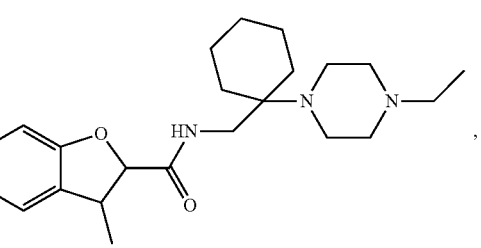

3448_I03

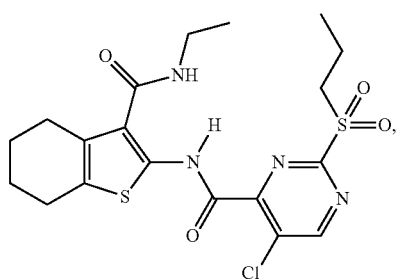

-continued
3453_P01
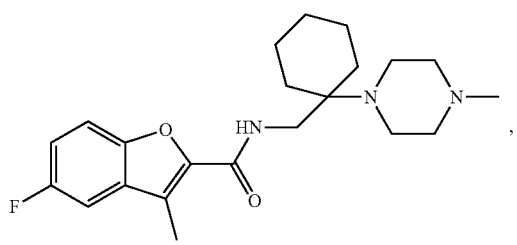
3439_G01
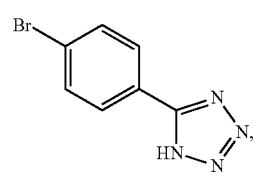
3431_N06
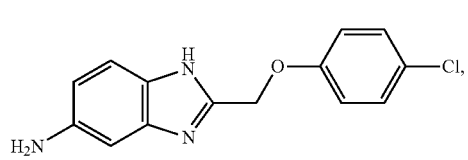
3451_P09
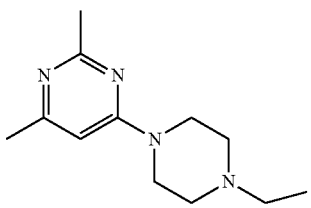
3468_H10
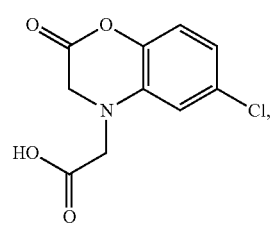
3445_J12
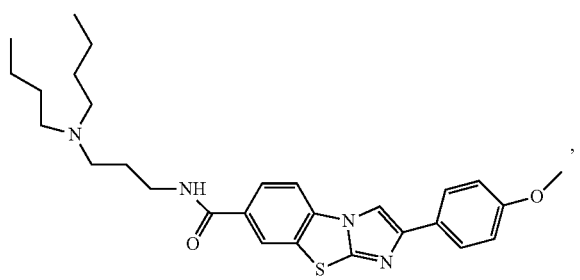
-continued
3430_P01
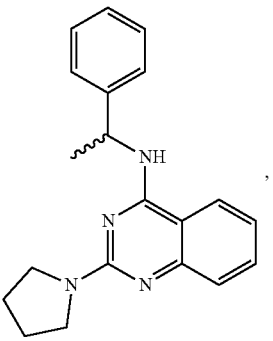
3446_N09
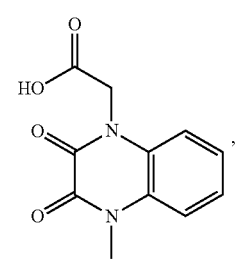
3431_L15
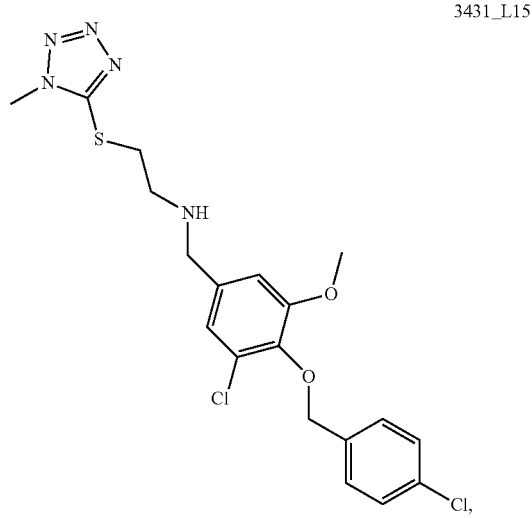
3431_F15
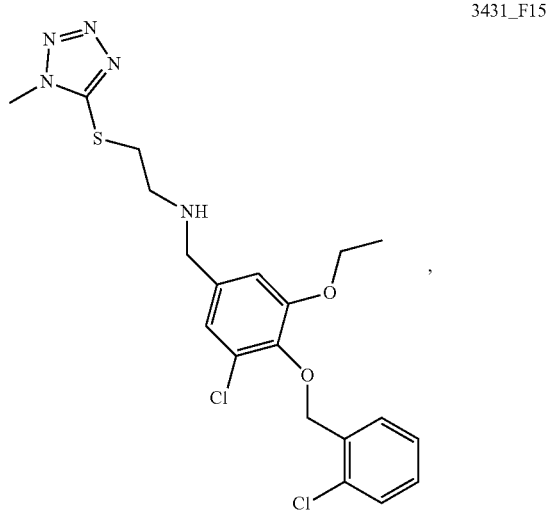

3437_N01
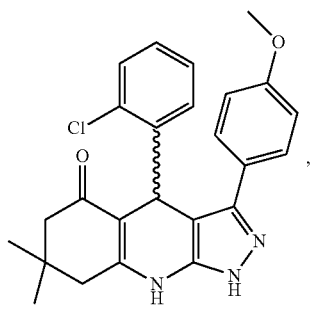
3437_I01
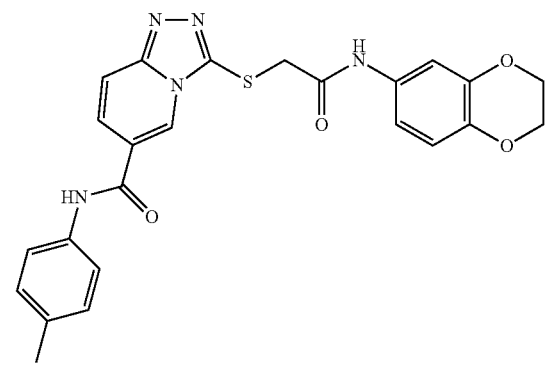
3465_I11
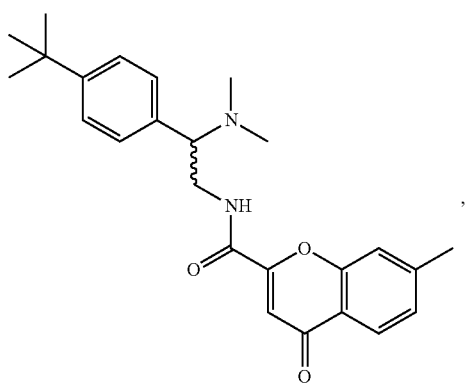
3440_K02
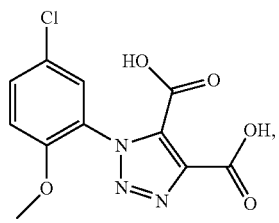
3445_G13
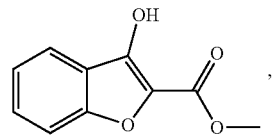
3439_I03
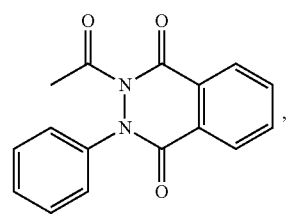
3433_I21
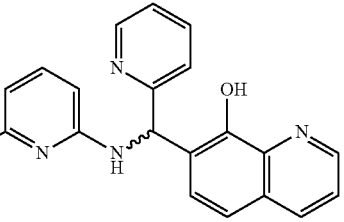
3437_K01
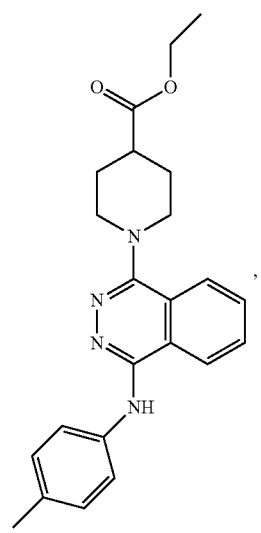
3432_G13
3439_A03
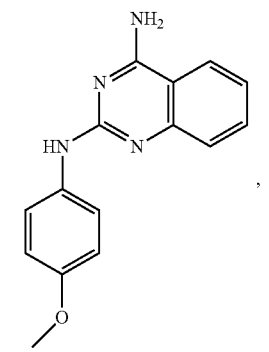

3449_C05

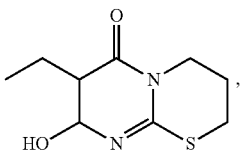

3450_I-07

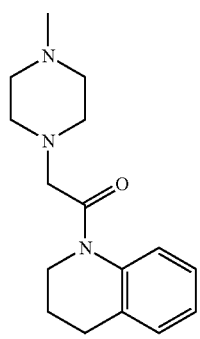

3485_P01

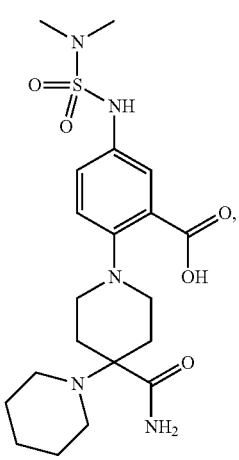

3545_C09

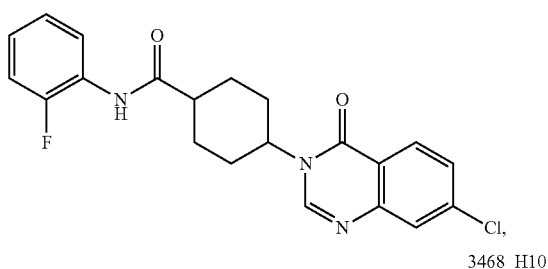

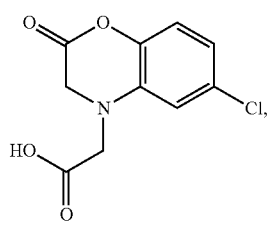

3449_C05

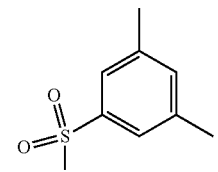

3450_I-07

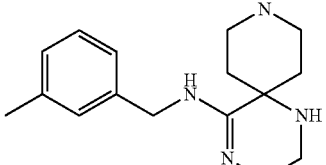

3485_P01

3468_H10

3549_C13

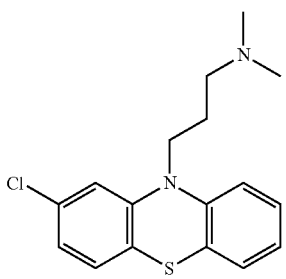

, and

3430_C19

In some embodiments the compound is

Pharmaceutical salts: In one aspect, provided herein is a composition or pharmaceutical composition comprising any of the compounds or agents described herein. In one embodiment, the composition further comprises a pharmaceutically acceptable carrier.

Compounds of Formula I, II, III agents described herein, or derivatives thereof can also include pharmaceutically acceptable salts thereof. As used herein, the term "pharmaceutically-acceptable salts" refers to the conventional non-toxic salts or quaternary ammonium salts of small molecules as disclosed herein, e.g., from non-toxic organic or inorganic acids. These salts can be prepared in situ in the administration vehicle or the dosage form manufacturing process, or by separately reacting a small molecule in its free base or acid form with a suitable organic or inorganic acid or base, and isolating the salt thus formed during subsequent purification. Conventional nontoxic salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", J. Pharm. Sci. 66:1-19 (1977), content of which is herein incorporated by reference in its entirety.

In some embodiments of the aspects described herein, representative pharmaceutically acceptable salts include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

Bacterial Efflux Pump Inhibitors

In certain embodiments, the methods and compositions described herein comprise treatment with a bacterial efflux pump inhibitor in combination with the antibiotic agent. Essentially any bacterial efflux pump inhibitor can be used with the methods and compositions described herein. As will be recognized by those of skill in the art, compounds with low toxicity or low side effect profiles are preferred when the bacterial efflux pump inhibitor is to be administered to a subject or patient (e.g., a human). One of skill in the art will also recognize that different bacteria will necessarily express different bacterial efflux pumps. Thus, the inhibitor to be used in methods of treatment as described herein can be selected based on expected efficacy against a particular bacterial efflux pump expressed by the bacterium. In some embodiments, the methods of treatment can include two or more bacterial efflux pump inhibitors (e.g., 3, 4, 5, 6, 7, or more).

Non-limiting examples of bacterial efflux pump inhibitors include pheophorbide A, 5'-MHC, carnosic acid, carnosol, cathinone, theobromine, reserpine, 4'5'-O-dicaffeoylquinic acid, curcumin, kaempferol, N-trans-feruloyl 4'-O-methyldopamine, silibinin, genistein, isoflavone, artesunate, orizabins, resin glycosides (e.g., orizabins IX, murucoidins, stoloniferin), citropten, furocoumarins, coumarins, crysolplenon and crysoplenetin, diosmetin, murucoidins, chrysosplenol-D, phenylpropanoid, essential oils from Salvi spp., spectinamides, diterpenes (e.g., ferruginol), totarol, boeravinone B, α-terpinine, biochanin A, cumin seed oil, cuminaldehyde, epigallacatechin gallate, epicatechin gallate, galbanic acid, orobol, baicalein, tannic acid, conessine, linoleic and oleic acids, tiliroside, kaempferol-3-O-b-d-(6-E-p-coumaroyl)Glucopyranoside, capsaicin (e.g., 8-methyl-N-vanillyl-6 nonenamide), caeffeoylquinic acid, piperine, clerodane diterpene, 16α-hydroxycleroda-3,13(14)-Z-dien-15,16-olide, chalcone, olaanolic acid, ulvaol, quercetin, tetrandrine, farnesol, 4-acetyl-3-(4-fluorphenyl)-1-(p-tolyl)-5-methylpyrrole, N-trans-3,4—O dimethylcaffeoyl triptamine, 5,7 deoxyhydnocarpin-D (5,7-DHC-D), chalcone and chalcone derivatives, 4-phenoxy-4'-dimethylaminoethoxy chalcone (4-DAEC), SK-20, SK56, SLUPP-225, SLUPP-417, PAβN, NMP(1-(1 napththylmethyl)-piperazine), 5-MPC, verapamil, piperazine arylideneimidazolones, ethyl 6-amino-1 cyclopropyl-7-4-(hydroxyimino)-3-methyl-3,4,7,8-tetrahydro-2H-thiopyrano[3,2,-c]pyridin-6 (5H)-yl]-8-methyl-4-oxo-1,4-dihydroquinoline-3-carboxylate (EDCQ), 10-(4-(-3-phenylureido)-benzylamino)-9-fluoro-3,7-dihydro-3-methyl-7-oxo-2H-[1,4]oxazino[2,3,4,-ij]quinolone-6-carboxylic acid (Q6CA), pyridoquinolines, 2-phenyl-4-hydroxyquinoline derivativesN,N-diethyl-2-{[2-(4-proppoxyphenyl) quinolin-4-yl]oxy}-ethanamine hydrochloride (PPQE), 4-(2-piperidin-1-ylehoxy)-2-(4 propoxyphenyl quinoline (PPQ), 4-(2-(piperazin-1-yl) ethoxy)-2-(4 propoxyphenyl) quinolone (PQQ4R), (Z)-5-(2, 4-dimethoxybenzylidene)-3-(2-hydroxy-3-(isopropylamino) propyl) imidazolidine-2,4-dione, 5-nitro-2-phenylindole (e.g., INF 55, INF 240, INF 271, INF 277),[4-benzyloxy-2-(5-nitro0-1H-2-yl)-phenyl]-methanol (BNPM), 2-phenylbenzo[b]thiophene-3 carboxaldehyde (2-PTC), 3-(3,4-dihydronapth-2-yl)-propenoic acid isobutyl amide (3-PIA), 2-((2-4-propoxyphenyl) quinolin-4-yl) oxy) alkylamines 1-4,13-cyclopentylthio-5-OH-TC (13-CPTC), semi-synthetic tetracycline analogs, Phe-Arg-β-naphthylamide (MC-207, 110), biricodar, G-918, timcodar, SILA 421, phenothiazine and derivatives (e.g., methylene blue, promethazine, chlorpromazine and thioridazine), chlorpromazine, phenyl-1,4-benzothiazine derivatives, pyridoquinolines, 2-(4-propoxy-phenyl) quinolone derivatives, valinomycin, pyridopyrimidine analogues (e.g., D13-9001, D2), pyranopyridine derivatives (E.g., MBX2319), (e)-N-(3,4,-difluorophenyl)-1-2-(2-(3-(methylthio)phenylimino)-4-oxothiazolidin-5-yl, DHA, DHA27, riparin-B, nerol, dimethyl octanol, estragole, monoterpenes, PA EPA amides, 6-(aryl)alkoxypyridine-3-boronic acids, 6-(3-phenylpropoxy)pyridine-3-boronic acid 3i and 6-(4-phenylbutoxy), pyridine-3-boronic acid 3j, ginsenoside 20(S)—Rh2 (Rh2), pimozine, sertraline, EA-371α and EA-371δ (see e.g., Sharma et al. *Indian J Med Res* 149:129-145 (2019), the contents of which are incorporated herein by reference in its entirety).

Dosage and Administration

In some aspects, provided herein are compositions and methods for treating a bacterial infection in a subject. Such methods include administration of an antibiotic agent identified using the bacterial whole cell assay described herein. In some embodiments, the antibiotic agent is administered in combination with a bacterial efflux pump inhibitor.

In certain embodiments, the bacterial infection in a subject comprises infection with at least one antibiotic-resistant strain of bacteria. In one embodiment, the subject having a bacterial infection to be treated is a human subject. In other embodiments, the subject can be a mammal. The methods comprise administering to the subject an effective amount of a pharmaceutical composition comprising an antibiotic agent identified using the whole cell bacterial assay described herein, or a compound of Formula I, II, or III. The appropriate dosage range for a given antibiotic agent depends upon the potency, and includes amounts large enough to produce the desired effect, e.g., reduction in at least one symptom of a bacterial infection, or reduction in the number of bacteria in a given biological sample. The dosage of the antibiotic agent and/or the bacterial efflux pump inhibitor should not be so large as to cause unacceptable or life-threatening adverse side effects. Generally, the dosage will vary with the type of inhibitor, and with the age, condition, and sex of the patient. The dosage can be determined by one of skill in the art and can also be adjusted by the individual physician in the event of any complication.

Typically, the dosage of a compound of Formula I, II or III or a bacterial efflux pump inhibitor ranges from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 μg/kg body weight to 30 μg/kg body weight.

Alternatively, the dose range will be titrated to maintain serum levels between 5 µg/mL and 30 µg/mL.

Currently available antibiotic therapies and their dosages, routes of administration and recommended usage are known in the art and have been described in such literature as the Physician's Desk Reference (60th ed., 2017).

Administration of the doses recited above or as employed by a skilled clinician can be repeated for a limited and defined period of time. In some embodiments, the doses are given once a day, or multiple times a day, for example but not limited to three times a day. Typically, the dosage regimen is informed by the half-life of the agent as well as the minimum therapeutic concentration of the agent in a given biological sample. In a preferred embodiment, the doses recited above are administered daily for several weeks or months. The duration of treatment depends upon the subject's clinical progress and continued responsiveness to therapy. Continuous, relatively low maintenance doses are contemplated after an initial higher therapeutic dose.

A therapeutically effective amount is an amount of an agent that is sufficient to produce a statistically significant, measurable change of a given symptom of a bacterial infection (see "Efficacy Measurement" below). Such effective amounts can be gauged in clinical trials as well as animal studies for a given agent. For example, reduction of a given symptom of pneumonia, such as fever, pain, or mucus production, can be indicative of adequate therapeutic efficacy of an agent(s) against carbapenem-resistant *Klebsiella pneumoniae*, or *Pseudomonas aeruginosa*.

Agents useful in the methods and compositions described herein can be administered topically, intravenously (by bolus or continuous infusion), orally, by inhalation, intraperitoneally, intramuscularly, subcutaneously, intracavity, and can be delivered by peristaltic means, if desired, or by other means known by those skilled in the art. The agent can be administered systemically, if so desired.

Therapeutic compositions containing at least one agent can be conventionally administered in a unit dose. The term "unit dose" when used in reference to a therapeutic composition refers to physically discrete units suitable as unitary dosage for the subject, each unit containing a predetermined quantity of an antibiotic agent calculated to produce the desired therapeutic effect in association with the required physiologically acceptable diluent, i.e., carrier, or vehicle or in combination with a bacterial efflux pump inhibitor.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. An agent can be targeted by means of a targeting moiety, such as e.g., an antibody or targeted liposome technology.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more intervals by a subsequent injection or other administration. Alternatively, continuous intravenous infusion sufficient to maintain concentrations in the blood in the ranges specified for in vivo therapies are contemplated.

Combination Therapies: In some embodiments, an antibiotic agent, such as those selected using the whole cell bacterial assay described herein, is used in combination with at least one bacterial efflux pump inhibitor. In one embodiment, the combination therapy comprises compound N08 and PAβN. In another embodiment, the combination therapy comprises compound C17 and PAβN. In another embodiment, the combination therapy comprises compound O06 and PAβN.

In some embodiments, an antibiotic agent as described herein can be used in combination with at least one additional conventional antibiotic (e.g., penicillin, carbapenem, tetracyclines etc.) in the presence or absence of a bacterial efflux pump inhibitor.

In some embodiments, a therapeutically effective antibiotic treatment is administered to a subject concurrently with a combination therapy, such as a bacterial efflux pump inhibitor or at least one additional conventional antibiotic. As used herein, the term "concurrently" is not limited to the administration of the antibiotic agent and the bacterial efflux pump inhibitor at exactly the same time, but rather, it is meant that they are administered to a subject in a sequence and within a time interval such that they can act together (e.g., synergistically to provide an increased benefit than if they were administered otherwise). For example, the antibiotic agent and the bacterial efflux pump inhibitor may be administered at the same time or sequentially in any order at different points in time; however, if not administered at the same time, they should be administered sufficiently close in time so as to provide the desired therapeutic effect, preferably in a synergistic fashion. The antibiotic agent and the bacterial efflux pump inhibitor can be administered separately, in any appropriate form and by any suitable route. When the antibiotic agent and the bacterial efflux pump inhibitor are not administered in the same pharmaceutical composition, it is understood that they can be administered in any order to a subject in need thereof. For example, the bacterial efflux pump inhibitor can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the antibiotic agent, to a subject in need thereof (or vice versa). In various embodiments, the antibiotic agent and the bacterial efflux pump inhibitor are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the antibiotic agent and the bacterial efflux pump inhibitor are administered within the same office visit. In another embodiment, the antibiotic agent and the bacterial efflux pump inhibitor are administered at 1 minute to 24 hours apart.

In other embodiments, the delivery of either the antibiotic agent or the bacterial efflux pump inhibitor ends before the delivery of the other agent/treatment begins. In some embodiments of either case, the treatment is more effective because of combined administration. For example, the antibiotic agent administered in combination with the bacterial efflux pump inhibitor is more effective than would be seen if the antibiotic agent were administered in the absence of the bacterial efflux pump inhibitor. In some embodiments, delivery is such that the reduction in a symptom, or other parameter related to the disorder is greater than what would be observed with the antibiotic agent delivered in the absence of the bacterial efflux pump inhibitor. The effect of such a combination can be partially additive, wholly additive, or greater than additive. The agent and/or other therapeutic agents, procedures or modalities can be administered during periods of active disease, or during a period of persistence or less active disease.

When administered in combination with a bacterial efflux pump inhibitor, the antibiotic agent of Formula I, II or III, or a compound identified using the assays described herein can be administered in an amount or dose that is higher, lower or the same as the amount or dosage of the antibiotic agent used individually, e.g., as a monotherapy. In certain embodiments, the administered amount or dosage of the antibiotic agent when administered in combination with a bacterial efflux pump inhibitor is lower (e.g., at least 20%, at least 30%, at least 40%, or at least 50%) than the amount or dosage of the antibiotic agent when used individually. In other embodiments, the amount or dosage of the antibiotic agent when administered in combination with a bacterial efflux pump inhibitor that results in a desired effect (e.g., reduction in a symptom of bacterial infection, reduced fever, reduced pain, reduction in number of bacterial cells in a given biological sample) is lower (e.g., at least 20%, at least 30%, at least 40%, or at least 50% lower) than the amount or dosage of the antibiotic agent required to achieve the same therapeutic effect when administered alone.

Pharmaceutical Compositions

An antibiotic agent selected for a given subject using the assays described herein in the Examples section (e.g., a compound of Formula I, II or III) can be administered as a pharmaceutical composition. In one embodiment, the pharmaceutical composition comprises both the antibiotic agent and a bacterial efflux pump inhibitor. In other embodiments, the antibiotic agent and the bacterial efflux pump inhibitor are administered in different compositions.

Pharmaceutical or therapeutic compositions comprising the antibiotic agent and/or the bacterial efflux pump inhibitor can contain a physiologically tolerable carrier, wherein the antibiotic agent and/or bacterial efflux pump inhibitor are dissolved or dispersed therein as an active ingredient(s). In a preferred embodiment, the pharmaceutical composition is not immunogenic when administered to a mammal or human patient for therapeutic purposes. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological or pharmaceutical composition that contains active ingredients dissolved or dispersed therein is well understood in the art and need not be limited based on formulation. Typically, such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition comprising at least one antibiotic agent can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the methods described herein that will be effective in the treatment of a particular disorder or condition will depend on the nature of the disorder or condition, and can be determined by standard clinical techniques.

Formulations for Particular Administration Routes: For buccal administration, the compositions may take the form of tablets or lozenges formulated in a conventional manner.

For administration by nasal inhalation, the antibiotic agent(s) or a composition thereof are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane, or carbon dioxide. In the case of a pressurized aerosol, the dosage may be determined by providing a valve to deliver a metered amount. Capsules and cartridges of, for example, gelatin for use in a dispenser may be formulated containing a powder mix of the compound and a suitable powder base, such as lactose or starch.

A pharmaceutical composition as described herein can be formulated for parenteral administration, e.g., by bolus injection or continuous infusion. Formulations for injection may be presented in unit dosage form, e.g., in ampoules or in multidose containers with, optionally, an added preservative. The compositions may be suspensions, solutions, or emulsions in oily or aqueous vehicles, and may contain formulatory agents such as suspending, stabilizing, and/or dispersing agents.

Pharmaceutical compositions for parenteral administration include aqueous solutions of the active preparation in water-soluble form. Additionally, suspensions of the active ingredients can be prepared as appropriate oily or water-based injection suspensions.

Suitable lipophilic solvents or vehicles include fatty oils such as sesame oil, or synthetic fatty acid esters such as ethyl oleate, triglycerides, or liposomes. Aqueous injection suspensions can contain substances that increase the viscosity of the suspension, such as sodium carboxymethyl cellulose, sorbitol, or dextran.

Optionally, the suspension may also contain suitable stabilizers or agents that increase the solubility of the active ingredients, to allow for the preparation of highly concentrated solutions. Alternatively, the active ingredient may be in powder form for constitution with a suitable vehicle, e.g., a sterile, pyrogen-free, water-based solution, before use.

In some embodiments, a composition of the invention can be delivered in an immediate release form. In other embodiments, a composition of the invention can be delivered in a controlled-release system or sustained-release system. Controlled- or sustained-release pharmaceutical compositions can have a common goal of improving drug therapy over the results achieved by their non-controlled or non-sustained-release counterparts. Advantages of controlled- or sustained-release compositions include extended activity of the antibiotic and the bacterial efflux pump inhibitor, reduced dosage frequency, and increased compliance. In addition, controlled- or sustained-release compositions can favorably affect the time of onset of action or other characteristics, such as blood levels of the antibiotic and the bacterial efflux pump inhibitor, and can thus reduce the occurrence of adverse side effects.

Controlled- or sustained-release compositions can comprise an immediate release portion and an extended release portion. The immediate release portion initially immediately releases an amount of the bacterial efflux pump inhibitor and/or the antibiotic that promptly produces the desired therapeutic or prophylactic effect, while the extended release portion gradually and continually releases other amounts of the bacterial efflux pump inhibitor and/or the antibiotic to maintain a level of therapeutic or prophylactic effect over an extended period of time. Controlled- or sustained-release of an active ingredient can be stimulated by various conditions, including but not limited to, changes in pH, changes in temperature, concentration or availability of enzymes, concentration or availability of water, or other physiological conditions or compounds.

Controlled-release and sustained-release dosage forms can be used to provide controlled- or sustained-release of one or more active ingredients using, for example, hydroxypropylmethyl cellulose, other polymer matrices, gels, permeable membranes, osmotic systems, multilayer coatings, microparticles, multiparticulates, liposomes, microspheres, or a combination thereof to provide the desired release profile in varying proportions. Suitable controlled- or sustained-release formulations known in the art, including those described herein, can be readily selected for use with the active ingredients of the invention in view of this disclosure. See also Goodson, "Dental Applications" (pp. 115-138) in Medical Applications of Controlled Release, Vol. 2, Applications and Evaluation, R. S. Langer and D. L. Wise eds., CRC Press (1984). Other controlled- or sustained-release systems that are discussed in the review by Langer, Science 249:1527-1533 (1990) can be selected for use according to the methods and compositions described herein. In one embodiment, a pump can be used (Langer, Science 249: 1527-1533 (1990); Sefton, CRC Crit. Ref Biomed. Eng. 14:201 (1987); Buchwald et al., Surgery 88:507 (1980); and Saudek et al., N. Engl. J. Med 321:574 (1989)). In another embodiment, polymeric materials can be used (see Medical Applications of Controlled Release (Langer and Wise eds., 1974); Controlled Drug Bioavailability, Drug Product Design and Performance (Smolen and Ball eds., 1984); Ranger and Peppas, J. Macromol. Sci. Rev. Macromol. Chem. 23:61 (1983); Levy et al., Science 228:190 (1985); During et al., Ann. Neurol. 25:351 (1989); and Howard et al., J. Neurosurg. 71:105 (1989)). In yet another embodiment, a controlled- or sustained-release system can be placed in proximity of a target of infection, e.g., skin, lungs, spinal column, brain, or gastrointestinal tract, thus requiring only a fraction of the systemic dose.

When in tablet or pill form, a pharmaceutical composition as described herein can be coated to delay disintegration and absorption in the gastrointestinal tract, thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

The pharmaceutical composition as described herein can also be formulated in rectal compositions such as suppositories or retention enemas, using, for example, conventional suppository bases such as cocoa butter or other glycerides.

Devices and coatings: Provided herein are compositions that include devices coated with the bacterial efflux pump inhibitor and an antibiotic as described above or methods of coating such devices with the antibiotic agent and the bacterial efflux pump inhibitor. Exemplary devices include, but are not limited to, vessel hulls, automobile surfaces, air plane surfaces, membranes, filters, and industrial equipment.

In certain preferred embodiments, the surface can also be comprised in medical devices, instruments, and implants. Examples of such medical devices, instruments, and implants include any object that is capable of being implanted temporarily or permanently into a mammalian organism, such as a human. Representative medical devices, instruments, and implants that can be used include, for example, central venous catheters, urinary catheters, endotracheal tubes, mechanical heart valves, pacemakers, vascular grafts, stents and prosthetic joints.

Medical devices that can be coated with an antibiotic agent (±a bacterial efflux pump inhibitor) include, but are not limited to, artificial blood vessels, catheters and other devices for the removal or delivery of fluids to patients, artificial hearts, artificial kidneys, orthopedic pins, prosthetic joints, plates and implants; catheters and other tubes (including urological and biliary tubes, endotracheal tubes, peripherally insertable central venous catheters, dialysis catheters, long term tunneled central venous catheters, peripheral venous catheters, short term central venous catheters, arterial catheters, pulmonary catheters, Swan-Ganz catheters, urinary catheters, peritoneal catheters), urinary devices (including long term urinary devices, tissue bonding urinary devices, artificial urinary sphincters, urinary dilators), shunts (including ventricular or arterio-venous shunts); prostheses (including breast implants, penile prostheses, vascular grafting prostheses, aneurysm repair devices, mechanical heart valves, artificial joints, artificial larynxes, otological implants), anastomotic devices, vascular catheter ports, vascular stents, clamps, embolic devices, wound drain tubes, ocular lenses, dental implants, hydrocephalus shunts, pacemakers and implantable defibrillators, needleless connectors, voice prostheses and the like. Also contemplated herein is the coating of surfaces found in the medical and dental environment with the compounds or compositions described herein. Such surfaces include the inner and outer aspects of various instruments and devices, whether disposable or intended for repeated uses. Such surfaces include the entire spectrum of articles adapted for medical use, including without limitation, scalpels, needles, scissors and other devices used in invasive surgical, therapeutic or diagnostic procedures; blood filters. Other examples will be readily apparent to practitioners in these arts.

Surfaces found in the medical environment also include the inner and outer aspects of pieces of medical equipment, medical gear worn or carried by personnel in the health care setting. Such surfaces can include surfaces intended as biological barriers to infectious organisms in medical settings, such as gloves, aprons and face shields. Commonly used materials for biological barriers are thermoplastic or polymeric materials such as polyethylene, dacron, nylon, polyesters, polytetrafluoroethylene, polyurethane, latex, silicone and vinyl. Other surfaces can include counter tops and fixtures in areas used for medical procedures or for preparing medical apparatus, tubes and canisters used in respiratory treatments, including the administration of oxygen, of solubilized drugs in nebulizers and of anesthetic agents. Other such surfaces can include handles and cables for medical or dental equipment not intended to be sterile. Additionally, such surfaces can include those non-sterile external surfaces of tubes and other apparatus found in areas where blood or body fluids or other hazardous biomaterials are commonly encountered. The compositions as described herein can be used on the surface of or within these medical devices to provide long term protection against colonization by single cell organisms and reduce the incidence of device-related infections.

The compositions as described herein can be directly incorporated into the polymeric matrix of the medical device at the polymer synthesis stage or at the device manufacture stage. The compositions can also be covalently attached to the medical device polymer. These and many other methods of coating medical devices are evident to one of ordinary skill in the art.

Additional surfaces that can be treated with the agents and compositions described herein include the inner and outer aspects of those articles involved in water purification, water storage and water delivery, and those articles involved in food processing. Thus, coating a solid surface of a food or beverage container to extend the shelf life of its contents is specifically contemplated herein.

Surfaces related to health can also include the inner and outer aspects of those household articles involved in providing for nutrition, sanitation or disease prevention. Thus, the compositions of as described herein can be used for removal of disease-causing microorganisms from external surfaces. These can include, for example food processing equipment for home use, materials for infant care, tampons, soap, detergents, health and skincare products, household cleaners and toilet bowls.

The surface can also be a laboratory article(s) including, but not limited to, microscopic slides, a culturing hood, a Petri dish or any other suitable type of tissue culture vessel or container known in the art.

Underwater surfaces include any water immersed surface, including ship/boat hulls (i.e., the body or frame of a ship or boat), submergence vehicles, navigational aids, screens, nets, constructions, floating or emplaced offshore platforms (e.g., docks), buoys, signaling equipment and articles which come into contact with sea water or salty water. Other underwater surfaces include structures exposed to sea water including pilings, marine markers, undersea conveyances like cabling and pipes, fishing nets, bulkheads, cooling towers, and any device or structure that operates submerged.

The compositions as described herein can be incorporated into marine coatings to limit undesirable marine biofouling. Thus, the anti-biofouling agents can be formulated so as not to contain toxic materials (such as heavy metals), and still retain their efficacy. The anti-biofouling paint comprising a composition as described herein can further contain binders(s), pigment(s), solvent(s) and additive(s) known to those of skill in the art.

The compositions described herein can also be used for providing antibacterial properties in cosmetics, to prevent spoiling of the product.

The compositions can further be used to provide an antibacterial effect to the mouth, teeth and gums, such as by incorporation in a toothpaste, mouthwash, or chewing gum.

Efficacy Measurement

The efficacy of a given treatment for a bacterial infection (including, infections such as carbapenem-resistant *Klebsiella pneumoniae*, methicillin-resistant *Staphylococcus aureus*, carbapenem-resistant *Escherichia coli*, among others) can be determined by the skilled clinician. However, a treatment is considered "effective treatment," as the term is used herein, if any one or all of the signs or symptoms of the bacterial infection is/are altered in a beneficial manner, or other clinically accepted symptoms or markers of disease are improved, or ameliorated, e.g., by at least 10% following treatment with an antibiotic agent selected using the methods and assays described herein. Efficacy can also be measured by failure of an individual to worsen as assessed by stabilization of the disease, or the need for medical interventions (i.e., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing progression of the infection; or (2) relieving the disease, e.g., causing regression of symptoms; and (3) preventing or reducing the likelihood of the development of the disease, or preventing secondary diseases/disorders associated with the infection (e.g., secondary infections, sepsis etc.).

An effective amount for the treatment of a disease means that amount which, when administered to a mammal in need thereof, is sufficient to result in effective treatment as that term is defined herein, for that disease. Efficacy of an agent can be determined by assessing physical indicators of the disease, such as e.g., pain, amount or presence of sputum, redness, localized swelling, fever, etc.

The present invention may be as defined in any one of the following numbered paragraphs.

1. A pharmaceutical composition for the treatment of an antibiotic-resistant bacterial infection, the composition comprising a therapeutically effective amount of a compound of Formula I or stereoisomers, tautomers, or pharmaceutically acceptable salts thereof and a pharmaceutically acceptable carrier;

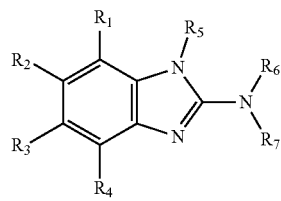

wherein:

$R_1$, $R_2$, $R_3$, and $R_4$ independently are H, alkyl, aryl, heteroaryl, heteroalkyl, cycloalkyl, heterocyclyl, acyl, allyl, OH, alkoxy, cyano, carboxy, $CF_3$, halide, NH(alkyl), NH(aryl) or $NH_2$;

$R_5$ is H, alkyl, aryl, heteroaryl, heteroalkyl, cycloalkyl, heterocyclyl, acyl, or allyl;

$R_6$ and $R_7$ are independently H, alkyl, aryl, heteroaryl, heteroalkyl, cycloalkyl, heterocyclyl, acyl, or allyl; or $R_6$ and $R_7$ together with the nitrogen they are bonded to form a heterocyclyl or a heteroaryl;

wherein any alkyl, alkenyl, cycloalkyl, heterocyclyl, heteroaryl or aryl is optionally substituted with 1, 2, or 3 groups selected from OH, CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)$alkyl$]_2$, $C(O)NH_2$, COOH, COOMe, acetyl, $(C_1$-$C_8)$alkyl, $O(C_1$-$C_8)$alkyl, $O(C_1$-$C_8)$haloalkyl, $(C_2$-$C_8)$alkenyl, $(C_2$-$C_8)$alkynyl, haloalkyl, thioalkyl, cyanomethylene, alkylaminyl, aryl, heteroaryl, substituted aryl, $NH_2$—C(O)-alkylene, NH(Me)-C(O)-alkylene, $CH_2$—C(O)-lower alkyl, C(O)-lower alkyl, alkylcarbonylaminyl, $CH_2$—[CH(OH)]$_m$—$(CH_2)_p$—OH, $CH_2$—[CH(OH)]$_m$—$(CH_2)_p$—$NH_2$ or $CH_2$-aryl-alkoxy; or wherein any alkyl, cycloalkyl or heterocyclyl is optionally substituted with oxo;

"m" and "p" are independently 1, 2, 3, 4, 5 or 6.

2. The pharmaceutical composition according to paragraph 1, wherein at least one of $R_1$, $R_2$, $R_3$, and $R_4$ is H and at least one of $R_1$, $R_2$, $R_3$, and $R_4$ is $NH_2$.

3. The pharmaceutical composition according to paragraph 1 or 2, wherein $R_5$ is a linear $C_1$-$C_6$ substituted alkyl where the terminal carbon is substituted with $N[(C_1$-$C_4)$alkyl$]_2$.

4. The pharmaceutical composition according to any one of paragraphs 1-3, wherein $R_6$ is H and $R_7$ is a methyl substituted with an aryl group.

5. The pharmaceutical composition according to paragraph 4, wherein $R_7$ is the para-(diethyl amino) benzyl substituted methyl group fragment A;

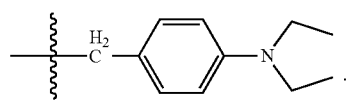

6. The pharmaceutical composition according to paragraph 5, wherein the compound is

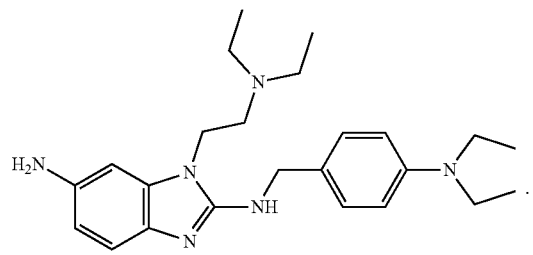

7. The pharmaceutical composition according to any one of paragraphs 1-6, wherein $R_6$ and $R_7$ together with the nitrogen they are bonded to form a substituted oxopyrazole, wherein $R_6$ is N and $R_7$ is an oxo group bonded to a carbon.

8. The pharmaceutical composition according to paragraph 6, wherein the compound is:

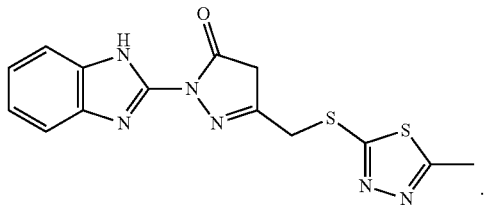

9. The pharmaceutical composition of any one of paragraphs 1-8, further comprising a therapeutically effective amount of an efflux pump inhibitor.

10. The pharmaceutical composition of paragraph 9, wherein the efflux pump inhibitor is phenylalanyl arginyl b-naphthylamide (PAβN).

11. The pharmaceutical composition of any one of paragraphs 1-10, wherein the composition is formulated for topical, inhalation or oral delivery.

12. A pharmaceutical composition for the treatment of an antibiotic-resistant bacterial infection, the composition comprising a therapeutically effective amount of a compound of Formula II or stereoisomers, tautomers, or pharmaceutically acceptable salts thereof and a pharmaceutically acceptable carrier;

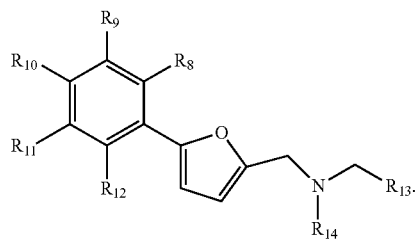

Wherein:

$R_8$, $R_9$, $R_{10}$, $R_{11}$, and $R_{12}$ independently are H, alkyl, aryl, heteroaryl, heteroalkyl, cycloalkyl, heterocyclyl, acyl, allyl, OH, alkoxy, cyano, carboxy, $CF_3$, halide, NH(alkyl), NH(aryl) or $NH_2$; $R_{14}$ and $R_{15}$ are independently H, alkyl, aryl, heteroaryl, heteroalkyl, cycloalkyl, heterocyclyl, acyl, or allyl;

wherein any alkyl, alkenyl, cycloalkyl, heterocyclyl, heteroaryl or aryl is optionally substituted with 1, 2, or 3 groups selected from OH, CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)$alkyl$]_2$, $C(O)NH_2$, COOH, COOMe, acetyl, $(C_1$-$C_8)$alkyl, $O(C_1$-$C_8)$alkyl, $O(C_1$-$C_5)$haloalkyl, $(C_2$-$C_8)$alkenyl, $(C_2$-$C_8)$alkynyl, haloalkyl, thioalkyl, cyanomethylene, alkylaminyl, aryl, heteroaryl, substituted aryl, $NH_2$—C(O)-alkylene, NH(Me)-C(O)-alkylene, $CH_2$—C(O)-lower alkyl, C(O)-lower alkyl, alkylcarbonylaminyl, $CH_2$—[CH(OH)]$_m$—$(CH_2)_p$—OH, $CH_2$—[CH(OH)]$_m$—$(CH_2)_p$—$NH_2$ or $CH_2$-aryl-alkoxy; or wherein any alkyl, cycloalkyl or heterocyclyl is optionally substituted with oxo;

"m" and "p" are independently 1, 2, 3, 4, 5 or 6.

13. The pharmaceutical composition according to paragraph 12, wherein at least one of $R_8$, $R_9$, $R_{10}$, $R_{11}$, and $R_{12}$ is a chloride or a bromide.

14. The pharmaceutical composition according to paragraph 12 or 13, wherein at least one of $R_8$, $R_9$, $R_{10}$, $R_{11}$, and $R_{12}$ is a methoxy.

15. The pharmaceutical composition according to any one of paragraphs 12-14, wherein $R_{13}$ is a 5 or 6 member cycloalkyl, heterocyclyl, aryl, or heteroaryl.

16. The pharmaceutical composition according to any one of paragraphs 12-15, wherein the compound is selected from the following compounds;

O06
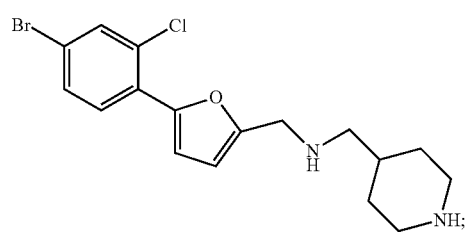

A06
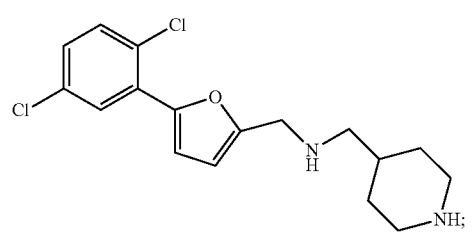

I17
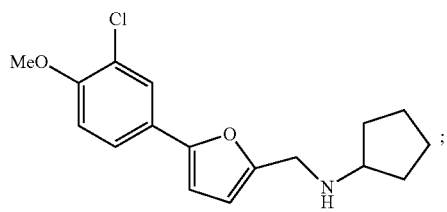

K05

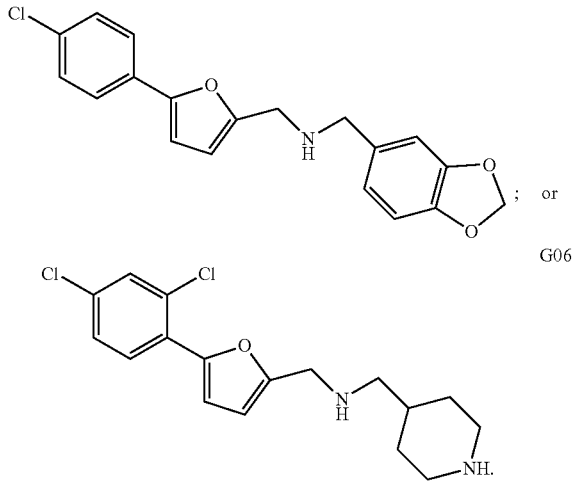

; or

G06

17. The pharmaceutical composition according to paragraph 16, wherein the compound is compound O06.

18. The pharmaceutical composition of any one of paragraphs 12-17, further comprising a therapeutically effective amount of an efflux pump inhibitor.

19. The pharmaceutical composition of paragraph 18, wherein the efflux pump inhibitor is phenylalanyl arginyl b-naphthylamide (PAβN).

20. The pharmaceutical composition of any one of paragraphs 12-19, wherein the composition is formulated for topical, inhalation, or oral delivery.

21. A pharmaceutical composition for the treatment of an antibiotic-resistant bacterial infection, the composition comprising a therapeutically effective amount of a compound of Formula III or stereoisomers, tautomers, or pharmaceutically acceptable salts thereof and a pharmaceutically acceptable carrier;

III
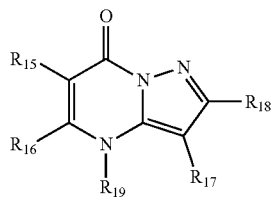

wherein:

$R_{15}$, $R_{16}$, $R_{17}$, and $R_{18}$ independently are H, alkyl, aryl, heteroaryl, heteroalkyl, cycloalkyl, heterocyclyl, acyl, allyl, OH, alkoxy, cyano, carboxy, $CF_3$, halide, NH(alkyl), NH(aryl) or $NH_2$;

$R_{19}$ is H, alkyl, aryl, heteroaryl, heteroalkyl, cycloalkyl, heterocyclyl, acyl, or allyl; wherein any alkyl, alkenyl, cycloalkyl, heterocyclyl, heteroaryl or aryl is optionally substituted with 1, 2, or 3 groups selected from OH, CN, SH, $SO_2NH_2$, $SO_2(C_1$-$C_4)$alkyl, $SO_2NH(C_1$-$C_4)$alkyl, halogen, $NH_2$, $NH(C_1$-$C_4)$alkyl, $N[(C_1$-$C_4)$alkyl$]_2$, $C(O)NH_2$, COOH, COOMe, acetyl, $(C_1$-$C_8)$alkyl, $O(C_1$-$C_8)$alkyl, $O(C_1$-$C_5)$haloalkyl, $(C_2$-$C_8)$alkenyl, $(C_2$-$C_8)$alkynyl, haloalkyl, thioalkyl, cyanomethylene, alkylaminyl, aryl, heteroaryl, substituted aryl, $NH_2$—C(O)-alkylene, NH(Me)-C(O)-alkylene, $CH_2$—

C(O)-lower alkyl, C(O)-lower alkyl, alkylcarbonylaminyl, CH$_2$—[CH(OH)]$_m$—(CH$_2$)$_p$—OH, CH$_2$—[CH(OH)]$_m$—(CH$_2$)$_p$—NH$_2$ or CH$_2$-aryl-alkoxy; or wherein any alkyl, cycloalkyl or heterocyclyl is optionally substituted with oxo;

"m" and "p" are independently 1, 2, 3, 4, 5 or 6.

22. The pharmaceutical composition according to paragraph 21, wherein at least one of R$_{15}$ or R$_{16}$ is an aryl group.

23. The pharmaceutical composition according to paragraph 22, wherein R$_{16}$ a halogenated aryl group.

24. The pharmaceutical composition according to any one of paragraphs 21-23, wherein at least one of R$_{17}$ or R$_{18}$ is an alkyl group and the other of R$_{17}$ or R$_{18}$ is an aromatic group.

25. The pharmaceutical composition according to any one of paragraphs 21-24, wherein the compound is selected from the following compounds;

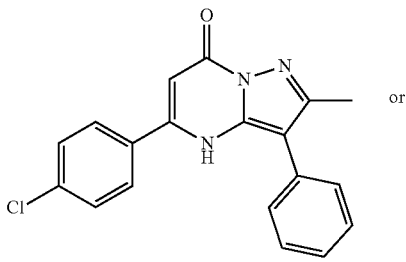

N08 or

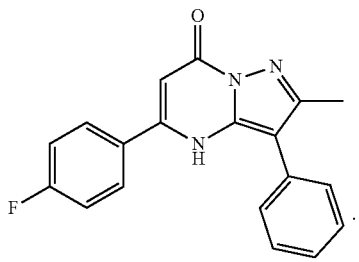

F02

26. The pharmaceutical composition according to paragraph 25, wherein the compound is compound N08.

27. A method for treating a bacterial infection in a subject, the method comprising administering a composition comprising a therapeutically effective amount of a compound of Formula I, II or III, in combination with a therapeutically effective amount of a bacterial efflux pump inhibitor to a subject having a bacterial infection, thereby treating the bacterial infection in the subject.

28. The method of paragraph 27, wherein the bacterial infection comprises an antibiotic-resistant bacterium.

29. The method of paragraph 27 or 28, wherein the compound of:
  (i) Formula I is C17,
  (ii) Formula II is O06, or
  (iii) Formula III is N08.

30. The method of any one of paragraphs 27-29, wherein the bacterial efflux pump inhibitor is PaβN.

31. The method of paragraph 28, wherein the antibiotic-resistant bacterium is a Gram negative bacterial strain.

32. The method of paragraph 31, wherein the Gram negative bacterial strain is a strain from the Enterobacteriaceae family.

33. The method of paragraph 31 or 32, wherein the antibiotic-resistant bacterium comprises a carbapenem-resistant strain of bacteria.

34. The method of any one of paragraphs 31-33, wherein the antibiotic-resistant bacterium comprises carbapenem-resistant *Klebsiella pneumoniae*, methicillin-resistant *Staphylococcus aureus* (MRSA), carbapenem-resistant *Escherichia coli, Acinetobacter baumanii,* or *Pseudomonas aeruginosa* PA01.

35. The method of any one of paragraphs 27-34, wherein the subject is a human.

36. The method of any one of paragraphs 27-35, wherein the compound of Formula I, II or III and/or the bacterial efflux pump inhibitor is administered topically, orally, by inhalation or intravenously.

37. The method of any one of paragraphs 27-36, wherein the compound of Formula I, II, or III and the bacterial efflux pump inhibitor are administered simultaneously or sequentially.

38. The method of any one of paragraphs 27-37, further comprising a step of diagnosing the subject with the bacterial infection.

39. A method for treating a bacterial infection, the method comprising administering a pharmaceutical composition of any one of paragraphs 1-26 to a subject having a bacterial infection, optionally comprising a an antibiotic-resistant bacterium.

40. Use of a composition of any one of paragraphs 1-26 in the treatment of a bacterial infection in a subject.

41. The use of paragraph 40, wherein the composition or treatment further comprises a bacterial efflux pump inhibitor.

42. The use of paragraph 40 or 41, wherein the bacterial infection comprises an antibiotic-resistant bacterium.

A compound having the embodiments will be more readily understood by reference to the following examples, which are included merely for purposes of illustration of certain aspects and embodiments of the present invention, and should not be construed as limiting. As such, it will be readily apparent that any of the disclosed specific constructs and experimental plan can be substituted within the scope of the present disclosure.

EXAMPLES

There is an urgent need for new antimicrobials to combat the inexorable rise of multi-drug resistant bacteria as the options for treatment of infections caused by carbapenem-resistant Gram-negative bacteria and, in particular, the carbapenem-resistant Enterobacteriaceae are limited [1]. For this reason, the Centers for Disease Control and Prevention as well as the World Health Organization have designated carbapenem-resistant Enterobacteriaceae a threat that merits the highest priority for research and development of new antibiotics [2]. The increasing incidence of infections caused by carbapenem-resistant (CR) *Klebsiella pneumoniae*, which belong to the Enterobacteriaceae family, is particularly concerning because a recent meta-analysis of reports published between 1999 and 2015 found that the worldwide mortality of patients infected by CR *K. pneumoniae* could be as high as 50% [3].

Gram-negative bacteria are intrinsically more resistant to antimicrobial compounds than Gram-positive organisms due to (i) the requirement for penetration of both the negatively charged outer and lipophilic inner membranes, (ii) stringent transcriptional and post-transcriptional control of porin expression in the outer membrane, and (iii) expression of multi-drug efflux pumps [4-6]. As a result of these barriers to the entry of small molecules into cells, many bioactive compounds discovered in cell-free, targeted screens do not retain their activity in whole cell assays [7]. For this reason, whole cell screens can be quite useful in identifying antimicrobials active against Gram-negative organisms. Here, a high-throughput, sensitive whole cell metabolic screen was used to identify compounds in fungal extracts and synthetic compound libraries with antimicrobial activity against carbapenem-resistant *Klebsiella pneumoniae*. Patulin, a known fungal metabolite that has been shown to inhibit bacterial quorum sensing and alanine racemase, was identified as the active component in the most potent fungal extracts [8]. Patulin was not studied patulin further due to its known toxicity [9, 10].

Three synthetic compounds termed O06, C17, and N08 were chosen for further study. Compound N08 was active against several resistant GNRs as well as methicillin-resistant *Staphylococcus aureus* (MRSA) and showed minimal toxicity to mammalian cells. However, compound N08 is susceptible to bacterial efflux and has a tendency to form aggregates in aqueous media. Compound C17, which was the least toxic to mammalian cells, had only moderate activity against GNRs, and compound O06, which was the most toxic to human cells, had limited antibacterial activity but inhibited sugar utilization. The antibiotics derived using the whole cell screen described herein are active against carbapenem-resistant *Klebsiella pneumoniae*.

Materials and Methods

Strains and media. Carbapenem-resistant *Klebsiella pneumoniae* strain ATCC BAA-1705 was used for the high throughput screen (HTS). A carbapenem-susceptible clinical strain of *Klebsiella pneumoniae* (Kp233) and a clinical isolate of *Acinetobacter baumanii* were used for antimicrobial susceptibility studies. *Pseudomonas aeruginosa* PA01 was provided by the laboratory of Dr. Simon Dove. MRSA and Group A *streptococcus* (GAS) were used in tests of minimum inhibitory concentrations (MIC). *K. pneumoniae*, *P. aeruginosa* and *Escherichia coli* strains were cultured in Luria-Bertani broth (LB, BD Difco). *Acinetobacter baumanii* and MRSA were grown in tryptic soy broth (TSB, Becton-Dickinson), and GAS was grown in Todd-Hewitt broth supplemented with 0.5% yeast extract (Becton-Dickinson). Cation-adjusted Mueller Hinton broth with 10 mg/L $Mg^{2+}$ and 20 mg/L $Ca^{2+}$(Becton-Dickinson, CAMHB) was used in MIC assays. CAMHB supplemented with 2.5% lysed horse blood was used for GAS. Where indicated, 40 μg/mL of the efflux pump inhibitor phenylalanine-arginine beta-naphthylamide (PaβN), Sigma) was added to the medium to inhibit the multi-drug efflux pumps of the Gram-negative bacterial species under study [11]. Where required, carbenicillin (Sigma) was added at 150 μg/mL for plasmid retention. Frozen stocks were maintained at −80° C. in 15% glycerol.

Fungal extract and chemical compound libraries. A library of desiccated fungal extracts was generously supplied by Dr. David Newman and Carol Haggerty at the Natural Products Branch of the National Cancer Institute and resuspended at a concentration of 15 mg/ml in dimethyl sulfoxide (DMSO). A chemical library comprised of compounds from the Targeted Diversity Library at ChemDiv and purchased and maintained by the Institute of Chemistry and Chemical Biology-Longwood (ICCB-Longwood) at Harvard Medical School was also screened. The Targeted Diversity Library consists of approximately 50,000 drug-like compounds built around 2,500 diverse chemical scaffolds. All compounds in this library were resuspended in DMSO yielding a concentration of 5 mg/mL and stored at −80° C.

High-throughput screen (HTS) based on sugar fermentation. Libraries were screened using a HTS that detects inhibitors of mannose fermentation by strain *K pneumonia* BAA-1705 in pH-DM medium [12]. In preparation for screening, a small amount of a frozen glycerol stock of *K. pneumoniae* was spread on an LB agar plate and incubated overnight at 37° C. A loopful of bacteria was collected, washed three times in normal saline (NS), and resuspended in NS to yield an optical density at 600 nm (OD600) of 0.016. The HTS was performed in a defined medium containing mannose (pH-DM, Table 1) and supplemented with thymol blue (0.006% w/v) and bromothymol blue (0.006% w/v). The pH was adjusted to 7.6 by adding sodium hydroxide to a final concentration of 1 mM. All reagents for the defined media were obtained from Sigma-Aldrich.

Wells of a 384-well plate were filled with 30 μL of pH-DM using a Matrix WellMate™ liquid handler (ThermoScientific). 100 nL of each test extract or compound dissolved in DMSO was added at the ICCB-Longwood facility by pin-transfer using a custom-built Epson robot. Columns 23 and 24 of each plate were set aside for controls. Column 23 received no compound and served as the negative control. Column 24 contained pH-DM supplemented with 50 μg/mL of gentamicin and served as the positive control. 10 μL of the bacterial suspension was added to plates to yield a final extract concentration of 37.5 μg/ml or a final compound concentration of 12.5 μg/ml. Plates were covered and incubated in stacks of 4 at 27° C. Each plate was screened in duplicate. To reduce evaporation from wells on the plate perimeter, the incubator was humidified with containers of deionized water. The A615 was measured on an Infinite 200 spectrophotometer (Tecan) at the start of the incubation (0 hr), after 7 hours (7 hr), and after 22 hours (22 hr). The results were plotted in the Dotmatics Vortex software suite to visualize heat map and scatterplot graphs.

TABLE 1

Composition of the defined medium used in the high-throughput system (HTS)

| Component | g/L | mM |
|---|---|---|
| Alanine | 0.3 | 3.37 |
| Arginine HCl | 0.2 | 0.95 |
| Cysteine | 0.02 | 0.17 |
| Glycine | 0.13 | 1.73 |
| Histidine HCl | 0.17 | 0.89 |
| Isoleucine | 0.3 | 2.29 |
| Leucine | 0.5 | 3.81 |
| Lysine | 0.5 | 3.42 |
| Methionine | 0.1 | 0.67 |
| Phenylalanine | 0.2 | 1.21 |
| Serine | 0.2 | 1.9 |
| Threonine | 0.2 | 1.68 |
| Tyrosine | 0.04 | 0.22 |
| Valine | 0.4 | 3.41 |
| $KH_2PO_4$ | 0.012 | 0.088 |
| $K_2HPO_4$ | 0.028 | 0.16 |
| $(NH_4)_2SO_4$ | 0.008 | 0.06 |
| KCl | 0.75 | 10 |
| $CaCl_2 \cdot 2H_2O$ | 0.05 | 0.34 |
| $MgSO_4 \cdot 7H_2O$ | 0.2 | 0.811 |
| $FeSO_4 \cdot 7H_2O$ | 0.00017 | 0.00061 |
| NaCl | 5.8 | 100 |
| Mannose | 4 | 22.2 |

Identification of patulin in active fractions of fungal extract F19. An aliquot of F19, an active fungal crude extract, was purified using reverse-phase high pressure liquid chromatography (RP-HPLC) with a Luna $C_{18}(2)$ 5μ 10×250 mm column (Phenomenex™) under the following gradient: holding 10% ACN+0.1% formic acid (FA)/90% $H_2O$+0.1% FA for 2 min then gradient to 100% ACN+0.1% FA over 20 min flowing at 3 mL/min to generate five fractions (A-E). Only fraction B exhibited activity and dereplication using high resolution mass spectrometry (HRMS) revealed patulin as the active component. All additional active fractions were screened for the presence of patulin using a low-resolution LCMS equipped with a Luna $C_{18}(2)$ 5μ 4.6×100 mm column (Phenomenex™) and run using the following gradient system: holding 10% $H_2O$/ACN+0.1% formic acid (FA) for 2 min then gradient to 100% ACN+0.1% FA over 17 min flowing at 0.7 mL/min. All 4 extracts analyzed with strong activity were confirmed to contain patulin.

Commercial supply of compound hits. Patulin was purchased from Cayman chemicals. Three prioritized synthetic compounds were also purchased. Compound O06 was purchased from ChemDiv under the catalog number 8019-0105. Compounds C17 and N08 were purchased from Vitas-M Laboratory under catalog numbers STK871080 and STK250799, respectively.

Dose-response assays. Two-fold serial dilutions of chemical compounds in pH-DM or LB broth as noted were prepared in the wells of a 384-well plate. The compounds ranged in concentration from 0.78 μg/mL to 50 μg/mL. Carbapenem-resistant K. pneumoniae strain BAA-1705 was prepared as described for the HTS, and 10 μL of the bacterial preparation was added to 30 μL of the compound suspensions Mannose fermentation was measured spectrophotometrically as described for the HTS in wells filled with pH-DM. Viable cell counts were measured in wells filled with LB broth.

Alamar Blue assay for cytotoxicity. HeLa S3 cells were cultured in Dulbecco's modified Eagle medium supplemented with 10% fetal bovine serum, 100 U/mL penicillin, and 100 μg/mL streptomycin. Each well of a 96-well microtiter plate (Nunclon Delta Surface, Thermo Scientific) was seeded with 10,000 cells in 100 μL of culture medium. Cells were incubated for 18 hr in a humidified incubator at 37° C. with 5% $CO_2$ to allow attachment. Compounds were added to the adherent cells to yield a final concentration of 13 and 107 μg/mL. Positive control wells contained 0.1% Triton X-100, carrier control wells contained DMSO, and negative control wells contained medium and cells without DMSO. After addition of compounds, 0.1% Triton, or DMSO, plates were returned to the incubator. Cell viability was measured by resazurin reduction. Alamar Blue reagent (Invitrogen) was added to the cells after a 1.5 hr incubation with the test compounds. Cells were incubated for 20 hr, and then fluorescence was measured using the Infinite 200 (Tecan) with excitation and emission wavelengths of 550 nm and 590 nm, respectively. To calculate viability, the average fluorescence value of Triton-treated positive control wells was subtracted from that of untreated wells or wells containing test compounds. These values were then divided by the average fluorescence of untreated wells to give cell viability as a percentage of the negative control.

Minimum inhibitory concentrations (MIC). To measure the MIC, two-fold dilutions of compounds were prepared in Mueller Hinton broth, resulting in concentrations ranging from 1.5 μg/mL to 192 μg/mL. Stationary phase bacteria were inoculated into CAMHB with or without the efflux pump inhibitor PAβN to yield a final $OD_{600}$ of 0.1 and then diluted 100-fold, resulting in a final cell density of approximately $1\times10^5$ CFU/mL. Fifty μL of the bacterial suspension was added to 50 μL of each compound-containing solution, resulting in a total volume/well of 100 The final concentration of compounds ranged from 0.75 μg/mL to 96 μg/mL, and each well contained approximately $5\times10^4$ CFU of the indicated bacterium. Compound N08 may not have been fully solubilized at the highest concentrations. Gentamicin ranging in concentration from 0.78 μg/mL to 100 μg/mL was included as a positive control in MIC assays. Levofloxacin and chloramphenicol are known substrates of the multi-drug efflux pumps of P. aeruginosa and K. pneumoniae, respectively [13-15]. Therefore, for assays performed with PaβN, levofloxacin concentrations between 3.9 ng/mL and 0.5 μg/mL and chloramphenicol concentrations between 9.8 μg/mL and 1.25 mg/mL were included as positive controls. Plates were covered and incubated for 18-20 hr at 37° C. Bacterial growth was visible as biomass collected at the bottom of the wells. The MIC reported is the lowest compound concentration that visually inhibited bacterial growth.

Compound impact on bacterial viability. Compound stocks maintained in DMSO were diluted in LB to achieve final compound concentrations of 100 μg/mL, and PAβN was used at 40 μg/mL. One hundred μL of each compound preparation was dispensed into the wells of a microtiter plate. Negative (untreated) wells contained LB with or without PAβN only.

Stationary phase cell viability. A glycerol stock of the carbapenem-susceptible clinical strain of K. pneumoniae (Kp233) was inoculated into 1.5 mL of LB and incubated overnight (approximately 18 hr) at 37° C. with shaking. Cells were washed twice with NS and then inoculated into the wells of a microtiter plate prepared as described above to achieve a final cell density of $1\times10^6$ CFU/ml. Cells were incubated statically at 37° C. for 4 hr, and viable counts were determined by plating.

Exponential phase cell viability. Overnight cultures of Kp233 were diluted 1:5,000 into 50 mL of LB broth and incubated at 37° C. with shaking at 200 rpm. Optical density was measured every 30 min until cells reached exponential phase (OD=0.4, $2\times10^8$ CFU/mL). These cells were also washed twice with NS and inoculated into the wells of a microtiter plate prepared as described above. Cells were incubated statically at 37° C. for 4 hr, and viable counts were determined by plating.

Morphometric analysis. Carbapenem-susceptible Kp233 were treated as described for stationary phase viability assays, with the exception that negative control wells contained no DMSO and no antimicrobials. Ampicillin (150 μg/mL) was used as a positive control. Cells were incubated statically at 37° C. for 4 hr. Thirty μL from each well was transferred into a 24-well plate filled with 300 μL of LB broth. Images were captured with a 40× magnification lens using a Nikon Eclipse TE2000-E microscope. Morphometric analysis was carried out using IPLab 4.0 software.

GFP fluorescence assays. To assess protein synthesis, plasmid pJBA110, encoding a variant green fluorescent protein (GFP) with a half-life of 40 min, was transformed into Kp233 to yield PW2127. Cells from the glycerol stock were spread on LB agar containing 150 μg/mL of carbenicillin and incubated at 37° C. for 18 hr. Cells were collected and washed twice with sterile NS. Each well of a 384-well clear-bottom plate with black walls was filled with LB containing $4\times10^5$ CFU of Kp233/pJBA110 and compounds at 1, 10, or 100 μg/mL. Fluorescence was measured every 30 min with excitation and emission wavelengths of 480 and 515 nm, respectively.

Results

Implementation and validation of a high-throughput screen for compounds with activity against carbapenem-resistant *Klebsiella pneumoniae*. Natural extracts were previously screened for activity against *V. cholerae* using an assay that measures sucrose fermentation and found it to be extremely sensitive and robust [16]. This assay depends upon the use of a defined reporter medium containing essential amino acids, the pH indicators bromothymol blue and thymol blue, and a fermentable sugar. In this medium, bacterial fermentation results in medium acidification leading to protonation of both pH indicators and a color change from green to yellow. This color change is easily detected spectrophotometrically as a decrease in the absorbance at 615 nm (A615). This aforementioned assay was then optimized for *K. pneumoniae* by using mannose rather than sucrose fermentation as the indicator of metabolic activity. *K. pneumoniae* mannose metabolism resulted in a decrease in $A_{615}$ after incubation at room temperature for 3-5 hr. The $A_{615}$ nadir was reached after approximately 7 hours, at the mid-exponential phase of growth, and had recovered considerably after 20 hours (FIG. 1A). Therefore, measurements were taken at 7 and 20 or 22 hours.

To validate the screen, two plates were obtained and tested from the Biomol 4 federal drug administration-approved known bioactive compound library available at the ICCB-Longwood Screening Facility. The Z' factor, a coefficient that reflects the separation of the positive and negative controls, was calculated using the following equation: $Z'=1-3(\sigma_p+\sigma_n)/|\mu_p-\mu_n|$, where $\sigma_p$ and $\sigma_n$ are the standard deviations and $\mu_p$ and $\mu_n$ are the means of the positive and negative controls, respectively [17]. A Z' factor of 0.7 or higher indicates a good to excellent assay. The Z' factor for these test plates was 0.750±0.068 (range 0.676-0.821). The pilot screen identified several known antibiotics as well as DNA-damaging antineoplastic agents with activity against *K. pneumoniae* (Table 2). This further validated our assay.

TABLE 2

Known bioactive compounds identified in the pilot HTS assay.

| Compound name Bioactive plates 3 + 4 (ICCB 2089, 2090) | Class |
|---|---|
| Rifamycin sv | Antibacterial |
| Rifampici | Antibacterial |
| Minocycline hydrochloride | Antibacterial |
| Doxycycline hydrochloride | Antibacterial |
| Clinafloxacin hydrochloride | Antibacterial |
| Sulfadiazine | Antibacterial |
| Gemcitabine hydrochloride | Antineoplastic |
| Doxifluridine | Antineoplastic |
| 5-fluorouracil | Antineoplastic, anti-metabolite |
| Floxuridine | Antineoplastic, anti-metabolite |
| Auranofin | Anti-inflammatory |

Figure 1B:
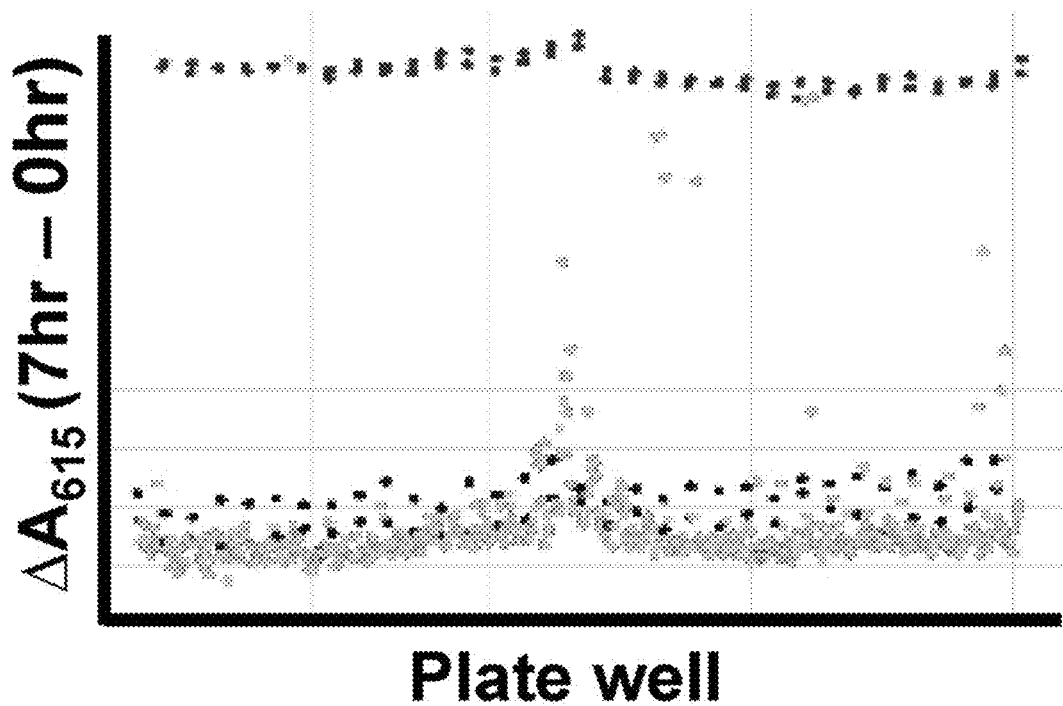
Figure 1C:
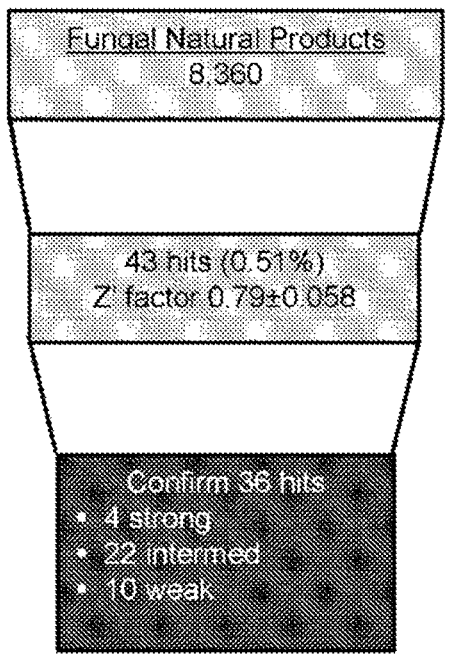
Figure 1D:
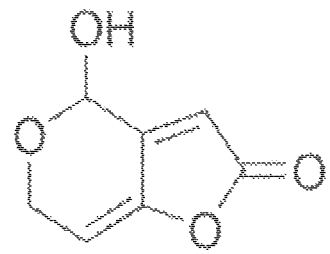
Figure 8:
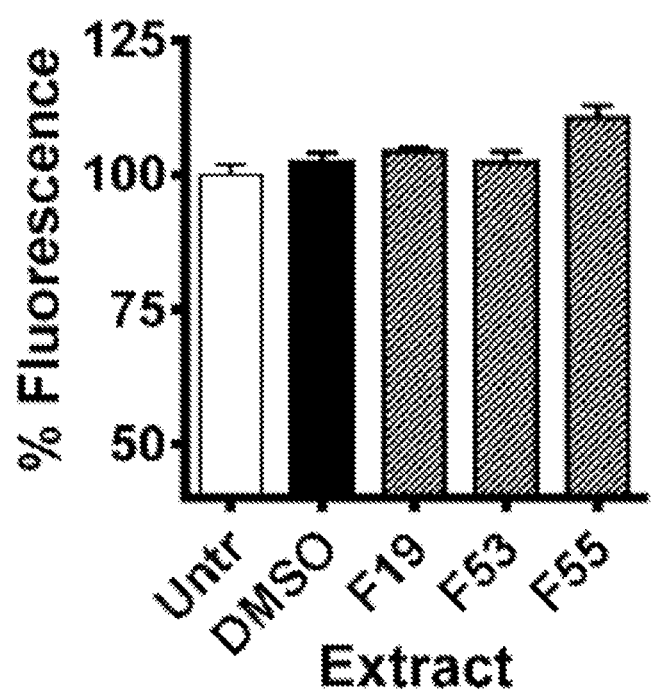
FIG. 8. Three fungal extract hits have no cytotoxic effects on HeLa cells. Extracts F19, F53, and F55 were incubated with HeLa cells for 20 hours. Viability was measured by resazurin reduction and expressed as the percent fluorescence compared to untreated cells. One of these, extract F19, was fractionated. The propensity of each fraction to inhibition fermentation and growth is shown in FIGS. 9A-9C.
Figure 9A:
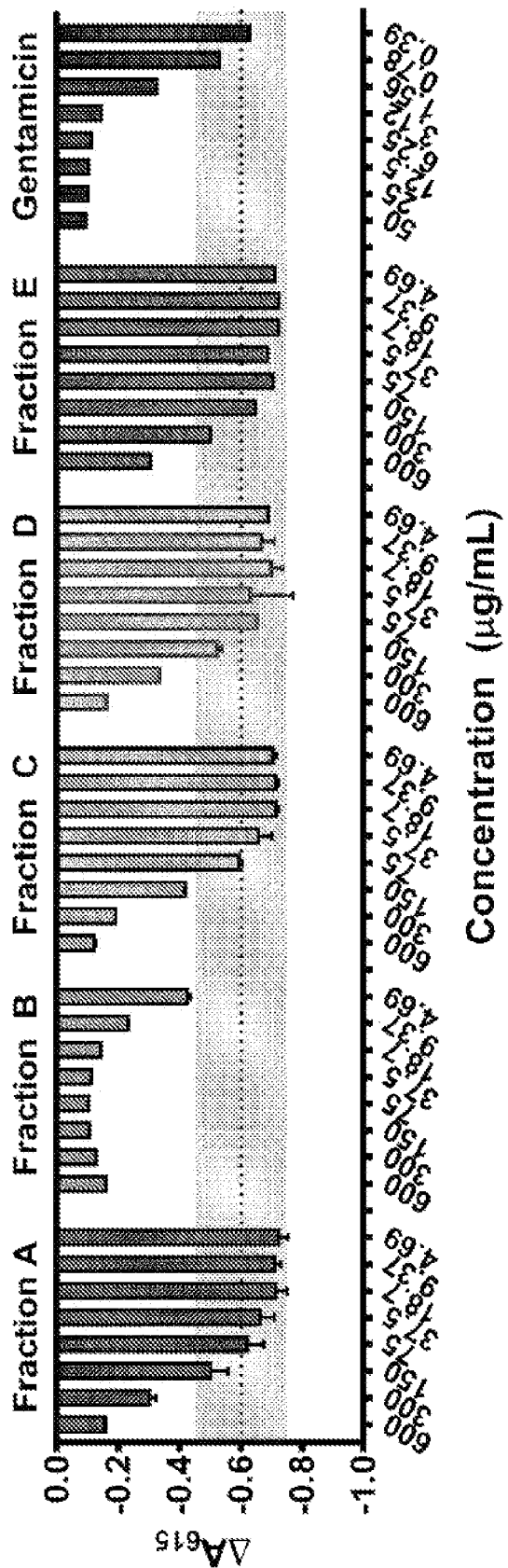
FIGS. 9A-9C. Inhibition of *K. pneumoniae* sugar fermentation and growth by fractions of fungal extract F19. Fractions derived from extract F19 were tested for FIG. 9A, inhibition of fermentation after 7 hr.
Figure 9B:
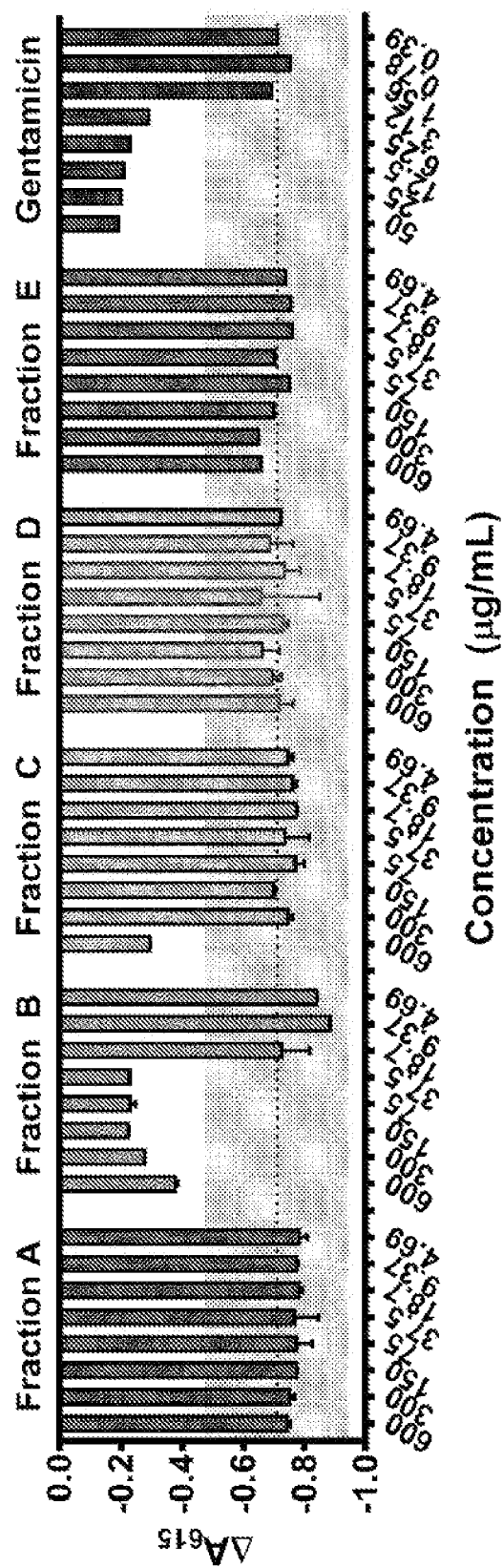
Figure 9C:
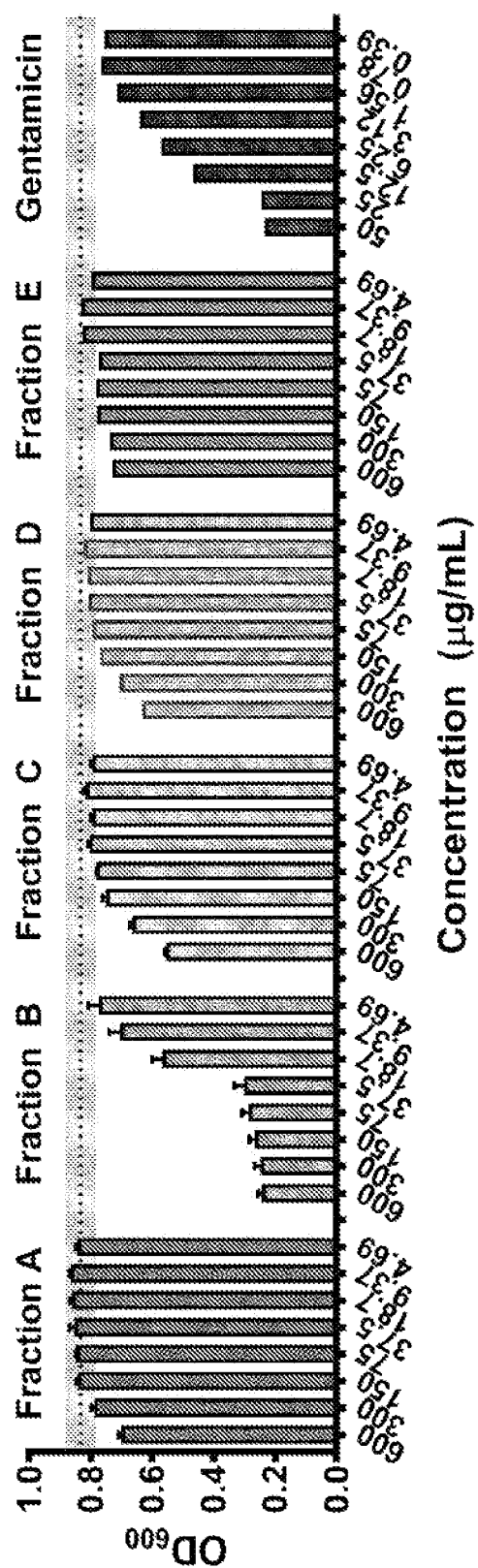

High-throughput screen of fungal extracts. The above-described assay was used in a HTS against carbapenem-resistant (CR) *K. pneumoniae* using a library of 8,179 fungal organic extracts supplied by the Natural Products Branch at the National Cancer Institute and selected based on previous evidence of antibacterial activity against *E. coli* [12]. For quality control, Z' factors were calculated using controls from replicate plates. Positive and negative controls were generally well-segregated (FIG. 1B), with the Z' factors for replicate plates ranging from 0.73 to 0.91. Plates with unacceptable Z' factors were repeated. For the fungal screen, strong hits were defined as those giving rise to measurements that fell within three standard deviations of the gentamicin positive control at both 7 and 20 hours. Medium hits fell just outside three standard deviations of the positive control at 7 hours but joined the negative control at 20 hours. Weak hits fell close to the negative control but not within three standard deviations of this measurement. The primary screen identified 43 fungal extracts with antibacterial activity (FIG. 1C). Of these, 36, including 4 strong hits, were confirmed in cherry pick assays. None of these extracts was found to be toxic to cultured HeLa cells (FIG. 8). Antibacterial activity was localized to fraction B, and the predominant component of this fraction was patulin (FIG. 1D). It was subsequently demonstrated that all strong hits also contained patulin. This finding likely reflects a lack of diversity in the natural product library along with the highly resistant nature of the *K. pneumoniae* strain under study. The patulin MIC for CR and carbapenem-sensitive (CS)-*K. pneumoniae* in rich medium was 18.75 and 9.38 μg/ml, respectively (Table 3). In defined medium, the MIC for both *K. pneumoniae* strains was 9.38 μg/mL.

TABLE 3

Minimum inhibitory concentrations measured for patulin (μg/mL)

| Bacterial Strain | LB broth | Defined Medium |
|---|---|---|
| CR-*K. pneumoniae* (ATCC BAA-1705) | 18.75 | 9.38 |
| *K. pneumoniae* Kp233 (a carbapenem-susceptible clinical strain of *K. pneumoniae*) | 9.38 | 9.38 |

Patulin has not previously been shown to inhibit the growth of CR *K. pneumoniae*. However, it is a secondary fungal metabolite with known antibacterial activity and toxicity [18, 19], thus validating the high throughput screen.

Figure 2A:
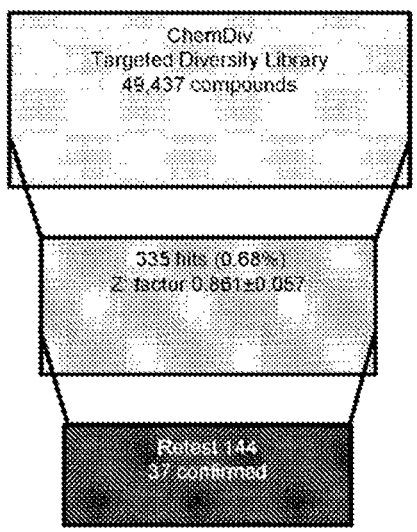
FIGS. 2A-2C. A high-throughput screen based on bacterial fermentation identifies compounds active against multidrug resistant *Klebsiella pneumoniae*.

High-throughput screen of chemical compounds. Given the uncertainties intrinsic to natural extracts screens, the assay described herein was next used to screen chemical compounds from the Chem Div Targeted Diversity Library. This library consists of small molecules with drug-like properties designed to inhibit known cellular targets including ion channels and enzymes such as kinases and proteases. Compounds from this collection were used at a final concentration of 12.5 μg/ml, and each compound was tested in duplicate. In the primary chemical screen, compounds were considered hits if the well $\Delta A_{615}$, defined as the difference in absorbance at 615 nm between hours 0 and 7 of the assay, exceeded the mean $\Delta A_{615}$ of the negative control by more than 3 standard deviations. This calculation was referred to as the result numeric. Detailed results of the primary HTS of the Chem Div library are summarized in FIG. 2A.

Figure 2B:
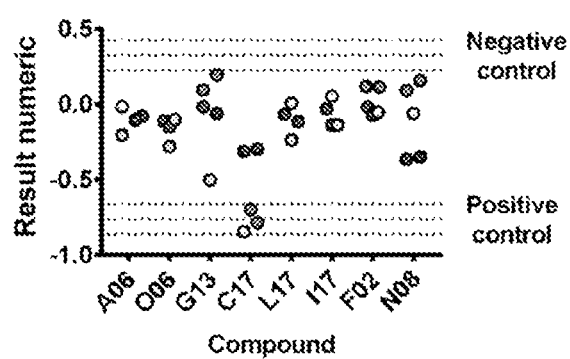
Figure 2C:
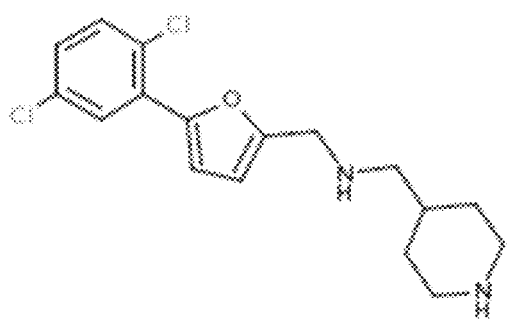
Figure 2C:
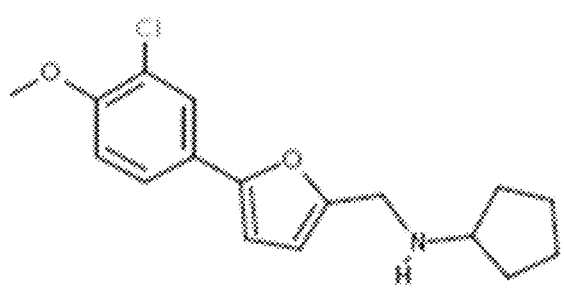
Figure 2C:
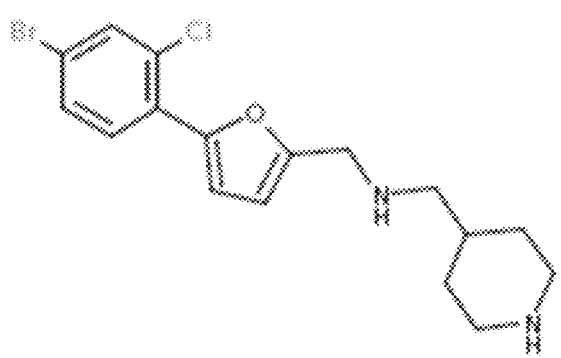
Figure 2C:
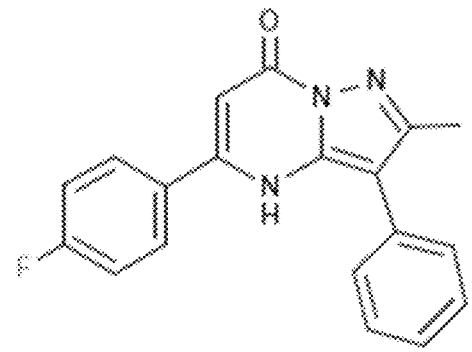

144 cherry-picked compounds were re-tested initially using an HP D300 digital dispenser with T8 cassettes to generate dose-response curves for 32 compounds, including the 28 strongest hits from the primary screen. However, only one hit, subsequently designated C17, showed significant activity when dispensed by the HP D300 (FIG. 2B). It was hypothesized that many of the cherry picked compounds had formed small aggregates that obstructed the nozzles of the HP D300 leading to little or no compound release. Therefore, the inventors reverted to dispensing these compounds manually in a 200 nl volume. Using this approach, 37 compounds, amounting to 25.6% of those tested, reached the result numeric threshold set for compound hits. The results numeric in the primary and cherry-pick screens for the eight most active compounds are shown in FIG. 2B, and the structures of these compounds are shown in FIG. 2C.

Figure 3A:
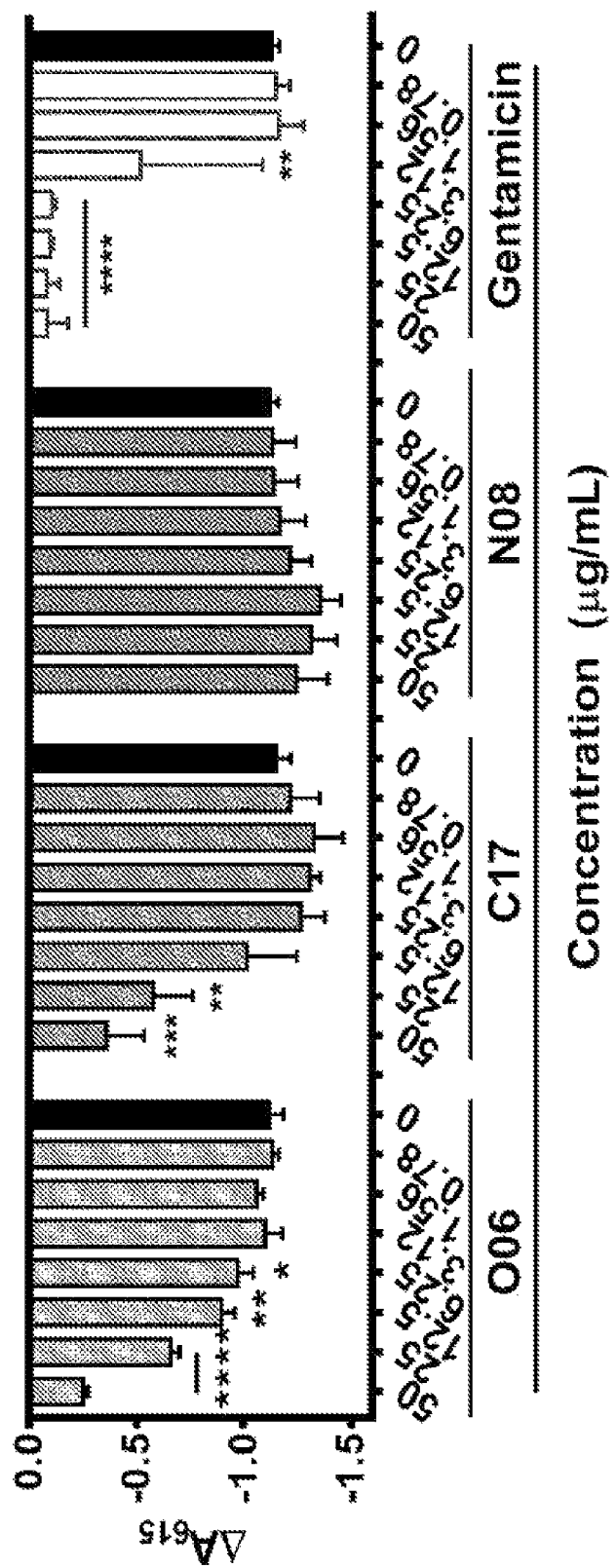
FIGS. 3A-3B. CR-*K. pneumoniae* fermentation and growth inhibition by three synthetic compounds identified in the high-throughput screen. Dose-dependent inhibition of FIG. 3A, mannose fermentation in DM-pH and FIG. 3B, growth represented by CFU/ml after 22 hr of culture in LB broth $(CFU/ml)^f$ divided by the CFU/ml at time 0 $(CFU/ml)^i$. * p≤0.05,  p≤0.01, * p≤0.001, **** p≤0.0001, ns p>0.05 using ordinary one-way ANOVA followed by Dunnett's multiple comparison test. The mean of three independent replicates is shown. Error bars represent the standard deviation. Gentamicin was included as a positive control.
Figure 3B:
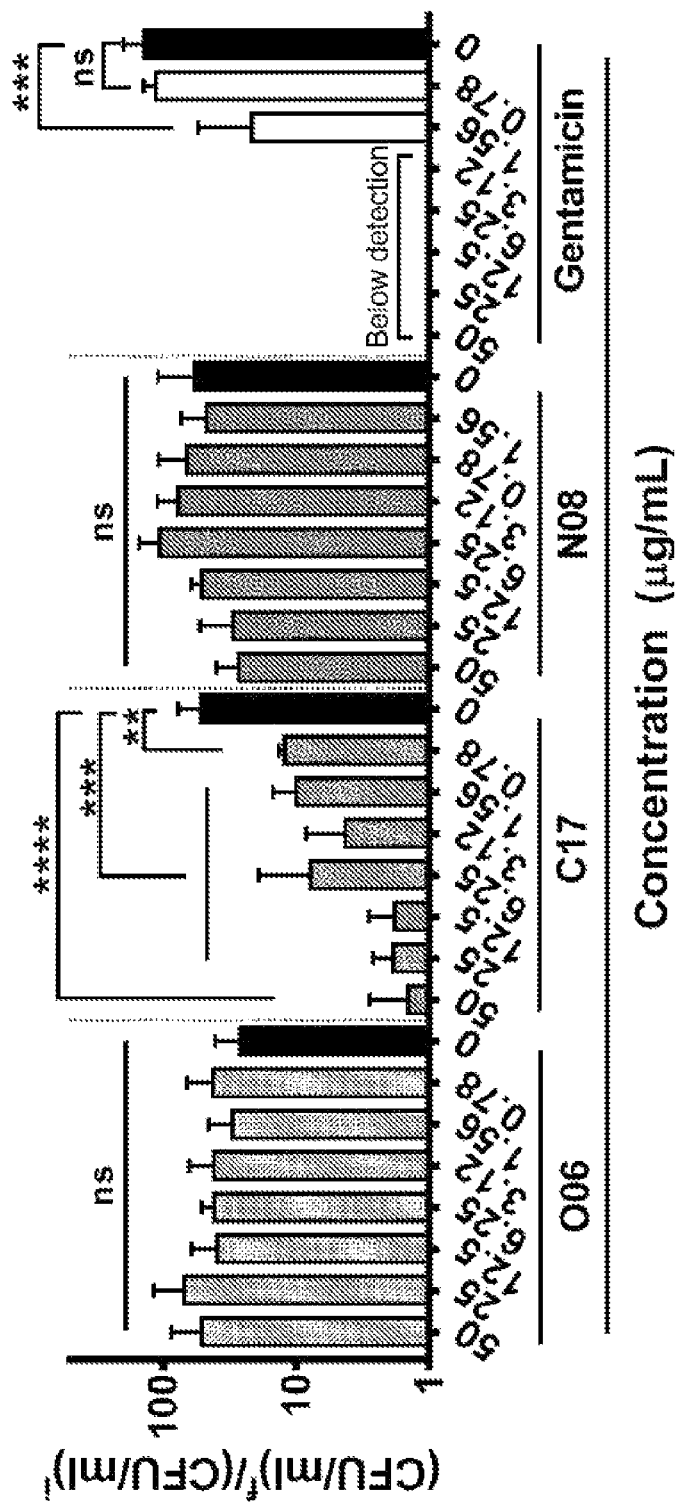
Figure 4A:
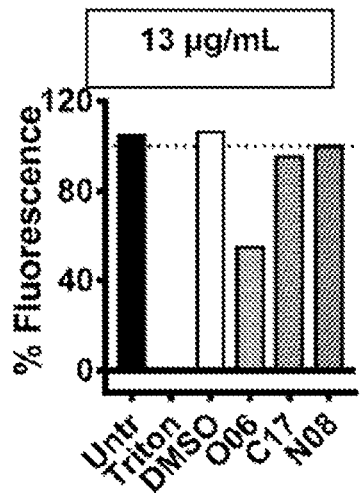
FIGS. 4A-4D. Toxicity of compounds for mammalian cells. HeLa S3 cells were incubated in media containing either compounds or vehicle for 20 hr. Viability was measured by resazurin reduction and expressed as the percent fluorescence compared to untreated cells at (FIGS. 4A & 4B) 13 µg/mL and (FIGS. 4C & 4D) 107 µg/mL. Cells incubated with medium containing DMSO and 0.1% Triton X-100 were included as negative and positive controls, respectively. Untr: untreated. Dotted horizontal line indicates 100% viability.
Figure 4B:
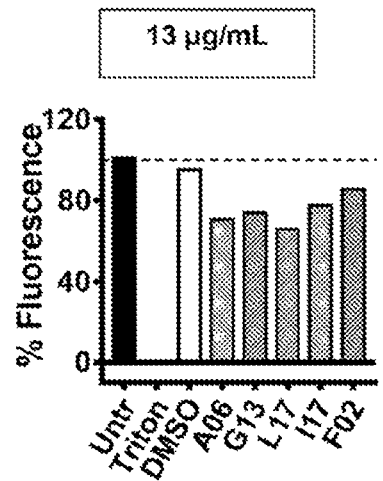
Figure 4C:
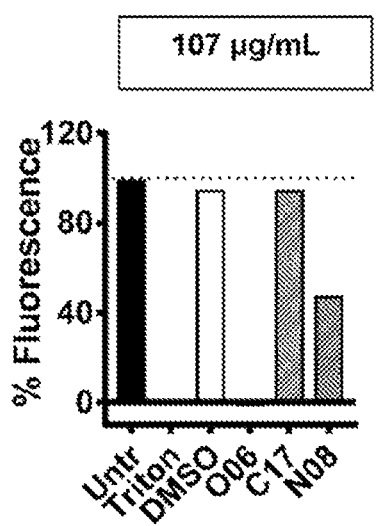
Figure 4D:
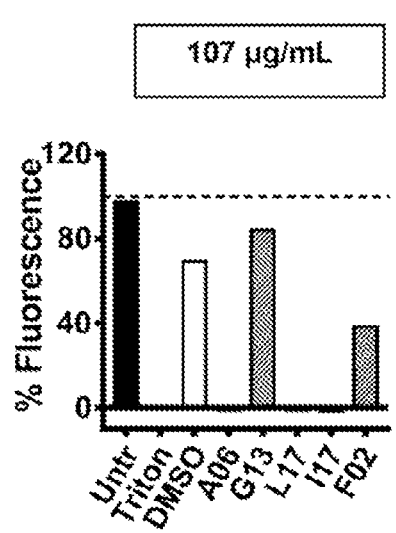
Figure 10:
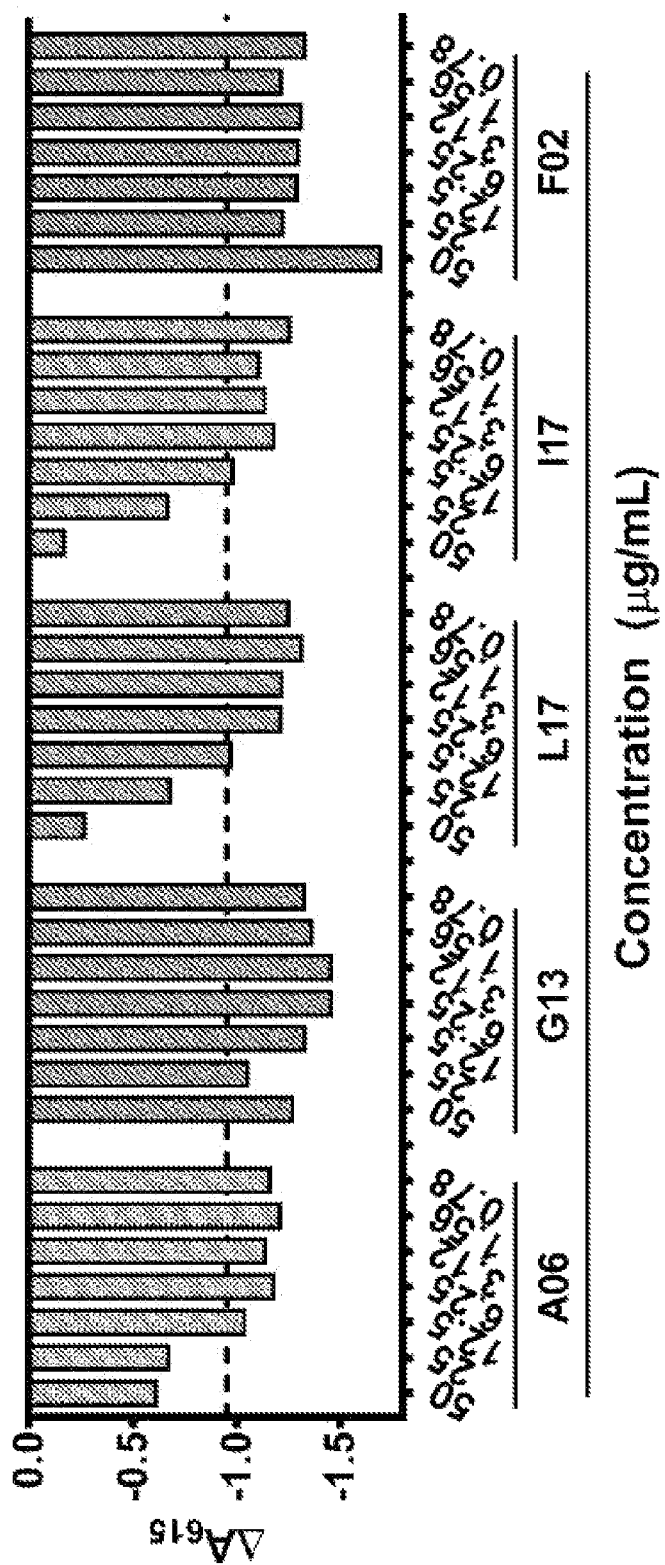
FIG. 10. Inhibition of fermentation by additional compounds. Inhibition of mannose fermentation by additional compounds at 22 hr.

Correlation of fermentation and growth inhibition. Further investigation of these compounds required the purchase of additional material from commercial vendors. First, the ability of these new compound preparations to inhibit fermentation was established. As shown in FIG. 3A and FIG. 10, only compounds O06 and C17 inhibited fermentation at 22 hours at concentrations similar to those used in the primary and cherry-pick screens. One possibility is that the other six compounds aggregated at higher concentrations or were not stable over the course of the experiment. Compound C17, which showed activity in the cherry-pick screen regardless of the method by which it was dispensed, inhibited growth of CR K. pneumoniae at the concentrations tested (FIG. 3B).

Toxicity to human cells. As a preliminary test of the toxicity of these compounds to mammals, eight compounds were incubated at concentrations of 13 and 107 µg/mL with HeLa S3 cells for 20 hours in the presence of resazurin. At this point, the fluorescence at 585 nm was measured. The reduction of resazurin to resorufin can be monitored by fluorescence at 585 nm and is indicative of aerobic respiration and, therefore, cell viability. Untreated cells and cells treated with the surfactant Triton X-100 served as controls. As shown in FIG. 4, compound C17 and G13 were not toxic at either concentration. Compounds N08 and F02 were only moderately toxic at the higher concentration, while other compounds were quite toxic at the higher concentration.

After considering activity in the primary and secondary screens and the extent of toxicity to human cells, the inventors focused on compounds O06, C17, and N08.

Spectrum of activity of prioritized compounds. To determine the spectrum of activity of compounds O06, C17, and N08, the MIC of each compound was measured against the multi-drug-resistant Gram-negative rods (GNR) *Acinetobacter baumanii*, *Pseudomonas aeruginosa*, and CR *K. pneumoniae*, susceptible GNR strains including two uropathogenic *E. coli* (UPEC) strains and one *K. pneumoniae* strain, and the Gram-positive cocci (GPC) MRSA and GAS (Table 4). The activity of compounds O06 and C17 against the GPCs and GNRs tested was comparable, indicating that the drug efflux specific to GNRs may not be a significant component of resistance. In contrast, while the GNRs were relatively resistant to compound N08, MRSA was quite sensitive. It was hypothesized that efflux might be an important mechanism of resistance to compound N08. To test this, the efflux pump inhibitor phenylalanine-arginine β-naphthylamide (PAβN) was used in strains of *P. aeruginosa* and *K. pneumoniae*, which first showed that the MICs of levofloxacin and chloramphenicol were reduced 16- and 32-fold in *P. aeruginosa* and *K. pneumoniae*, respectively (Table 4). Next, PAβN was tested with the identified compounds and again tested bacterial susceptibility. As predicted, addition of PAβN minimally decreased the resistant GNR MIC of compounds O06 and C17. In contrast, addition of PAβN reduced the MIC of N08 against resistant GNR by 1-2 logs (Table 4), confirming the hypothesis that efflux is a major mechanism of GNR resistance.

TABLE 4

Minimum inhibitory concentration (MIC) of compounds O06, C17, and N08 against panel of drug-resistant Gram-negative and Gram-positive bacteria. Addition of the efflux inhibitor phenylalanine-arginine β-naphthylamide (PAβN) improves the MIC for Gram negative organisms. (Cm: chloramphenicol; Lev: levofloxacin).

| | Compound (µg/mL) | | | | | | | | | |
|---|---|---|---|---|---|---|---|---|---|---|
| | O06 | | C17 | | N08 | | Cm | | Lev | |
| PAβN (40 µg/mL) | − | + | − | + | − | + | − | + | − | + |
| Multi-drug resistant bacterial strains | | | | | | | | | | |
| *A. baumanii* | 48 | 24 | >96 | 24 | >96 | 1.5 | — | — | — | — |
| *P. aeruginosa* PA01 | >96 | 24 | >96 | 48 | >96 | 12 | — | — | 0.25 | 0.015 |
| CR-*K. pneumoniae* (ATCC BAA-1705) | 96 | 96 | 96 | 48 | >96 | 6 | 1250 | 39 | — | — |
| MRSA | 48 | N/A[a] | 24 | N/A[a] | <0.75 | N/A[a] | — | — | — | — |
| Susceptible bacterial strains | | | | | | | | | | |
| *K. pneumoniae* Kp233[b] | 96 | — | 48 | — | >96 | — | <9 | — | 0.031 | — |
| *E. coli* urine isolate EC235[c] | 96 | — | 96 | — | >96 | — | <9 | — | 0.015 | — |
| *E. coli* urine isolate EC236[c] | 96 | — | 96 | — | >96 | — | <9 | — | 0.015 | — |
| Group A streptococcus | 48 | N/A[a] | 96 | N/A[a] | >96 | N/A[a] | — | — | — | — |

[a]Combination of compound with PAβN was not tested in Gram-positive organisms because they do not express resistance-nodulation-division (RND) class of multidrug efflux pumps targeted by PAβN.
[b]A carbapenem-susceptible clinical strain of *K. pneumoniae*
[c]Antibiotic-sensitive clinical isolates of uropathogenic *E. coli*

Figure 5A:
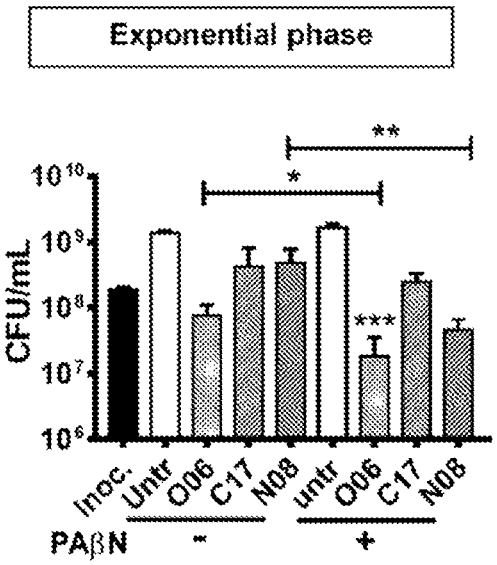
FIGS. 5A-5B. With efflux pump inhibition, compound O06 and N08 significantly decrease the viability of both exponential and stationary phase *K. pneumoniae*. CFU/ml was determined after a 4 hr treatment with the indicated compounds at a concentration of 100 µg/mL in the presence or absence of PAβN (40 µg/ml) of FIG. 5A, exponential phase and FIG. 5B, stationary phase *K. pneumoniae*. The mean of three independent experimental replicates is displayed. Error bars represent the standard deviation. ** p≤0.0001,  p≤0.01, * p<0.05, ns p>0.05 compared with the inoculum. Ordinary one-way ANOVA of log transformed data followed by Sidak's multiple comparison test was used to calculate statistical significance. Compound-treated cultures were compared to the relevant inoculum and +/- PAM treatments were compared for each compound. Inoc, inoculum, Untr, untreated.
Figure 5B:
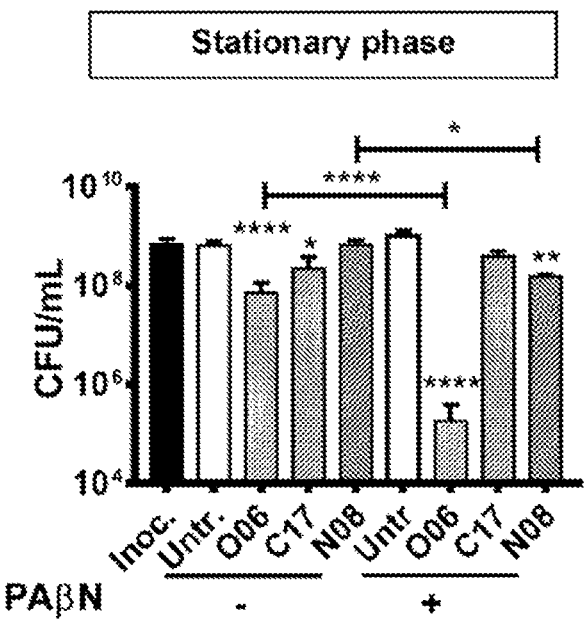

Compound impact on bacterial viability. The most effective antibiotics decrease the viability of both actively dividing and stationary phase cells. To compare the activity of each compound in the exponential and stationary phases of growth, LB-grown cultures of a carbapenem-susceptible *K. pneumoniae* clinical strain (Kp 233) in each phase of growth were incubated for 4 hours with 100 µg/mL of each compound alone or in combination with PAβN (FIG. 5). After 4 hr, colony forming units (CFU) were enumerated. The CFU of untreated exponential phase cultures increased approximately 10-fold during the incubation period, while those of stationary phase cultures remained unchanged. Compound O06, in particular, decreased the viability of both exponential and stationary phase cells. Furthermore, the efflux pump inhibitor PaβN significantly potentiated the killing activity of both compounds O06 and N08 (FIG. 5).

Figure 11:
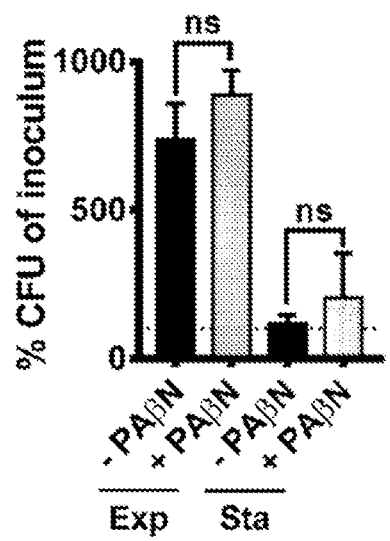
FIG. 11. The efflux pump inhibitor phenylalanine-arginine p-naphthylamide (PAβN) does not affect bacterial viability. Colony forming units of *K. pneumoniae* harvested in exponential (Exp) or stationary (Sta) phase and incubated for 4 hr in medium containing the efflux pump inhibitor phenylalanine-arginine p-naphthylamide (PAβN, 40 µg/mL) alone. Dotted horizontal line represents the number of colony forming units (CFU) prior to incubation. Error bars represent the standard deviation. A student's t-test was used to calculate statistical significance. ns not significant.

As a control, it was confirmed that PAβN, by itself, did not decrease the viability of either exponential or stationary phase cells (FIG. 11).

Figure 6A:
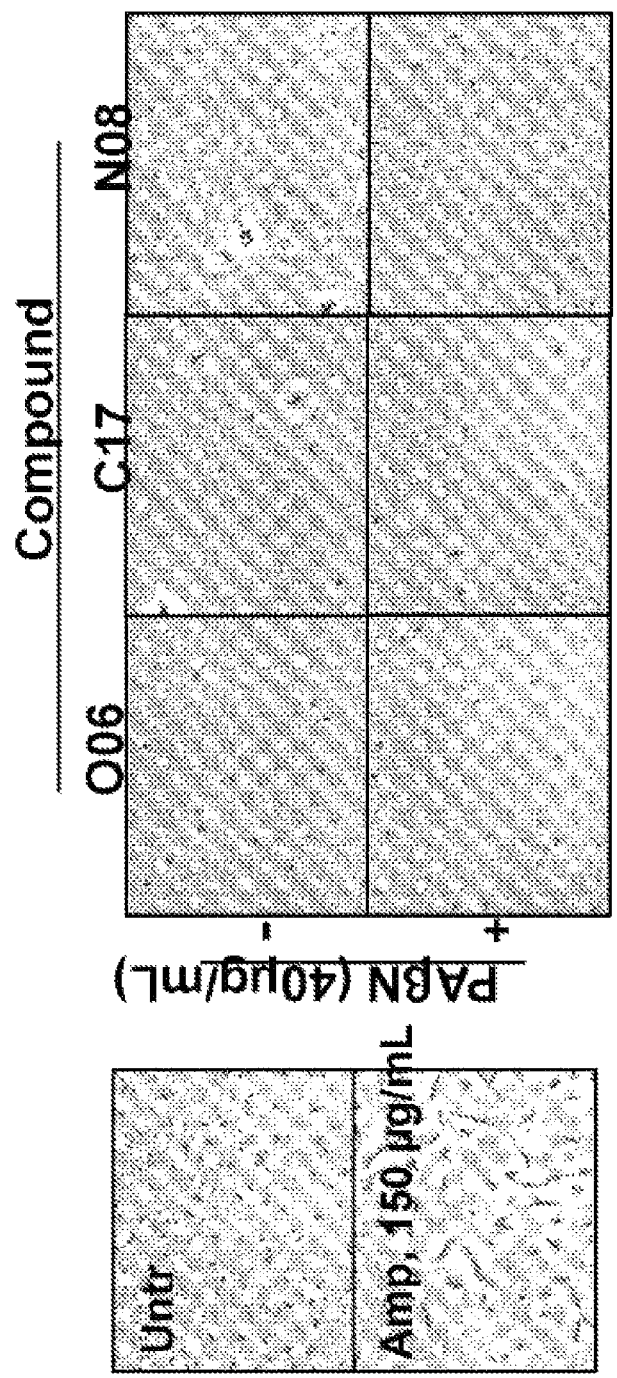
FIGS. 6A-6C. Compounds do not induce changes in cell morphology. Stationary phase cells were sub-cultured into fresh media containing 100 µg/mL of each compound in the presence or absence of the efflux inhibitor PAβN and incubated for 4 hr.
Figure 6B:
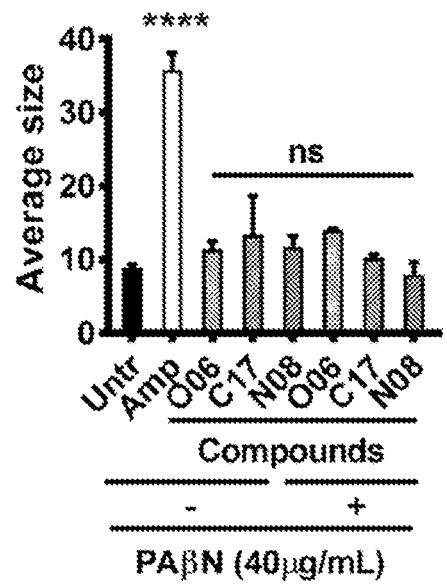
Figure 6C:
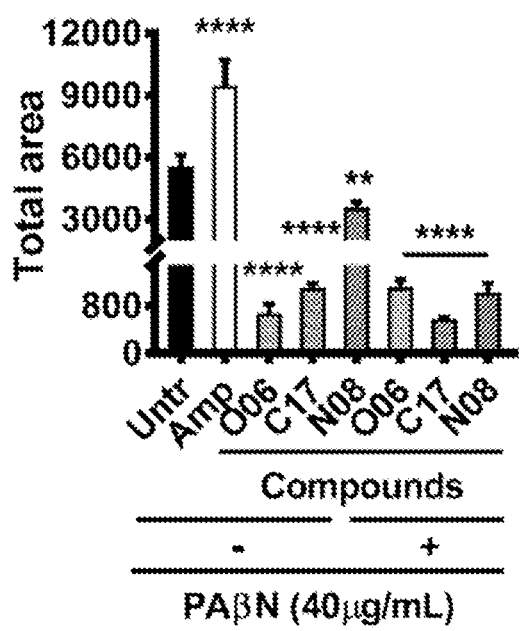
Figure 7A:
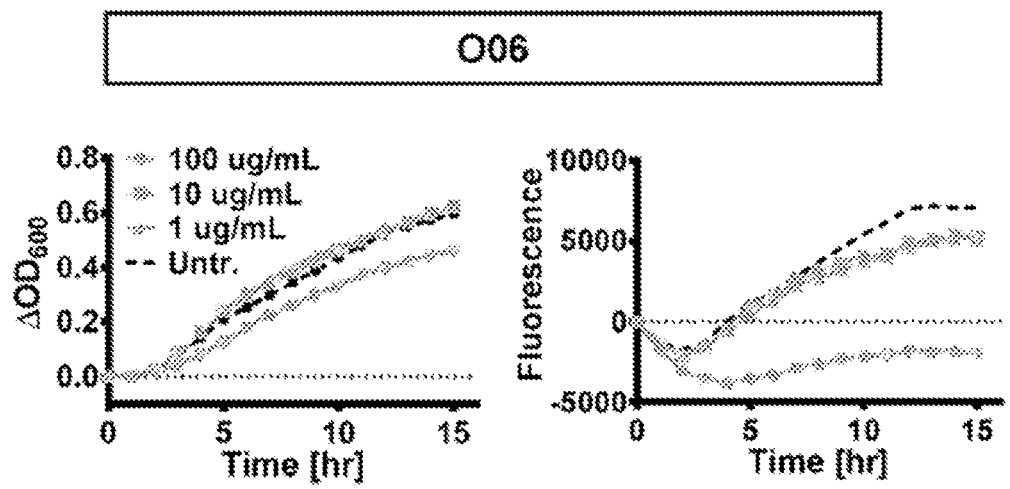
FIGS. 7A-7D. In the presence of compound N08, GFP fluorescence is decreased at concentrations that do not impair growth. Overnight cultures were sub-cultured into fresh LB media containing the indicated concentrations of compound O06, C17, N08, or gentamicin and incubated for 15 hr at 37° C. Fluorescence was measured every 30 min with excitation at 480 nm and emission at 515 nm. Growth was measured by optical density (OD) at 600 or 655 nm. Fluorescence and OD were normalized to the initial level detected at 0 hr to depict change in signal relative to time. Growth and fluorescence in cells treated with FIG. 7A, compound O06.
Figure 7B:
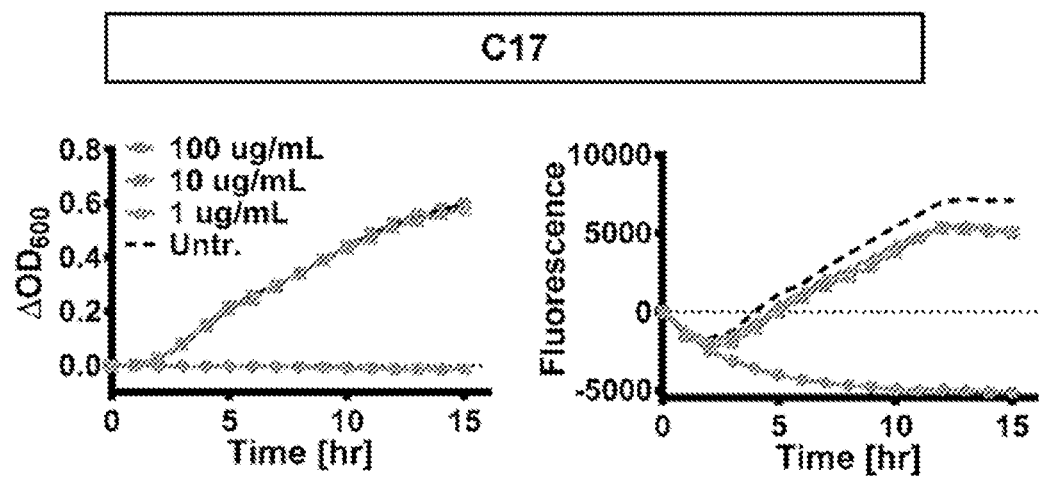
Figure 7C:
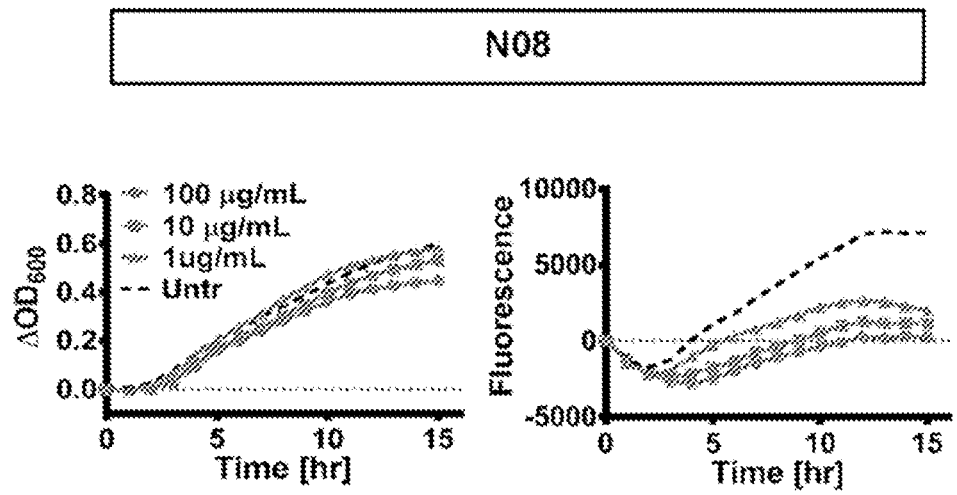
Figure 7D:
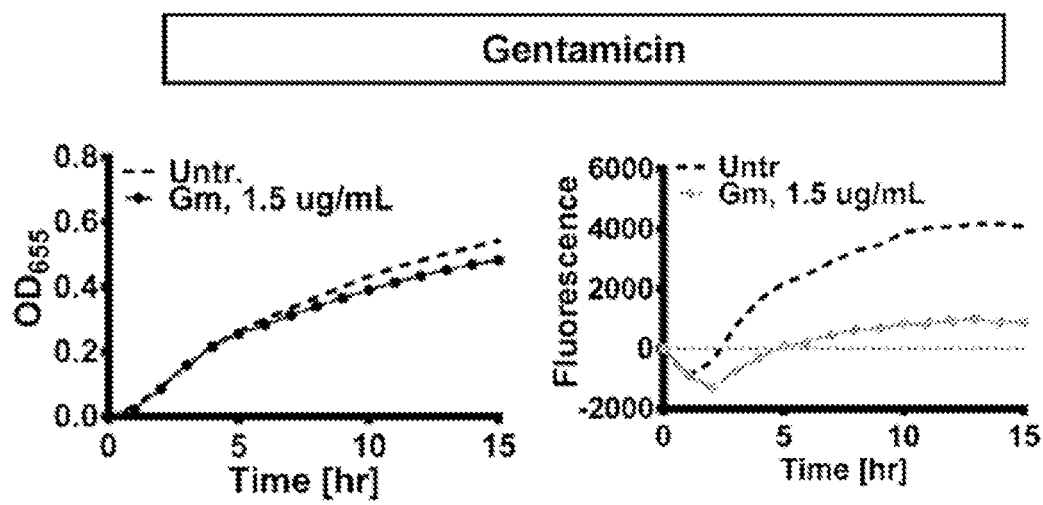

Compounds O06, C17, and N08 do not significantly alter cell shape. β-lactam antibiotics, which target peptidoglycan synthesis by associating with penicillin-binding proteins, dramatically alter bacterial cell morphology and are bactericidal [22, 23]. To uncover evidence for a similar mechanism of action, cell morphology was examined by phase contrast microscopy after exposure of a carbapenem-susceptible strain of *K. pneumoniae* (Kp233) to the identified compounds alone or with PAβN. As a positive control, stationary phase cells were exposed to 150 µg/mL of ampicillin or 100 µl/ml of each compound for 4 hr and then visualized by phase contrast microscopy (FIG. 6A). The average cell area and cumulative area covered by cells were quantified by morphometric analysis (FIGS. 6B and 6C). As expected, cells treated with ampicillin formed filaments with significantly increased average particle size as compared with untreated cells. However, while all compounds in combination with PAβN caused a decrease in total area covered by cells consistent with growth inhibition, none of these compounds significantly altered cell size or morphology. These results indicate that none of these compounds act by a mechanism similar to that of the beta-lactam antibiotics.

It was previously hypothesized that compound N08 was insoluble in aqueous media. Supporting this, particulate matter was observed in micrographs of bacteria treated with this compound but not those of bacteria treated with C17 or O06 (FIG. 6A). Thus, it was concluded that experiments using medium supplemented with concentrations of N08 close to or exceeding 100 µg/mL may not accurately reflect the concentration of compound in solution.

Figure 12A:
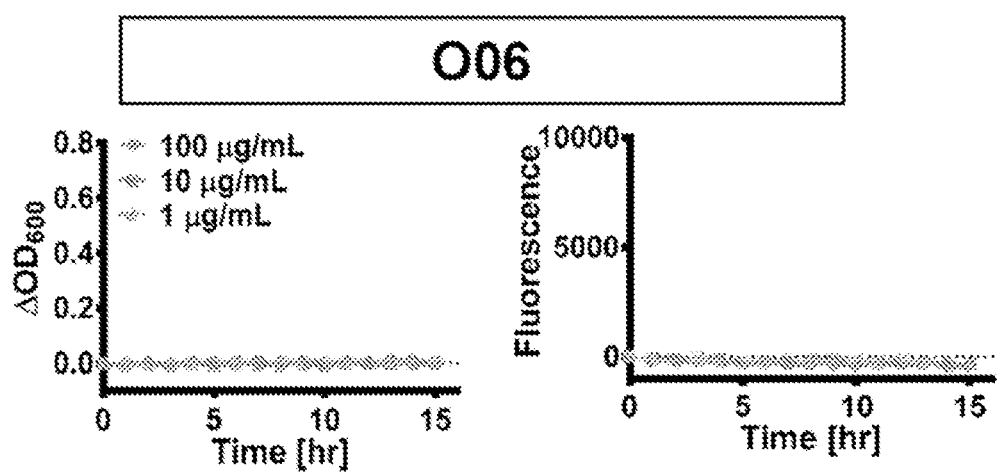
FIGS. 12A-12C. Synthetic compounds O06, C17, and N08 do not contribute to background fluorescence at the excitation and emission spectra of GFP. Compounds diluted into LB medium were incubated for 15 hr at 37° C. Fluorescence (excitation at 480 nm and emission at 515 nm) and OD600 were measured every 30 min with FIG. 12A, Compound 006.
Figure 12B:
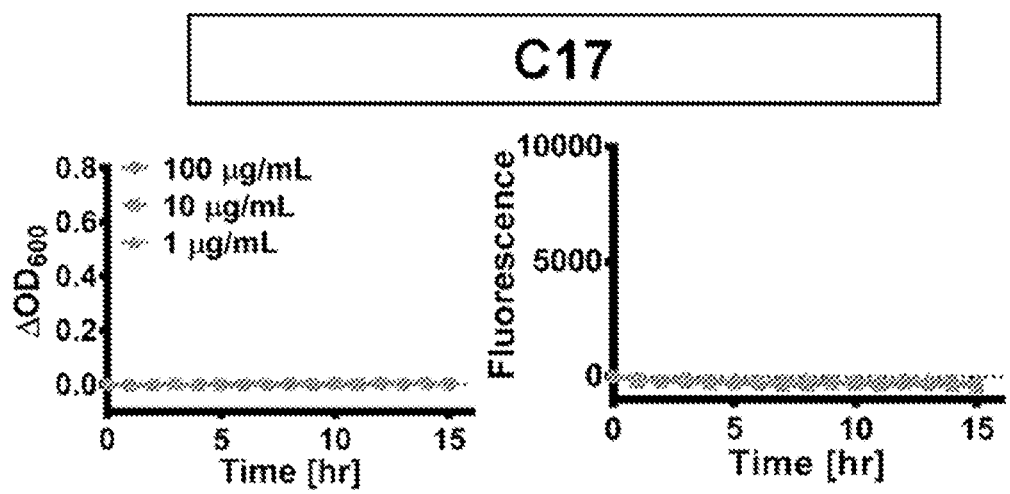
Figure 12C:
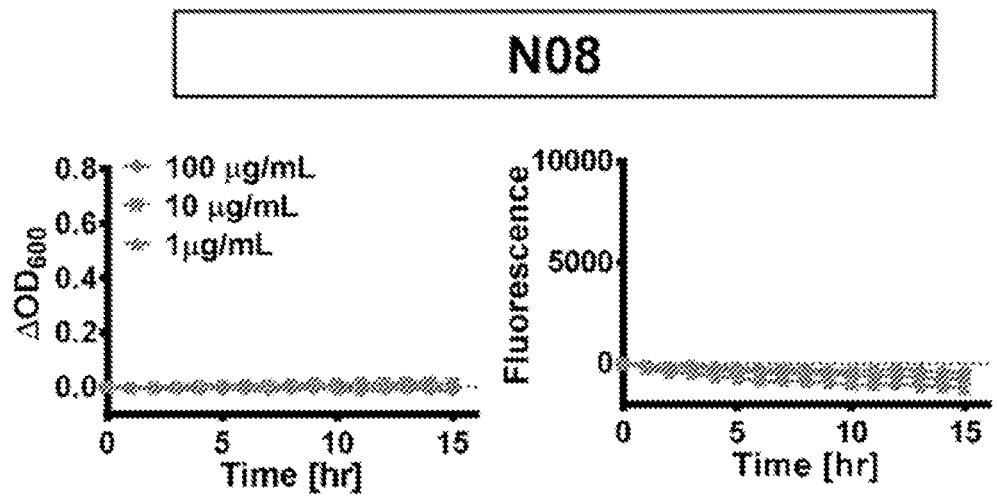

Evidence that compound N08 inhibits protein expression. Many effective antimicrobial compounds are protein synthesis inhibitors. A carbapenem-susceptible Kp233 strain carrying a plasm id that encodes an unstable variant of green fluorescent protein (GFP) was used to assess whether these compounds could inhibit GFP expression [24]. As a control, it was first confirmed that none of these compounds fluoresced under the conditions of this experiment (FIGS. 12A-12C).

In samples that were not treated with antibiotics or compounds, fluorescence at wavelength 515 nm increased over time as did the OD600, corresponding to bacterial growth (FIG. 7). Compounds O06 and C17 decreased both bacterial growth and protein synthesis at the highest concentration used. In contrast, low concentrations of compound N08 interfered with GFP fluorescence but not growth. This is consistent with inhibition of protein expression by N08 at the level of transcription, mRNA stability, or translation. However, specific effect on GFP that reduces fluorescence could not be ruled out.

Described herein is an untargeted, whole cell-based assay and compounds identified using this assay that are active against CR-*K. pneumoniae*, an organism for which there are few antimicrobial agents. This assay was used in a high-throughput format to test members of a fungal extract library as well as members of a chemical library to identify compounds active against a multidrug resistant, carbapenemase-producing *K. pneumoniae* strain. Fungal extracts with the greatest activity were shown to contain patulin, a known natural product. Furthermore, three synthetic chemical compounds designated O06, C17, and N08 with antibacterial activity were also identified. At lower concentrations, compound O06 functioned as an inhibitor of sugar transport or fermentation but had little impact on cell viability, while at higher concentrations it decreased bacterial viability. It is expected that compounds similar to O06 will be of use to researchers seeking to inhibit bacterial sugar metabolism or for treatment of antibiotic resistant bacterial infections in a subject (e.g., human). Compound C17 decreased both sugar metabolism and growth of CR-*K. pneumoniae* in the absence of efflux inhibition. In the presence of efflux inhibition, compound N08 was the most highly active against resistant GNRs as well as MRSA. Consistent with preliminary observations, N08 acts as an inhibitor of protein expression and possibly synthesis, but appears to function principally as a bacteriostatic agent. Formulations of N08 that prevent the tendency of N08 to aggregate in aqueous media would be expected to have the highest utility in the treatment of antibiotic resistant bacterial infections.

Patulin, the natural product identified in the screen of fungal extracts, was first discovered as a secondary metabolite of *Penicillium* moulds in 1943 [25]. It was subsequently demonstrated to be a cure for the common cold when used as a nasal wash in the first recorded double-blind, placebo-controlled clinical trial [26, 27]. Its activity against both Gram-negative and Gram-positive bacteria, particularly in biofilms, has been reported [28-31], and there is evidence that patulin functions as an inhibitor of quorum sensing [28, 32], or alternately as an inhibitor of alanine racemase [8]. The use of patulin is specifically contemplated for the treatment of superficial or mucosal infections caused by multi-drug resistant GNR.

The data provided herein indicate that compound O06 functions principally as an inhibitor of *K. pneumoniae* sugar transport or fermentation at lower concentrations. Glucose transport is essential for the replication of *Leishmania Mexicana* promastigotes [35, 36]. This property was exploited in high-throughput screens to identify inhibitors of the *L. mexicana* and human hexose transporters LmGT2 and Glut1, respectively [37, 38]. While compound O06 was identified as active in both screens, the results of a secondary screen to directly measure glucose transport are not reported. It is, therefore contemplated that O06 may also function as a hexose analog that competitively inhibits sugar transport.

Compound N08 has been flagged in diverse screens including one for inhibition of Human tyrosyl-DNA phosphodiesterase 1 (TDP1) and another for inhibition of Lassa virus entry [39-41]. It was previously identified in a primary screen for inhibitors of *S. aureus* teichoic acid biosynthesis but was ultimately not found to have this activity in secondary screens [42, 43]. This function would not provide a mechanism for the broad-spectrum activity of N08 as Gram-negative organisms do not synthesize teichoic acid. Compound N08 is also the subject of multiple patent applications disclosing its function as an inhibitor of PAS kinase, potassium channel closure, and TGF-β with possible applications to the treatment of diabetes mellitus, epilepsy, and scarring, respectively [44-46]. This suggests that toxicity to human cells is unlikely to limit its use.

The high-throughput screen described herein identified compounds active against a highly resistant, carbapenemase-producing strain of *K. pneumoniae*. The use of such an extremely resistant organism in a whole cell screen directly identified compounds active in the face of cell envelope impermeability and efflux. Compound N08 has broad spectrum anti-bacterial activity but non-ideal chemical properties. While its propensity to precipitate in aqueous media would limit its direct utility as a therapeutic, this also suggests that its activity was underestimated in our assays. We propose that this compound could serve as a scaffold for a broad-spectrum, highly effective antibacterial agent if solubility and efflux resistance is improved by structural optimization or by development of an adequate formulation for delivery to a subject.

REFERENCES

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason.

Bonomo R A, Burd E M, Conly J, Limbago B M, Poirel L, Segre J A, et al. Carbapenemase-Producing Organisms: A Global Scourge. Clin Infect Dis. 2018; 66(8):1290-7. Epub 2017/11/23. doi: 10.1093/cid/cix893. PubMed PMID: 29165604; PubMed Central PMCID: PMCPMC5884739.

Logan L K, Weinstein R A. The Epidemiology of Carbapenem-Resistant Enterobacteriaceae: The Impact and Evolution of a Global Menace. J Infect Dis. 2017; 215 (suppl_1):528-536. Epub 2017/04/05. doi: 10.1093/infdis/jiw282. PubMed PMID: 28375512; PubMed Central PMCID: PMCPMC5853342.

Xu L, Sun X, Ma X. Systematic review and meta-analysis of mortality of patients infected with carbapenem-resistant *Klebsiella pneumoniae*. Annals of Clinical Microbiology and Antimicrobials. 2017; 16(1):18. doi: 10.1186/s12941-017-0191-3.

Ahmad I, Nawaz N, Dermani F K, Kohlan A K, Saidijam M, Patching S G. Bacterial Multidrug Efflux Proteins: A Major Mechanism of Antimicrobial Resistance. Curr Drug Targets. 2018. doi: 10.2174/1389450119666180426103300. PubMed PMID: 29697028.

Dam S, Pages J M, Masi M. Stress responses, outer membrane permeability control and antimicrobial resistance in Enterobacteriaceae. Microbiology. 2018; 164(3):260-7. doi: 10.1099/mic.0.000613. PubMed PMID: 29458656.

Graef F, Vukosavljevic B, Michel J P, Wirth M, Ries 0, De Rossi C, et al. The bacterial cell envelope as delimiter of anti-infective bioavailability—An in vitro permeation model of the Gram-negative bacterial inner membrane. J Control Release. 2016; 243:214-24. doi: 10.1016/j.jconrel.2016.10.018. PubMed PMID: 27769806.

Lewis K. Platforms for antibiotic discovery. Nat Rev Drug Discov. 2013; 12(5):371-87. Epub 2013/05/01. doi: 10.1038/nrd3975. PubMed PMID: 23629505.

Wang Y, Yang C, Xue W, Zhang T, Liu X, Ju J, et al. Selection and characterization of alanine racemase inhibitors against *Aeromonas hydrophila*. BMC Microbiol. 2017; 17(1):122. Epub 2017/05/27. doi: 10.1186/s12866-017-1010-x. PubMed PMID: 28545531; PubMed Central PMCID: PMCPMC5445283.

de Melo F T, de Oliveira I M, Greggio S, Dacosta J C, Guecheva T N, Saffi J, et al. DNA damage in organs of mice treated acutely with patulin, a known mycotoxin. Food Chem Toxicol. 2012; 50(10):3548-55. Epub 2012/01/10. doi: 10.1016/j.fct.2011.12.022. PubMed PMID: 22222931.

Liu B H, Yu F Y, Wu T S, Li S Y, Su M C, Wang M C, et al. Evaluation of genotoxic risk and oxidative DNA damage in mammalian cells exposed to mycotoxins, patulin and citrinin. Toxicol Appl Pharmacol. 2003; 191 (3):255-63. Epub 2003/09/19. PubMed PMID: 13678658.

Tegos G P, Masago K, Aziz F, Higginbotham A, Stermitz F R, Hamblin M R. Inhibitors of bacterial multidrug efflux pumps potentiate antimicrobial photoinactivation. Antimicrob Agents Chemother. 2008; 52(9):3202-9. doi: 10.1128/AAC.00006-08. PubMed PMID: 18474586; PubMed Central PMCID: PMCPMC2533468.

McCloud T G. High throughput extraction of plant, marine and fungal specimens for preservation of biologically active molecules. Molecules. 2010; 15(7):4526-63. Epub 2010/07/27. doi: 10.3390/molecules15074526. PubMed PMID: 20657375.

Renau T E, Leger R, Flamme E M, Sangalang J, She M W, Yen R, et al. Inhibitors of efflux pumps in *Pseudomonas aeruginosa* potentiate the activity of the fluoroquinolone antibacterial levofloxacin. J Med Chem. 1999; 42(24): 4928-31. Epub 1999/12/10. PubMed PMID: 10585202.

George A M, Hall R M, Stokes H W. Multidrug resistance in *Klebsiella pneumoniae*: a novel gene, ramA, confers a multidrug resistance phenotype in *Escherichia coli*. Microbiology. 1995; 141 (Pt 8):1909-20. Epub 1995/08/01. doi: 10.1099/13500872-141-8-1909. PubMed PMID: 7551053.

Ping Y, Ogawa W, Kuroda T, Tsuchiya T. Gene cloning and characterization of KdeA, a multidrug efflux pump from *Klebsiella pneumoniae*. Biol Pharm Bull. 2007; 30(10): 1962-4. Epub 2007/10/06. PubMed PMID: 17917272.

Ymele-Leki P, Cao S, Sharp J, Lambert K G, McAdam A J, Husson R N, et al. A high-throughput screen identifies a new natural product with broad-spectrum antibacterial activity. PLoS ONE. 2012; 7(2):e31307. Epub 2012/02/24. doi: 10.1371/journal.pone.0031307 PONE-D-11-20901 [pii]. PubMed PMID: 22359585; PubMed Central PMCID: PMC3281070.

Zhang J H, Chung T D, Oldenburg K R. A Simple Statistical Parameter for Use in Evaluation and Validation of High Throughput Screening Assays. J Biomol Screen. 1999; 4(2):67-73. Epub 2000/06/06. doi: 10.1177/108705719900400206. PubMed PMID: 10838414.

Escoula L. Effect of carbohydrates on the antibacterial activity of patulin on *Streptococcus bovis*. Can J Microbiol. 1982; 28(7):881-3. Epub 1982/07/01. PubMed PMID: 7172139.

Lee K S, Roschenthaler R T. DNA-damaging activity of patulin in *Escherichia coli*. Appl Environ Microbiol. 1986; 52(5):1046-54. Epub 1986/11/01. PubMed PMID: 2431653; PubMed Central PMCID: PMCPMC239171.

Lomovskaya O, Warren M S, Lee A, Galazzo J, Fronko R, Lee M, et al. Identification and characterization of inhibitors of multidrug resistance efflux pumps in *Pseudomonas aeruginosa*: novel agents for combination therapy. Antimicrob Agents Chemother. 2001; 45(1):105-16. Epub 2000/12/20. doi: 10.1128/AAC.45.1.105-116.2001. PubMed PMID: 11120952; PubMed Central PMCID: PMC90247.

Hasdemir U O, Chevalier J, Nordmann P, Pages J M. Detection and prevalence of active drug efflux mechanism in various multidrug-resistant *Klebsiella pneumoniae* strains from Turkey. J Clin Microbiol. 2004; 42(6):2701-6. Epub 2004/06/09. doi: 10.1128/JCM.42.6.2701-2706.2004 42/6/2701 [pii]. PubMed PMID: 15184455; PubMed Central PMCID: PMC427859.

Spratt B G. Distinct penicillin binding proteins involved in the division, elongation, and shape of *Escherichia coli* K12. Proceedings of the National Academy of Sciences. 1975; 72(8):2999-3003.

Lorian V, Waluschka A, Kim Y. Abnormal morphology of bacteria in the sputa of patients treated with antibiotics. J Clin Microbiol. 1982; 16(2):382-6. Epub 1982/08/01. PubMed PMID: 6749897; PubMed Central PMCID: PMC272365.

Andersen J B, Sternberg C, Poulsen L K, Bjorn S P, Givskov M, Molin S. New unstable variants of green fluorescent protein for studies of transient gene expression in bacteria. Appl Environ Microbiol. 1998; 64(6):2240-6. Epub 1998/06/03. PubMed PMID: 9603842; PubMed Central PMCID: PMC106306.

Hooper I R, Anderson H W, Skell P, Carter H E. The Identity of Clavacin with Patulin. Science. 1944; 99(2558):16. Epub 1944/01/07. doi: 10.1126/science.99.2558.16. PubMed PMID: 17844551.

Boyd E M. Patulin. Can Med Assoc J. 1944; 50(2):159. Epub 1944/02/01. PubMed PMID: 20323004; PubMed Central PMCID: PMCPMC1583456.

Chalmers I, Clarke M. Commentary: the 1944 patulin trial: the first properly controlled multicenter trial conducted under the aegis of the British Medical Research Council. Int J Epidemiol. 2004; 33(2):253-60. Epub 2004/04/15. doi: 10.1093/ije/dyh162. PubMed PMID: 15082623.

Liaqat I, Bachmann R T, Edyvean R G. Type 2 quorum sensing monitoring, inhibition and biofilm formation in marine microorganisms. Curr Microbiol. 2014; 68(3):342-51. Epub 2013/10/30. doi: 10.1007/s00284-013-0484-5. PubMed PMID: 24166155.

Liaqat I, Bachmann R T, Sabri A N, Edyvean R G. Isolate-specific effects of patulin, penicillic Acid and EDTA on biofilm formation and growth of dental unit water line biofilm isolates. Curr Microbiol. 2010; 61(2):148-56. Epub 2010/01/30. doi: 10.1007/s00284-010-9591-8. PubMed PMID: 20111864.

Paytubi S, de La Cruz M, Tormo J R, Martin J, Gonzalez I, Gonzalez-Menendez V, et al. A High-Throughput Screening Platform of Microbial Natural Products for the Discovery of Molecules with Antibiofilm Properties against *Salmonella*. Front Microbiol. 2017; 8:326. Epub 2017/03/18. doi: 10.3389/fmicb.2017.00326. PubMed PMID: 28303128; PubMed Central PMCID: PMCPMC5332434.

Zhou J, Bi S, Chen H, Chen T, Yang R, Li M, et al. Anti-Biofilm and Antivirulence Activities of Metabolites from *Plectosphaerella cucumerina* against *Pseudomonas aeruginosa*. Front Microbiol. 2017; 8:769. Epub 2017/05/19. doi: 10.3389/fmicb.2017.00769. PubMed PMID: 28515715; PubMed Central PMCID: PMCPMC5413567.

Rasmussen T B, Skindersoe M E, Bjarnsholt T, Phipps R K, Christensen K B, Jensen P O, et al. Identity and effects of quorum-sensing inhibitors produced by *Penicillium* species. Microbiology. 2005; 151(Pt 5):1325-40. Epub 2005/05/05. doi: 10.1099/mic.0.27715-0. PubMed PMID: 15870443.

Jin H, Yin S, Song X, Zhang E, Fan L, Hu H. p53 activation contributes to patulin-induced nephrotoxicity via modulation of reactive oxygen species generation. Sci Rep. 2016; 6:24455. Epub 2016/04/14. doi: 10.1038/srep24455. PubMed PMID: 27071452; PubMed Central PMCID: PMCPMC4829895.

Song E, Xia X, Su C, Dong W, Xian Y, Wang W, et al. Hepatotoxicity and genotoxicity of patulin in mice, and its modulation by green tea polyphenols administration. Food Chem Toxicol. 2014; 71:122-7. Epub 2014/06/21. doi: 10.1016/j.fct.2014.06.009. PubMed PMID: 24949943.

Burchmore R J, Rodriguez-Contreras D, McBride K, Merkel P, Barrett M P, Modi G, et al. Genetic characterization of glucose transporter function in *Leishmania mexicana*. Proc Natl Acad Sci USA. 2003; 100(7):3901-6. Epub 2003/03/26. doi: 10.1073/pnas.0630165100. PubMed PMID: 12651954; PubMed Central PMCID: PMCPMC153020.

Rodriguez-Contreras D, Landfear S M. Metabolic changes in glucose transporter-deficient *Leishmania mexicana* and parasite virulence. J Biol Chem. 2006; 281(29):20068-76. Epub 2006/05/19. doi: 10.1074/jbc.M603265200. PubMed PMID: 16707495.

National Center for Biotechnology Information PubChem BioAssay Database. 2016 [2016-05-22]. AID=1207599]. Available from:

National Center for Biotechnology Information PubChem BioAssay Database. 2016. AID=1207598].

National Center for Biotechnology Information PubChem BioAssay Database. 2013. AID=6869791.

National Center for Biotechnology Information PubChem BioAssay Database. 2013. AID=6869781.

National Center for Biotechnology Information PubChem BioAssay Database. 2011. AID=540256].

Swoboda J G, Meredith T C, Campbell J, Brown S, Suzuki T, Bollenbach T, et al. Discovery of a small molecule that blocks wall teichoic acid biosynthesis in *Staphylococcus aureus*. ACS Chem Biol. 2009; 4(10):875-83. Epub 2009/08/20. doi: 10.1021/cb900151k. PubMed PMID: 19689117; PubMed Central PMCID: PMC2787957.

National Center for Biotechnology Information PubChem BioAssay Database. 2010 [Dec. 24, 2017]. AID=463173].

Kelly R C, McCall J M, Romero D L, inventors; BIOENERGENIX, assignee. HETEROCYCLIC COMPOUNDS FOR THE INHIBITION OF PASK. USA patent US2012277224. 2012.

Wu Y, Mi Y, Fu Y, Du X, Xu W, Yang S, et al., Pyrazolo [1,5-a]-pyrimidones derivatives and pharmaceutical compositions and uses thereof. USA patent U.S. Pat. No. 8,796,285. 2014.

Phipps R P, Woeller C, inventors; University of Rochester, assignee. Small molecule anti-scarring agents. USA2015.

The invention claimed is:

1. A pharmaceutical composition for the treatment of an antibiotic-resistant bacterial infection, the composition comprising a therapeutically effective amount of a compound of Formula II or stereoisomers, tautomers, or pharmaceutically acceptable salts thereof and a pharmaceutically acceptable carrier;

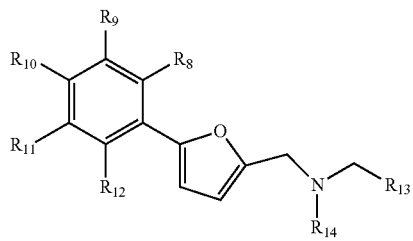

wherein:
- $R_8$, $R_9$, $R_{10}$, $R_{11}$, and $R_{12}$ independently are H, alkyl, aryl, heteroaryl, heteroalkyl, cycloalkyl, heterocyclyl, acyl, allyl, OH, alkoxy, cyano, carboxy, $CF_3$, halide, NH (alkyl), NH (aryl) or $NH_2$; $R_{13}$ and $R_{14}$ are independently H, alkyl, aryl, heteroaryl, heteroalkyl, cycloalkyl, heterocyclyl, acyl, or allyl;
- wherein any alkyl, alkenyl, cycloalkyl, heterocyclyl, heteroaryl or aryl is optionally substituted with 1, 2, or 3 groups selected from OH, CN, SH, $SO_2NH_2$, $SO_2(C_1-C_4)$ alkyl, $SO_2NH(C_1-C_4)$ alkyl, halogen, $NH_2$, $NH(C_1-C_4)$ alkyl, $N[(C_1-C_4)$ alkyl$]_2$, $C(O)NH_2$, COOH, COOMe, acetyl, $(C_1-C_8)$ alkyl, $O(C_1-C_8)$ alkyl, $O(C_1-C_5)$ haloalkyl, $(C_2-C_8)$ alkenyl, $(C_2-C_8)$ alkynyl, haloalkyl, thioalkyl, cyanomethylene, alkylaminyl, aryl, heteroaryl, substituted aryl, $NH_2$—C(O)-alkylene, NH (Me)-C(O)-alkylene, $CH_2$—C(O)-lower alkyl, C(O)-lower alkyl, alkylcarbonylaminyl, $CH_2$—[CH(OH)]$_m$—(CH$_2$)$_p$—OH, $CH_2$—[CH(OH)]$_m$—(CH$_2$)$_p$—$NH_2$ or $CH_2$-aryl-alkoxy; or wherein any alkyl, cycloalkyl or heterocyclyl is optionally substituted with oxo;
- "m" and "p" are independently 1, 2, 3, 4, 5 or 6, and
- a therapeutically effective amount of an efflux pump inhibitor.

2. The pharmaceutical composition according to claim 1, wherein
   (i) at least one of $R_8$, $R_9$, $R_{10}$, $R_{11}$, and $R_{12}$ is a chloride or a bromide, and/or
   (ii) at least one of $R_8$, $R_9$, $R_{10}$, $R_{11}$, and $R_{12}$ is a methoxy and/or
   (iii) $R_{13}$ is a 5 or 6 member cycloalkyl, heterocyclyl, aryl, or heteroaryl.

3. The pharmaceutical composition of claim 1, wherein the compound is selected from the following compounds;

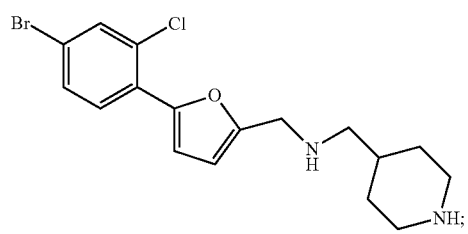

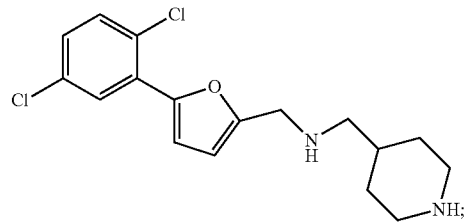

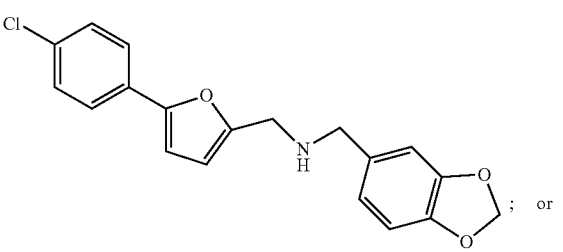

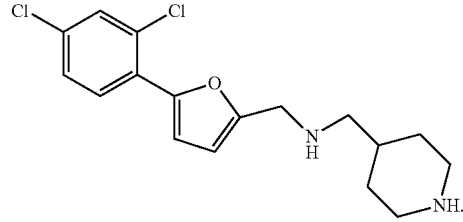

4. The pharmaceutical composition of claim 1, wherein the efflux pump inhibitor is phenylalanyl arginyl β-naphthylamide (PAβN).

* * * * *